US011534323B2

(12) United States Patent
Hansen et al.

(10) Patent No.: US 11,534,323 B2
(45) Date of Patent: *Dec. 27, 2022

(54) TOOLS AND METHODS FOR PLACING A MEDICAL APPLIANCE ON A USER

(71) Applicant: Coloplast A/S, Humlebaek (DK)

(72) Inventors: Jais Ask Hansen, Jaegerspris (DK); Niels Hvid, Vedbaek (DK); Daniel Gewecke Daugaard-Jensen, Frederiksberg (DK); Peter Flintholm Soerensen, Aarhus C (DK); Dan Boegsted Andersen, Copenhagen OE (DK); Niels Kristian Mäkinen Andersen, Glostrup (DK)

(73) Assignee: Coloplast A/S, Humlebaek (DK)

( * ) Notice: Subject to any disclaimer, the term of this patent is extended or adjusted under 35 U.S.C. 154(b) by 242 days.

This patent is subject to a terminal disclaimer.

(21) Appl. No.: 16/955,051

(22) PCT Filed: Dec. 20, 2018

(86) PCT No.: PCT/DK2018/050394
§ 371 (c)(1),
(2) Date: Jun. 18, 2020

(87) PCT Pub. No.: WO2019/120438
PCT Pub. Date: Jun. 27, 2019

(65) Prior Publication Data
US 2020/0375785 A1 Dec. 3, 2020

(30) Foreign Application Priority Data
Dec. 22, 2018 (DK) .......................... PA 2017 70995

(51) Int. Cl.
*A61B 90/30* (2016.01)
*A61F 5/44* (2006.01)
(Continued)

(52) U.S. Cl.
CPC .......... *A61F 5/4404* (2013.01); *A61B 90/361* (2016.02); *A61B 90/37* (2016.02); *A61F 5/445* (2013.01); *A61B 2560/0223* (2013.01)

(58) Field of Classification Search
CPC .................... A61F 5/4404; A61F 5/445; A61F 2002/6614; A61F 2002/6863;
(Continued)

(56) References Cited

U.S. PATENT DOCUMENTS 2,327,514 A    8/1943  Fenwick
2,542,233 A    2/1951  Carroll
(Continued)

FOREIGN PATENT DOCUMENTS

CN    203786580 U    8/2014
CN    104902399 A    9/2015
(Continued)

*Primary Examiner* — Joel Lamprecht
(74) *Attorney, Agent, or Firm* — Coloplast Corp., Coloplast A/S; Nick Baumann

(57) ABSTRACT

A method for operating an accessory device to guide the placement of an ostomy appliance on a user having a stoma. The method can include capturing an image or a sequence of images of the user applying the ostomy appliance to the user's body, processing the captured image or sequence of images, including: identifying a location of the stoma in one or more of the captured image or sequence of images, identifying a location of the ostomy appliance in one or more of the captured image or sequence of images, and generating location indicia representative of the location of the ostomy appliance with respect to the stoma in one or more of the captured image or sequence of images. A visual display including the location indicia associated with one or more of the captured image or sequence of images can be provided.

17 Claims, 29 Drawing Sheets

(51) Int. Cl.
  *A61B 90/00* (2016.01)
  *A61F 5/445* (2006.01)

(58) Field of Classification Search
  CPC .................. A61B 90/361; A61B 90/37; A61B
    2560/0223; A61B 2576/02; G06V 10/454;
    G06V 10/462; G06V 2201/03
  See application file for complete search history.

(56) References Cited

U.S. PATENT DOCUMENTS

| | | |
|---|---|---|
| 2,544,579 A | 3/1951 | Ardner |
| 3,214,502 A | 10/1965 | Schaar |
| 3,832,510 A | 8/1974 | Pfau et al. |
| 3,915,171 A | 10/1975 | Shermeta |
| 3,941,133 A | 3/1976 | Chen |
| 4,449,970 A | 5/1984 | Bevan et al. |
| 4,668,227 A | 5/1987 | Kay |
| 4,754,264 A | 6/1988 | Okada et al. |
| 4,775,374 A | 10/1988 | Cilento et al. |
| 4,982,742 A | 1/1991 | Claude |
| 5,016,645 A | 5/1991 | Williams et al. |
| 5,074,851 A | 12/1991 | Plass et al. |
| 5,111,812 A | 5/1992 | Swanson et al. |
| 5,167,650 A | 12/1992 | Johnsen et al. |
| 5,237,995 A | 8/1993 | Cano |
| 5,318,543 A | 6/1994 | Ross et al. |
| 5,358,488 A | 10/1994 | Suriyapa |
| 5,486,158 A | 1/1996 | Samuelsen |
| 5,593,397 A | 1/1997 | La Gro |
| 5,672,163 A | 9/1997 | Ferreira et al. |
| 5,677,221 A | 10/1997 | Tseng |
| 5,704,905 A | 1/1998 | Jensen et al. |
| 5,790,036 A | 8/1998 | Fisher et al. |
| 5,800,415 A | 9/1998 | Olsen |
| 5,816,252 A | 10/1998 | Faries, Jr. et al. |
| 5,834,009 A | 11/1998 | Sawers et al. |
| 5,879,292 A | 3/1999 | Sternberg et al. |
| 5,942,186 A | 8/1999 | Sanada et al. |
| 6,015,399 A | 1/2000 | Mracna et al. |
| 6,025,725 A | 2/2000 | Gershenfeld et al. |
| 6,057,689 A | 5/2000 | Saadat |
| 6,103,033 A | 8/2000 | Say et al. |
| 6,135,986 A | 10/2000 | Leisner et al. |
| 6,171,289 B1 | 1/2001 | Millot et al. |
| 6,206,864 B1 | 3/2001 | Kavanagh et al. |
| 6,407,308 B1 | 6/2002 | Roe et al. |
| 6,433,244 B1 | 8/2002 | Roe et al. |
| 6,482,491 B1 | 11/2002 | Samuelsen et al. |
| 6,485,476 B1 | 11/2002 | von Dyck et al. |
| 6,659,989 B1 | 12/2003 | Otto |
| 6,764,474 B2 | 7/2004 | Nielsen et al. |
| 7,066,919 B1 | 6/2006 | Sauerland et al. |
| 7,150,728 B2 | 12/2006 | Hansen et al. |
| 7,166,091 B1 | 1/2007 | Zeltner |
| 7,199,501 B2 | 4/2007 | Pei et al. |
| 7,214,217 B2 | 5/2007 | Pedersen et al. |
| 7,326,190 B2 | 2/2008 | Botten |
| 7,341,578 B2 | 3/2008 | von Bulow et al. |
| 7,367,965 B2 | 5/2008 | Poulsen et al. |
| 7,559,922 B2 | 7/2009 | Botten |
| 7,625,362 B2 | 12/2009 | Boehringer et al. |
| 7,641,612 B1 | 1/2010 | McCall |
| 7,670,289 B1 | 3/2010 | McCall |
| 7,943,812 B2 | 5/2011 | Stroebeck et al. |
| 7,981,098 B2 | 7/2011 | Boehringer et al. |
| 8,061,360 B2 | 11/2011 | Locke et al. |
| 8,277,427 B2 | 10/2012 | Edvardsen et al. |
| 8,319,003 B2 | 11/2012 | Olsen et al. |
| 8,398,575 B1 | 3/2013 | McCall |
| 8,398,603 B2 | 3/2013 | Thirstrup et al. |
| 8,399,732 B2 | 3/2013 | Oelund et al. |
| 8,409,158 B2 | 4/2013 | Edvardsen et al. |
| 8,449,471 B2 | 5/2013 | Tran |
| 8,500,718 B2 | 8/2013 | Locke et al. |
| 8,632,492 B2 | 1/2014 | DeLegge |
| 8,680,991 B2 | 3/2014 | Tran |
| 8,684,982 B2 | 4/2014 | Nguyen-DeMary et al. |
| 8,740,865 B2 | 6/2014 | Krystek et al. |
| 8,795,257 B2 | 8/2014 | Coulthard et al. |
| 8,821,464 B2 | 9/2014 | Hanuka et al. |
| 8,975,465 B2 | 3/2015 | Hong et al. |
| 9,046,085 B2 | 6/2015 | Schoess et al. |
| 9,066,812 B2 | 6/2015 | Edvardsen et al. |
| 9,216,104 B2 | 12/2015 | Thirstrup et al. |
| 9,308,332 B2 | 4/2016 | Heppe |
| 9,322,797 B1 | 4/2016 | Lastinger et al. |
| 9,629,964 B2 | 4/2017 | Wuepper |
| 9,693,908 B2 | 7/2017 | Eriksson et al. |
| 9,770,359 B2 | 9/2017 | Edvardsen et al. |
| 9,788,991 B2 | 10/2017 | Bird |
| 9,867,934 B2 | 1/2018 | Heppe |
| 9,928,341 B2 | 3/2018 | Angelides |
| 10,016,298 B2 | 7/2018 | Thirstrup et al. |
| D826,740 S | 8/2018 | Stevens et al. |
| 10,500,084 B2 | 12/2019 | Hansen et al. |
| 10,531,977 B2 | 1/2020 | Schoess et al. |
| 10,646,370 B2 | 5/2020 | Keleny et al. |
| 10,792,184 B2 | 10/2020 | Hvid et al. |
| 10,799,385 B2 | 10/2020 | Hansen et al. |
| 10,849,781 B2 | 12/2020 | Hansen et al. |
| 10,874,541 B2 | 12/2020 | Seres et al. |
| 10,987,243 B2 | 4/2021 | Thirstrup et al. |
| 11,096,818 B2 | 8/2021 | Thirstrup et al. |
| 11,406,525 B2 | 8/2022 | Seres et al. |
| 2002/0019615 A1 | 2/2002 | Roe et al. |
| 2003/0132763 A1 | 7/2003 | Ellenz |
| 2003/0169032 A1 | 9/2003 | Minchole et al. |
| 2004/0030305 A1 | 2/2004 | Sakamoto |
| 2004/0036484 A1 | 2/2004 | Tamai |
| 2004/0078219 A1 | 4/2004 | Kaylor et al. |
| 2004/0100376 A1 | 5/2004 | Lye et al. |
| 2004/0111072 A1* | 6/2004 | McKissick ............ A61F 5/445 604/332 |
| 2004/0133175 A1 | 7/2004 | Hagedorn-Olsen |
| 2004/0171999 A1 | 9/2004 | Andersen et al. |
| 2004/0216833 A1 | 11/2004 | Fleming et al. |
| 2005/0054997 A1 | 3/2005 | Buglino et al. |
| 2005/0065488 A1 | 3/2005 | Elliott |
| 2005/0070863 A1 | 3/2005 | von Bulow et al. |
| 2005/0085779 A1 | 4/2005 | Poulsen et al. |
| 2005/0101841 A9 | 5/2005 | Kaylor et al. |
| 2005/0240163 A1 | 10/2005 | Andersen |
| 2005/0261645 A1 | 11/2005 | Conrad et al. |
| 2006/0015081 A1 | 1/2006 | Suzuki et al. |
| 2006/0025727 A1 | 2/2006 | Boehringer et al. |
| 2006/0194324 A1 | 8/2006 | Faries, Jr. et al. |
| 2006/0271002 A1 | 11/2006 | Botten |
| 2007/0035405 A1 | 2/2007 | Wada et al. |
| 2007/0135782 A1 | 6/2007 | Bager et al. |
| 2007/0185464 A1 | 8/2007 | Fattman et al. |
| 2008/0071214 A1 | 3/2008 | Locke et al. |
| 2008/0075934 A1 | 3/2008 | Barlow, Jr. et al. |
| 2008/0091154 A1 | 4/2008 | Botten |
| 2008/0140057 A1 | 6/2008 | Wood et al. |
| 2008/0234641 A1 | 9/2008 | Locke et al. |
| 2008/0275327 A1 | 11/2008 | Faarbaek et al. |
| 2008/0278337 A1 | 11/2008 | Huang et al. |
| 2008/0300559 A1 | 12/2008 | Gustafson et al. |
| 2008/0306459 A1 | 12/2008 | Albrectsen |
| 2009/0012501 A1 | 1/2009 | Boehringer et al. |
| 2009/0118600 A1 | 5/2009 | Ortiz et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0227969 A1 | 9/2009 | Jaeb et al. |
| 2009/0247970 A1 | 10/2009 | Keleny et al. |
| 2010/0010460 A1 | 1/2010 | Butler |
| 2010/0030167 A1 | 2/2010 | Thirstrup et al. |
| 2010/0036206 A1 | 2/2010 | Lorio |
| 2010/0072271 A1 | 3/2010 | Thorstensson |
| 2011/0034890 A1 | 2/2011 | Stroebech et al. |
| 2011/0077497 A1 | 3/2011 | Oster et al. |
| 2011/0130642 A1 | 6/2011 | Jaeb et al. |

(56) References Cited

U.S. PATENT DOCUMENTS

| | | |
|---|---|---|
| 2012/0013130 A1 | 1/2012 | Jung |
| 2012/0143154 A1 | 6/2012 | Edvardsen et al. |
| 2012/0143155 A1 | 6/2012 | Edvardsen et al. |
| 2012/0253224 A1 | 10/2012 | Mir et al. |
| 2012/0258302 A1 | 10/2012 | Hunt et al. |
| 2012/0259230 A1 | 10/2012 | Riley |
| 2012/0283678 A1 | 11/2012 | Nguyen-Demary et al. |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1 | 3/2013 | Schertiger et al. |
| 2013/0102979 A1 | 4/2013 | Coulthard et al. |
| 2013/0138065 A1 | 5/2013 | Buus |
| 2013/0150769 A1 | 6/2013 | Heppe |
| 2013/0165862 A1 | 6/2013 | Griffith et al. |
| 2013/0192604 A1 | 8/2013 | Persson et al. |
| 2013/0226116 A1 | 8/2013 | Edvardsen et al. |
| 2013/0231620 A1 | 9/2013 | Thirstrup et al. |
| 2013/0261575 A1 | 10/2013 | Kiyoshi |
| 2013/0303867 A1 | 11/2013 | Elfstrom et al. |
| 2013/0324952 A1 | 12/2013 | Krystek et al. |
| 2014/0051946 A1 | 2/2014 | Arne et al. |
| 2014/0200538 A1 | 7/2014 | Euliano et al. |
| 2014/0236111 A1 | 8/2014 | Casado et al. |
| 2014/0236335 A1 | 8/2014 | Lewis et al. |
| 2014/0276501 A1 | 9/2014 | Cisko |
| 2014/0288381 A1 | 9/2014 | Faarbaek et al. |
| 2014/0323909 A1 | 10/2014 | Kim |
| 2014/0327433 A1 | 11/2014 | Anway et al. |
| 2015/0231802 A1 | 8/2015 | Quan et al. |
| 2015/0250639 A1 | 9/2015 | Thirstrup et al. |
| 2015/0257923 A1 | 9/2015 | Thirstrup et al. |
| 2015/0342777 A1 | 12/2015 | Seres et al. |
| 2015/0374896 A1 | 12/2015 | Du et al. |
| 2016/0084869 A1 | 3/2016 | Yuen et al. |
| 2016/0158056 A1 | 6/2016 | Davis et al. |
| 2016/0158969 A1 | 6/2016 | McLane et al. |
| 2016/0166438 A1 | 6/2016 | Rovaniemi |
| 2016/0218555 A1 | 7/2016 | Slaby et al. |
| 2016/0235581 A1 | 8/2016 | Keleny et al. |
| 2016/0278990 A1 | 9/2016 | Chen |
| 2016/0284084 A1 | 9/2016 | Gurcan et al. |
| 2016/0305776 A1 | 10/2016 | Mårtensson et al. |
| 2016/0310140 A1 | 10/2016 | Belson et al. |
| 2016/0310329 A1 | 10/2016 | Patel et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0079576 A1 | 3/2017 | Stroebech et al. |
| 2017/0112658 A1 | 4/2017 | Hosono |
| 2017/0140103 A1 | 5/2017 | Angelides |
| 2017/0156920 A1 | 6/2017 | Hunt et al. |
| 2017/0262986 A1 | 9/2017 | Xiong et al. |
| 2017/0340474 A1 | 11/2017 | Thirstrup et al. |
| 2017/0348137 A1 | 12/2017 | Hvid et al. |
| 2017/0360592 A1 | 12/2017 | Carrubba |
| 2018/0049667 A1 | 2/2018 | Heppe |
| 2018/0055359 A1 | 3/2018 | Shamim et al. |
| 2018/0171183 A1 | 6/2018 | Sakurai et al. |
| 2019/0133810 A1 | 5/2019 | Seres et al. |
| 2019/0133811 A1 | 5/2019 | Seres et al. |
| 2019/0133812 A1 | 5/2019 | Seres et al. |
| 2019/0142623 A1 | 5/2019 | Schoess et al. |
| 2019/0175386 A1 | 6/2019 | Monty |
| 2019/0192066 A1 | 6/2019 | Schoess et al. |
| 2019/0192332 A1 | 6/2019 | Hansen et al. |
| 2019/0192333 A1 | 6/2019 | Hansen et al. |
| 2019/0192334 A1 | 6/2019 | Hansen et al. |
| 2019/0240059 A1 | 8/2019 | Seres et al. |
| 2019/0247050 A1 | 8/2019 | Goldsmith |
| 2019/0374163 A1 | 12/2019 | Faarbaek et al. |
| 2019/0374372 A1 | 12/2019 | Seres et al. |
| 2020/0188161 A1 | 6/2020 | Seres et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Muñoz Herencia |
| 2020/0306074 A1 | 10/2020 | Speiermann et al. |
| 2020/0330258 A1 | 10/2020 | Hansen et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337883 A1 | 10/2020 | Hansen et al. |
| 2020/0375499 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0383637 A1 | 12/2020 | Hansen et al. |
| 2020/0383818 A1 | 12/2020 | Hansen et al. |
| 2020/0383819 A1 | 12/2020 | Sletten et al. |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |
| 2021/0007663 A1 | 1/2021 | Svanegaard et al. |
| 2021/0007881 A1 | 1/2021 | Svanegaard et al. |
| 2021/0015654 A1 | 1/2021 | Hansen et al. |
| 2021/0038424 A1 | 2/2021 | Svanegaard et al. |
| 2021/0059603 A1 | 3/2021 | Svanegaard et al. |
| 2021/0085511 A1 | 3/2021 | Hansen et al. |
| 2021/0085512 A1 | 3/2021 | Hansen et al. |
| 2021/0177642 A1 | 6/2021 | Andersen et al. |
| 2021/0212855 A1 | 7/2021 | Hansen et al. |
| 2021/0338471 A1 | 11/2021 | Nolan et al. |
| 2021/0361464 A1 | 11/2021 | Larsen et al. |
| 2021/0361465 A1 | 11/2021 | Hansen et al. |
| 2021/0361467 A1 | 11/2021 | Hansen et al. |
| 2021/0369197 A1 | 12/2021 | Hansen et al. |
| 2021/0369488 A1 | 12/2021 | Hansen et al. |
| 2021/0369489 A1 | 12/2021 | Hansen et al. |
| 2021/0369490 A1 | 12/2021 | Hansen et al. |
| 2021/0386368 A1 | 12/2021 | Carlsson et al. |
| 2022/0079802 A1 | 3/2022 | Hansen |
| 2022/0079803 A1 | 3/2022 | Windeballe et al. |
| 2022/0087851 A1 | 3/2022 | Stroebech |
| 2022/0117771 A1 | 4/2022 | Fearn et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |
| 2022/0265458 A1 | 8/2022 | Carlsson et al. |

FOREIGN PATENT DOCUMENTS

| | | |
|---|---|---|
| CN | 104980878 A | 10/2015 |
| CN | 105588856 A | 5/2016 |
| CN | 206271160 U | 6/2017 |
| CN | 206450708 U | 8/2017 |
| DE | 3836590 A1 | 5/1990 |
| DE | 19900611 C1 | 7/2000 |
| DE | 102011014321 A1 | 9/2012 |
| DE | 102011076219 A1 | 11/2012 |
| EP | 0168967 A1 | 1/1986 |
| EP | 0373782 B1 | 10/1994 |
| EP | 0416397 B1 | 5/1995 |
| EP | 0800804 A1 | 10/1997 |
| EP | 1275357 A2 | 1/2003 |
| EP | 1188157 B1 | 12/2005 |
| EP | 2108345 A1 | 10/2009 |
| EP | 2601915 A1 | 6/2013 |
| EP | 2489561 B1 | 8/2014 |

(56) References Cited

FOREIGN PATENT DOCUMENTS

| | | |
|---|---|---|
| EP | 3213727 B1 | 12/2019 |
| GB | 2343628 B | 10/2000 |
| GB | 2465742 B | 7/2012 |
| GB | 2542093 A | 3/2017 |
| JP | 2001087299 A | 4/2001 |
| JP | 2002055074 A | 2/2002 |
| JP | 2002224093 A | 8/2002 |
| JP | 2005323981 A | 11/2005 |
| JP | 2014033745 A | 2/2014 |
| KR | 20120003987 A | 1/2012 |
| RU | 2527155 C2 | 8/2014 |
| TW | 201201783 A | 1/2012 |
| WO | 1994015562 A1 | 7/1994 |
| WO | 1997010012 A1 | 3/1997 |
| WO | 1999033037 A1 | 7/1999 |
| WO | 1999036017 A1 | 7/1999 |
| WO | 2000079497 A1 | 12/2000 |
| WO | 2001013830 A1 | 3/2001 |
| WO | 2001050996 A1 | 7/2001 |
| WO | 2002052302 A2 | 7/2002 |
| WO | 2002099765 A1 | 12/2002 |
| WO | 2005082271 A2 | 9/2005 |
| WO | 2006008866 A1 | 1/2006 |
| WO | 2006094513 A2 | 9/2006 |
| WO | 2007000168 A1 | 1/2007 |
| WO | 2007059774 A2 | 5/2007 |
| WO | 2007098762 A1 | 9/2007 |
| WO | 2007133555 A2 | 11/2007 |
| WO | 2008057884 A2 | 5/2008 |
| WO | 2009006900 A1 | 1/2009 |
| WO | 2009052496 A1 | 4/2009 |
| WO | 2009112912 A2 | 9/2009 |
| WO | 2011003421 A1 | 1/2011 |
| WO | 2011004165 A1 | 1/2011 |
| WO | 2011061540 A1 | 5/2011 |
| WO | 2011105701 A2 | 9/2011 |
| WO | 2011123018 A1 | 10/2011 |
| WO | 2011139499 A1 | 11/2011 |
| WO | 2011161254 A2 | 12/2011 |
| WO | 2012068386 A1 | 5/2012 |
| WO | 2012/076022 A2 | 6/2012 |
| WO | 2014004207 A1 | 1/2014 |
| WO | 2014086369 A1 | 6/2014 |
| WO | 2015007284 A1 | 1/2015 |
| WO | 2015014774 A1 | 2/2015 |
| WO | 2015084462 A1 | 6/2015 |
| WO | 2016166731 A1 | 10/2016 |
| WO | 2017023794 A1 | 2/2017 |
| WO | 2017062042 A1 | 4/2017 |
| WO | 2017067558 A1 | 4/2017 |
| WO | 2017067560 A1 | 4/2017 |
| WO | 2017088153 A1 | 6/2017 |
| WO | 2017136696 A1 | 8/2017 |
| WO | 2017190752 A1 | 11/2017 |
| WO | 2018028756 A1 | 2/2018 |
| WO | 2019094635 A1 | 5/2019 |
| WO | 2019161863 A1 | 8/2019 |

\* cited by examiner

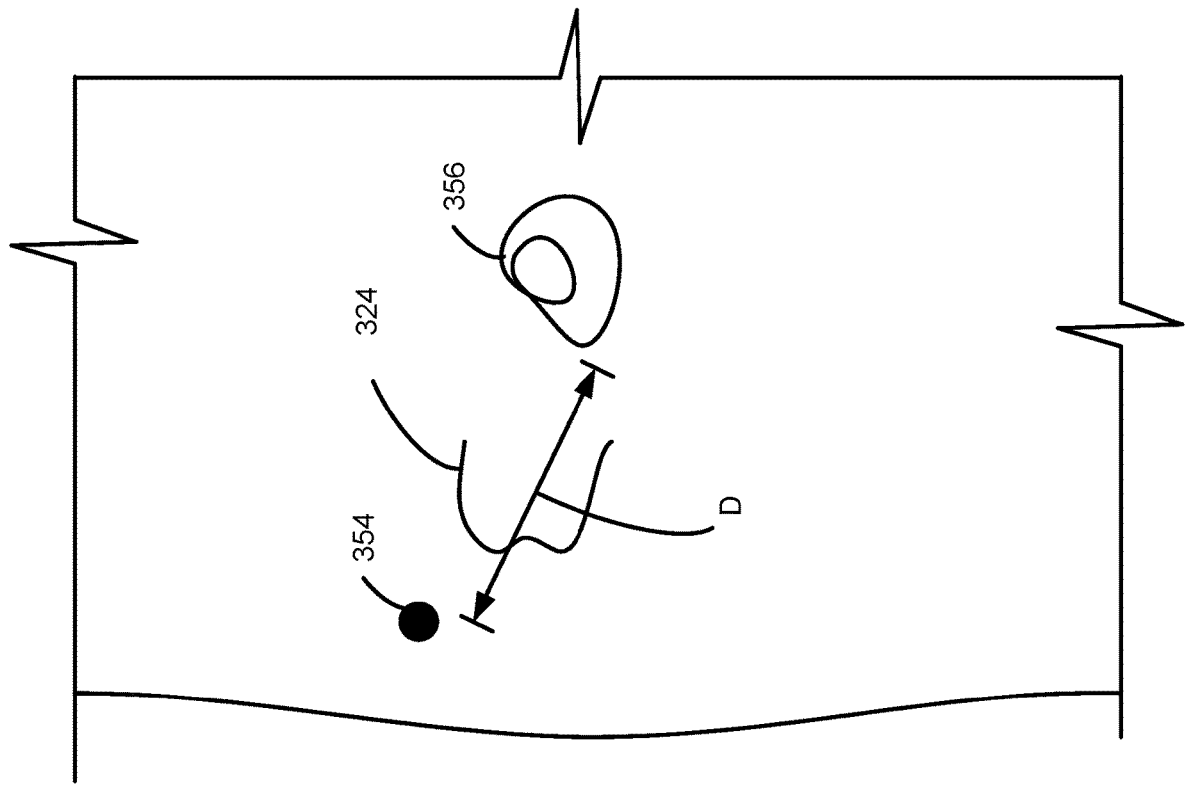
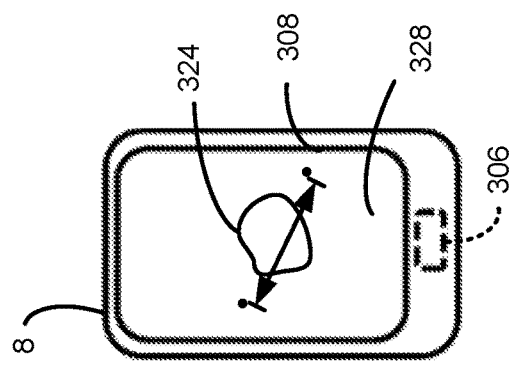
FIG. 19

TOOLS AND METHODS FOR PLACING A MEDICAL APPLIANCE ON A USER

The present disclosure relates to an ostomy system, devices thereof and methods for monitoring an ostomy appliance. In particular, the present disclosure relates to accessory devices and methods used in connection with ostomy appliances.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 19 illustrates the accessory device of FIG. 11 capturing an image of the stoma with reference locations.

DETAILED DESCRIPTION

Figure 1:
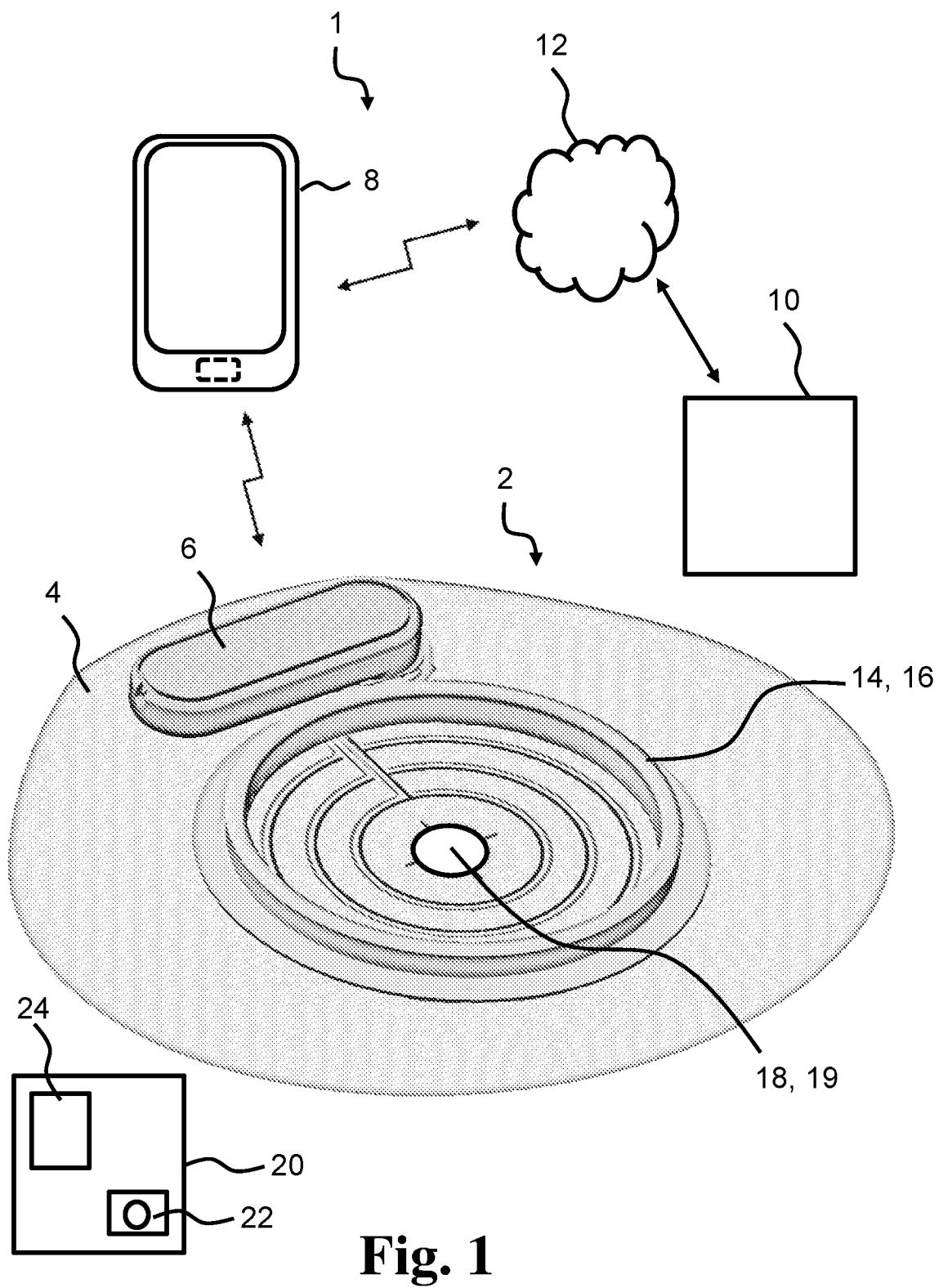
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the ostomy appliance is fitted on a user and the distal side is the opposite side or surface—the side or surface furthest away from the user in use.

The axial direction is defined as the direction of the stoma, when a user wears the ostomy appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, severity and rapidness of moisture propagation in the adhesive material provided for attaching the base plate to the skin surface of a user. Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The base plate comprises a first adhesive layer, also denoted center adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate to the skin surface of a user. The first adhesive layer may have a stomal opening with a center point.

The first adhesive layer may be made of a first composition. The first composition may comprise one or more polyisobutenes and/or styrene-isoprene-styrene. The first composition may comprise one or more hydrocoloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 3550% of the total adhesive composition. Preferably, the polybutene is polyisobutylene (PIB). Suitable hydrocolloids for incorporation in the first composition are selected from naturally occurring hydrocolloids, semisynthetic hydrocolloids and synthetic hydrocolloids. The first composition may comprise 20-60% hydrocolloids. A preferred hydrocolloid is carboxymethyl cellulose (CMC). The first composition may optionally contain other components, such as fillers, tackifiers, plasticizers, and other additives.

The first adhesive layer may have a plurality of sensor point openings. A sensor point opening of the first adhesive layer is optionally configured to overlap a part of an electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap parts of an electrode and the primary second sensor point openings configured to overlap parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap parts of an electrode and the secondary second sensor point openings configured to overlap parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap parts of an electrode and the tertiary second sensor point openings configured to overlap parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm, such as 0.8 mm or 1.0 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate may comprise a second layer. The second layer may be an adhesive layer, also denoted rim adhesive layer. The second layer may have a second radial extension that is larger than a first radial extension of the first adhesive layer at least in a first angular range of the base plate. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening with a center point.

The second adhesive layer may be made of a second composition. The second composition may comprise one or more polyisobutenes and/or styrene-isoprene-styrene. The second composition may comprise one or more hydrocoloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids and synthetic hydrocolloids. The second composition may comprise 20-60% hydrocolloids. A preferred hydrocolloid is carboxymethyl cellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocoloids. For example, the second adhesive layer may provide a stronger attachment to the skin compared to attachment to the skin provided by the first adhesive layer. Alternatively or additionally, the second adhesive layer may be thinner than the first adhesive layer. Alternatively or additionally, the second adhesive layer may be less water and/or sweat absorbing than the first adhesive layer. Alternatively or additionally, the second adhesive layer may be less mouldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate comprises one or more electrodes, such as a plurality of electrodes, such as two, three, four, five, six, seven or more electrodes. The electrodes, e.g. some or all the electrodes, may be arranged between the first adhesive layer and the second adhesive layer. The electrodes may be arranged in an electrode assembly, e.g. an electrode layer. An electrode comprises a connection part for connecting the electrodes to other components and/or interface terminals. An electrode may comprise one or more conductor parts and/or one or more sensing parts. The electrode assembly may be arranged between the first adhesive layer and the second adhesive layer. The base plate, e.g. the electrode assembly, may comprise a first electrode, a second electrode and optionally a third electrode. The base plate, e.g. the electrode assembly, may comprise a fourth electrode and/or a fifth electrode. The base plate, e.g. the electrode assembly, optionally comprises a sixth electrode. The base plate, e.g. the electrode assembly, may comprise a ground electrode. The ground electrode may comprise a first electrode part. The first electrode part of the ground electrode may form a ground for the first electrode. The ground electrode may comprise a second electrode part. The second electrode part of the ground electrode may form a ground for the second electrode. The ground electrode may comprise a third electrode part. The third electrode part of the ground electrode may form a ground for the third electrode. The ground electrode may comprise a fourth electrode part. The fourth electrode part of the ground electrode may form a ground for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

The ground electrode may comprise a first electrode part and a second electrode part, the first electrode part forming the ground for the first electrode and the second electrode part forming the ground for the second electrode. The first electrode part may form a closed loop.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair. The fourth electrode and the fifth electrode may form a sixth sensor or sixth electrode pair.

An electrode may comprise a sensing part or a plurality of sensing parts, i.e. the part(s) of an electrode that are used for sensing. The first electrode may comprise a first sensing part. The first sensing part may contact the first adhesive layer and is optionally arranged at least partly annularly around the stomal opening. The first electrode may comprise a first conductor part insulated from the first adhesive layer, e.g. by a masking element arranged between the first conductor part and the first adhesive layer. The first sensing part may extend at least 270 degrees around the stomal opening, such as at least 300 degrees around the stomal opening. The first sensing part of the first electrode may be arranged at a first ground distance from the first electrode part of the ground electrode. The first ground distance may be less than 5 mm, such as less than 3 mm, e.g. about 1.0 mm.

The second electrode may comprise a second sensing part. The second sensing part may contact the first adhesive layer. The second sensing part may be arranged at least partly annularly around the stomal opening. The second sensing part may extend at least 270 degrees around the stomal opening, such as at least 300 degrees around the stomal opening. The second sensing part of the second electrode may be arranged at a second ground distance from the second electrode part of the ground electrode. The second ground distance may be less than 5 mm, such as less than 3 mm, e.g. about 1.0 mm.

The first sensing part may be arranged at a first radial distance from the center point and the second sensing part may be arranged at a second radial distance from the center point. The second radial distance may be larger than the first radial distance. The second electrode may comprise a second conductor part insulated from the first adhesive layer, e.g. by a masking element arranged between the second conductor part and the first adhesive layer. The first radial distance may vary as a function of an angular position with respect to a zero direction from the center point. The second radial distance may vary as a function of an angular position with respect to a zero direction from the center point. The zero direction may be defined as the vertical upward direction when the base plate is in its intended wearing position on an upstanding user.

The first radial distance may be in the range from 5 mm to 40 mm, such as in the range from 10 mm to 25 mm, e.g. about 14 mm. The second radial distance may be in the range from 10 mm to 50 mm, such as in the range from 10 mm to 25 mm, e.g. about 18 mm.

The base plate may comprise a third electrode comprising a third connection part. The ground electrode may form a ground for the third electrode. The ground electrode may comprise a third electrode part, the third electrode part forming the ground for the third electrode. The third electrode may comprise a third conductor part insulated from the first adhesive layer, e.g. by a masking element arranged between the third conductor part and the first adhesive layer. The third electrode may comprise a third sensing part, the third sensing part contacting the first adhesive layer. The third sensing part may be arranged at least partly annularly around the stomal opening. The third sensing part may be arranged at a third radial distance from the center point. The third radial distance may be larger than the first radial distance and/or larger than the second radial distance. The third radial distance may be in the range from 15 mm to 50 mm. such as in the range from 20 mm to 30 mm, e.g. about 26 mm. The third sensing part may extend at least 270 degrees around the stomal opening, such as at least 300 degrees around the stomal opening. The third sensing part of the third electrode may be arranged at a third ground distance from the third electrode part of the ground electrode. The third ground distance may be less than 5 mm, such as less than 3 mm, e.g. about 1.0 mm. A base plate with a ground electrode, a first electrode, a second electrode, and a third electrode allows for a failsafe base plate in case e.g. the first electrode is cut or otherwise destroyed during preparation of the base plate.

The base plate may comprise a fourth electrode comprising a fourth connection part. The ground electrode may form a ground for the fourth electrode. The ground electrode may comprise a fourth electrode part, the fourth electrode part forming the ground for the fourth electrode. The fourth electrode may comprise one or a plurality of fourth sensing parts, such as at least five fourth sensing parts. The fourth sensing parts may be distributed around the stomal opening or a center point thereof. The fourth sensing parts may be arranged at respective fourth radial distances from the center point. The fourth radial distance(s) may be larger than the third radial distance. The fourth radial distance(s) may be in the range from 25 mm to 50 mm, such as about 30 mm The base plate may comprise a fifth electrode comprising a fifth connection part. The ground electrode may form a ground for the fifth electrode. The ground electrode may comprise a fifth electrode part, the fifth electrode part forming the ground for the fifth electrode. The fifth electrode may comprise one or a plurality of fifth sensing parts, such as at least five fifth sensing parts. The fifth sensing parts may be distributed around the stomal opening or a center point thereof. The fifth sensing parts may be arranged at respective fifth radial distances from the center point. The fifth radial distance may be larger than the third radial distance. The fifth radial distance may be equal to or larger than the fourth radial distance. The fifth radial distance(s) may be in the range from 25 mm to 50 mm, such as about 30 mm.

The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The base plate may comprise a second adhesive layer, wherein the plurality of electrodes is arranged between the first adhesive layer and the second adhesive layer.

The electrode assembly may comprise a support layer, also denoted a support film. One or more electrodes may be formed, e.g. printed, on the proximal side of the support layer. One or more electrodes may be formed, e.g. printed, on the distal side of the support layer. Thus, one or more electrodes may be arranged between the support layer and the first adhesive layer. The electrode assembly may have a stomal opening with a center point.

The support layer may comprise polymeric (e.g. polyurethane, PTFE, PVDF) and/or ceramic (e.g. alumina, silica) materials. In one or more exemplary base plates, the support layer is made of thermoplastic polyurethane (TPU). The support layer material may be made of or comprise one or more of polyester, a thermoplastic elastomer (TPE), polyamide, polyimide, Ethylene-vinyl acetate (EVA), polyurea, and silicones.

Exemplary thermoplastic elastomers of the support layer are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The electrode assembly/base plate may comprise a masking element configured to insulate at least parts of the electrodes from the first adhesive layer of the base plate. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s) A sensor point opening of the masking element overlaps at least one electrode of the electrode assembly when seen in the axial direction, e.g. to form a sensor point. For example, a primary sensor point opening may overlap a part of the ground electrode and/or a part of the fourth electrode. A secondary sensor point opening may overlap a part of the fourth electrode and/or a part of the fifth electrode. A tertiary sensor point opening may overlap a part of the fifth electrode and/or a part of the ground electrode.

The masking element may comprise one or more, such as a plurality of, terminal openings. A terminal opening may overlap with one or more connection parts of electrodes. In one or more exemplary base plates, each terminal opening overlaps with a single connection part of an electrode. The masking element may comprise polymeric (e.g. polyurethane, PTFE, PVDF) and/or ceramic (e.g. alumina, silica) materials. In one or more exemplary base plates, the masking element is made of or comprises thermoplastic polyurethane (TPU). In one or more exemplary base plates, the masking element is made of or comprises polyester. The masking element material may be made of or comprise one or more of polyester, a thermoplastic elastomer (TPE), polyamide, polyimide, Ethylene-vinyl acetate (EVA), polyurea, and silicones.

Exemplary thermoplastic elastomers of the masking element are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate may comprise a first intermediate element. The first intermediate element may be arranged between the electrodes/electrode layer and the first adhesive layer and/or between the second layer and the first adhesive layer. The first intermediate layer may be made of an insulating material.

The base plate may comprise a release liner. The release liner is a protective layer that protects adhesive layer(s) during transport and storage and is peeled off by the user prior to applying the base plate on the skin. The release liner may have a stomal opening with a center point.

The base plate may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening with a center point. The top layer may have a thickness in the range from 0.01 mm to 1.0 mm, e.g. in the range from 0.02 mm to 0.2 mm, such as 0.04 mm. The top layer may have a stomal opening with a center point.

The base plate comprises a monitor interface. The monitor interface may be configured for electrically and/or mechanically connecting the ostomy appliance (base plate) to the monitor device. The monitor interface may be configured for wirelessly connecting the ostomy appliance (base plate) to the monitor device. Thus, the monitor interface of the base plate is configured to electrically and/or mechanically couple the ostomy appliance and the monitor device.

The monitor interface of the base plate may comprise, e.g. as part of a first connector of the monitor interface, a coupling part for forming a mechanical connection, such as a releasable coupling between the monitor device and the base plate. The coupling part may be configured to engage with a coupling part of the monitor device for releasably coupling the monitor device to the base plate.

The monitor interface of the base plate may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes of the base plate/electrode assembly. The first intermediate element may be arranged between the terminal elements and the first adhesive layer. The first intermediate element may cover or overlap terminal element(s) of the base plate when seen in the axial direction. Thus, the first adhesive layer may be protected or experience more evenly distributed mechanical stress from the terminal elements of the base plate, in turn reducing the risk of terminal elements penetrating or otherwise damaging the first adhesive layer. The first intermediate element may protect or mechanically and/or electrically shield the first adhesive layer from the terminal elements of the base plate.

A terminal element, such as the ground terminal element, the first terminal element, the second terminal element, the third terminal element, the fourth terminal element, the fifth terminal element and/or the sixth terminal element, may comprise a distal end and a proximal end. A terminal element, such as the ground terminal element, the first terminal element, the second terminal element, the third terminal element, the fourth terminal element, the fifth terminal element and/or the sixth terminal element, may comprise a distal part, a centre part, and/or a proximal part. The distal part may be between the distal end and the centre part. The proximal part may be between the proximal end and the centre part. The proximal end/proximal part of a terminal element may contact a connection part of an electrode. A terminal element, such as the ground terminal element, the first terminal element, the second terminal element, the third terminal element, the fourth terminal element, the fifth terminal element and/or the sixth terminal element, may be gold plated copper.

The base plate may comprise a coupling ring or other coupling member for coupling an ostomy pouch to the base plate (two-part ostomy appliance). The center point may be defined as a center of the coupling ring.

The base plate has a stomal opening with a center point. The size and/or shape of the stomal opening is typically adjusted by the user or nurse before application of the ostomy appliance to accommodate the user's stoma. In one or more exemplary base plates, the user forms the stomal opening during preparation of the base plate for application.

A monitor device for an ostomy system comprising an ostomy appliance with a base plate is disclosed, the monitor device comprising a processor configured to apply a processing scheme; memory; a first interface connected to the processor and the memory, the first interface configured for collecting ostomy data from the base plate coupled to the first interface, the ostomy data comprising one or more, such as all, of first ostomy data from a first electrode pair of the base plate, second ostomy data from a second electrode pair of the base plate, and optionally third ostomy data from a third electrode pair of the base plate; and a second interface connected to the processor. To apply a processing scheme comprises obtain first parameter data based on the first ostomy data; obtain second parameter data based on the second ostomy data; and optionally obtain third parameter data based on the third ostomy data. To apply a processing scheme comprises determine an operating state of the base plate of the ostomy appliance. To determine the operating state of the base plate may be based on one or more, such as all, of the first parameter data, the second parameter data, the third parameter data, and fourth parameter data. The operating state may be indicative of a degree of radial erosion and/or radial swelling of the base plate, such as of the first adhesive layer, and/or an acute leakage risk for the ostomy appliance. The monitor device may be configured to transmit a monitor signal comprising monitor data indicative of the determined operating state of the base plate via the second interface. The monitor device may be configured to, in accordance with a determination that the operating state is a first operating state, transmit a first monitor signal comprising monitor data indicative of the first operating state of the base plate via the second interface. The monitor device may be configured to, in accordance with a determination that the operating state is a second operating state, transmit a second monitor signal comprising monitor data indicative of the second operating state of the base plate via the second interface.

An operating state in the present disclosure is indicative of the dynamic internal state of the ostomy appliance (e.g. of the base plate of the ostomy appliance currently being worn by the user) optionally related to adhesive performance of the ostomy appliance. Adhesive performance of the ostomy appliance may be related to an internal condition of the ostomy appliance (e.g. of the base plate of the ostomy appliance), such as an internal condition of an adhesive layer of the ostomy appliance. The adhesive performance, and thereby the operating state may be affected by several factors, such as humidity, temperature, misplacement of the ostomy appliance on the stoma, and/or malfunction of the ostomy appliance. The one or more factors alone or in combination impact the adhesive performance of the ostomy appliance. The operating state may be varying in time. The operating state may be indicative of a degree of erosion of the base plate.

Adhesive performance may be indicative of wear property, e.g. wear time and/or wear comfort. The operating state may comprise at least one of: a wear time, a quality of adhesion, and a moisture pattern representation. Wear time may comprise average wear time, nominal wear time, minimal wear time, maximal wear time, median wear time, and/or any of other statistical metric derivable from wear time. Wear time may comprise remaining wear time and/or current wear time and/or elapsed wear time. A quality of adhesion may comprise a metric indicative of erosion of a layer of the base plate, such as of the first adhesive layer. A moisture pattern representation may comprise one or more metrics or parameters representative or indicative of a moisture pattern (e.g. a moisture pattern type), e.g. a moisture pattern of the first adhesive layer.

An operating state may be configured to indicate whether the ostomy appliance is properly operational based on its adhesive performance (e.g. wear property, e.g. wear time and/or wear comfort). For example, the operating state may be indicative of the severity and/or imminence of a leakage (e.g. low, medium, high or acute).

In one or more exemplary monitor devices, the processor is configured to apply a processing scheme, the first interface is connected to the processor and the memory, and the first interface is configured for collecting ostomy data from the base plate coupled to the first interface. The ostomy data may comprise one or more, such as all, of first ostomy data from a first electrode pair of the base plate, second ostomy data from a second electrode pair of the base plate, and third ostomy data from a third electrode pair of the base plate. A second interface is connected to the processor. To apply a processing scheme may comprise one or more of obtain first parameter data based on the first ostomy data; obtain second parameter data based on the second ostomy data; and obtain third parameter data based on the third ostomy data. To apply a processing scheme may comprise determine an operating state of the base plate of the ostomy appliance based on one or more, such as all, of the first parameter data, the second parameter data and the third parameter data. The operating state may be indicative of a degree of radial erosion of the base plate, such as of the first adhesive layer, and/or an acute leakage risk for the ostomy appliance. The monitor device is configured to, in accordance with a determination that the operating state is a first operating state, transmit a first monitor signal comprising monitor data indicative of the first operating state of the base plate via the second interface; and/or in accordance with a determination that the operating state is a second operating state, transmit a second monitor signal comprising monitor data indicative of the second operating state of the base plate via the second interface.

In one or more exemplary monitor devices, the first operating state of the base plate corresponds to a situation wherein the first adhesive layer of the base plate has experienced a first degree of radial erosion, e.g. the first adhesive layer is eroded to a first radial distance of the first electrode pair but not to a second radial distance of the second electrode pair.

In one or more exemplary monitor devices, the second operating state of the base plate corresponds to a situation wherein the first adhesive layer of the base plate has experienced a second degree of radial erosion, e.g. the first adhesive layer is eroded to the second radial distance of the second electrode pair but not to a third radial distance of the third electrode pair.

To obtain first parameter data based on the first ostomy data may comprise determining one or more first parameters based on the first ostomy data. To obtain second parameter data based on the second ostomy data may comprise determining one or more second parameters based on the second ostomy data. To obtain third parameter data based on the third ostomy data may comprise determining one or more third parameters based on the third ostomy data. In one or more exemplary monitor devices, determination of an operating state may be based on one or more first parameters, such as first primary parameter and/or first secondary parameter of first parameter data. In one or more exemplary monitor devices, determination of an operating state may be based on one or more second parameters, such as second primary parameter and/or second secondary parameter of the second parameter data. In one or more exemplary monitor devices, determination of an operating state may be based on one or more third parameters, such as third primary parameter and/or third secondary parameter of the third parameter data. In one or more exemplary monitor devices, determination of an operating state may be based on one or more fourth parameters, such as fourth primary parameter and/or fourth secondary parameter of the fourth parameter data.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped.

The monitor device comprises a first interface connected to the processor. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and//or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device may comprise a sensor unit with one or more sensors. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively. The processor may be configured to transmit a monitor signal, such as third monitor signal and/or fourth monitor signal via the loudspeaker. The processor may be configured to transmit a monitor signal, such as one or more, e.g. all, of first monitor signal, second monitor signal, third monitor signal, fourth monitor signal and default monitor signal, as a wireless monitor signal via the antenna and the wireless transceiver.

In one or more exemplary ostomy systems, the monitor device forms an integrated part of the ostomy appliance, e.g. the monitor device may form an integrated part of a base plate of the ostomy appliance.

The first parameter data, the second parameter data, and the third parameter data may be indicative of resistance between the first electrode pair, the second electrode pair, and the third electrode pair, respectively. The first parameter data, the second parameter data, and the third parameter data may be indicative of voltage between the first electrode pair, the second electrode pair, and the third electrode pair, respectively (and thus indicative of resistance). The first parameter data, the second parameter data, and the third parameter data may be indicative of current between the first electrode pair, the second electrode pair, and the third electrode pair, respectively (and thus indicative of resistance).

The first parameter data, the second parameter data, and the third parameter data may be indicative of resistance between the first electrode pair, the second electrode pair, and the third electrode pair, respectively.

The first parameter data, the second parameter data, and the third parameter data may be indicative of a rate of change in resistance between the first electrode pair, the second electrode pair, and the third electrode pair, respectively. In one or more exemplary monitor devices, the first parameter data, the second parameter data, and the third parameter data may be indicative of a rate of change in voltage between the first electrode pair, the second electrode pair, and the third electrode pair, respectively. In one or more exemplary monitor devices, the first parameter data, the second parameter data, and the third parameter data may be indicative of a rate of change in current between the first electrode pair, the second electrode pair, and the third electrode pair, respectively.

To determine an operating state of the base plate of the ostomy appliance may comprise to determine an operating state from a set of operating states. In other words, to determine an operating state may comprise selecting an operating state from a set of predefined operating states. The set of predefined operating states may comprise a number of operating states, such as at least two operating states, at least three operating states, at least four operating states, at least five operating states. The number of operating states may be in the range from four to twenty. In one or more exemplary monitor devices, the number of operating states in the set of predefined operating states. is larger than ten, such as larger than 20 or even larger than 50.

In one or more exemplary monitor devices, the processor is configured to determine an operating state of the base plate if a change criterion is fulfilled. The change criterion may be based on the first parameter data, the second parameter data and/or the third parameter data. The change criterion may be fulfilled if parameter data changes, e.g. if a change in parameter data is larger than a change threshold. Thus, operating state determination may be conditional or dependent on a change in the parameter data, in turn leading to an optimum use of power or battery resources in the monitor device, since operating state determination is only performed when there may be a change in the operating state as a consequence of the change in parameter data.

In one or more exemplary monitor devices, to determine an operating state of the base plate is based on a first criteria set based on the first parameter data and/or the second parameter data, wherein the operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary monitor devices, to determine an operating state of the base plate may be based on a first threshold set comprising one or a plurality of first threshold values. The first threshold set may comprise one or a plurality of threshold values, e.g. to be applied in the first criteria set. The first threshold set may comprise a first primary threshold value. The first threshold set may comprise a first secondary threshold value. The first threshold set may comprise a first tertiary threshold value.

The first criteria set may be given by or at least may comprise:

($P\_1\_1 < TH\_1\_1$),
($P\_2\_1 > TH\_1\_2$), and
($P\_3\_1 > TH\_1\_3$), wherein $P\_1\_1$ is a first primary parameter based on the first parameter data, $TH\_1\_1$ is a first primary threshold value, $P\_2\_1$ is a second primary parameter based on the second parameter data, $TH\_1\_2$ is a first secondary threshold value, $P\_3\_1$ is a third primary parameter based on the third parameter data, and $TH\_1\_3$ is a first tertiary threshold value, and wherein the first operating state is indicative of low degree of radial erosion on the base plate. The first threshold values ($TH\_1\_1$, $TH\_1\_2$ and $TH\_1\_3$) may be the same or different, e.g. depending on the electrode configuration of the base plate. The first tertiary criterion ($P\_3\_1 < TH\_1\_3$) may be omitted in the first criteria set. The first operating state, e.g. indicative of low degree of radial erosion on the base plate may be indicative of a radial progression of moisture to the first electrode pair (but not to the second electrode pair and not to the third electrode pair) which corresponds to e.g. an un-alarming and/or normal radial progression of moisture.

In one or more exemplary embodiments, when the first parameter data, the second parameter data and the third parameter data are each respectively indicative of resistance between the first electrode pair, the second electrode pair and the third electrode pair respectively, the first threshold values ($TH\_1\_1$, $TH\_1\_2$ and $TH\_1\_3$) may correspond to first resistance threshold values. In one or more exemplary embodiments, the first primary threshold value $TH\_1\_1$ may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. In one or more exemplary embodiments, the first secondary threshold value $TH\_1\_2$ may correspond to the upper resistance threshold value. In one or more exemplary embodiments, the first tertiary threshold value $TH\_1\_3$ may correspond to the upper resistance threshold value.

The first primary parameter $P\_1\_1$ may be indicative of the resistance between the first electrode pair (first electrode and first electrode part of the ground electrode) of the base plate. The first parameter data may comprise a first secondary parameter which may be derived from the first primary parameter, and/or a first tertiary parameter, which may be derived from the first primary parameter. A first secondary parameter $P\_1\_2$ may comprise or be a gradient derived from the first primary parameter. In one or more embodiments, a first primary parameter $P\_1\_1$ may be indicative of a voltage between the first electrode pair (first electrode and first electrode part of the ground electrode) of the base plate.

In one or more exemplary embodiments, when the first parameter data, the second parameter data and the third parameter data are each respectively indicative of voltage between the first electrode pair, the second electrode pair and the third electrode pair respectively, the first threshold values ($TH\_1\_1$, $TH\_1\_2$ and $TH\_1\_3$) may correspond to first voltage threshold values. In one or more exemplary embodiments, the first primary threshold value $TH\_1\_1$ may correspond to an upper voltage threshold value. An upper voltage threshold value may be set to a value less than 5 Volts, such as 3 Volts, such as 2, 86 Volts. In one or more exemplary embodiments, the first secondary threshold value $TH\_1\_2$ may correspond to the upper voltage threshold value. In one or more exemplary embodiments, the first tertiary threshold value $TH\_1\_3$ may correspond to the upper voltage threshold value.

The first criteria set may comprise e.g.:

($P\_4\_1 > TH\_1\_4$)

wherein $P\_4\_1$ is a fourth primary parameter based on the fourth parameter data and indicative of the resistance, voltage, or current between the fourth electrode pair and $TH\_1\_4$ is a first quaternary threshold value, and wherein the first operating state is indicative of absence of fluid on the proximal side of the first adhesive layer of the base plate of the ostomy appliance. In one or more exemplary embodiments, the first quaternary threshold value $TH\_1\_4$ may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms.

In one or more exemplary embodiments, the following additional criterion may be determined:

($P\_1\_1 < TH\_low$), wherein $P\_1\_1$ is a first primary parameter based on the first parameter data, $TH\_low$ is a threshold value corresponding to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. This is indicative of a saturation of the first electrode pair by the moisture detected and there are no further changes expected by the first primary parameter. Moisture is likely to continue its progression.

In one or more exemplary embodiments, the following additional criterion may be determined:

($P\_2\_1 < TH\_low$), wherein $P\_2\_1$ is a second primary parameter based on the second parameter data, $TH\_low$ is a threshold value corresponding to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. This is indicative of a saturation of the second electrode pair by the moisture detected and there are no further changes expected by the second primary parameter. Moisture is likely to continue its progression.

In one or more exemplary embodiments, the following additional criterion may be determined:

($P\_3\_1 > TH\_low$), $P\_3\_1$ is a third primary parameter based on the third parameter data, and $TH\_low$ is a threshold value corresponding to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. This is indicative of a saturation of the third electrode pair by the moisture detected and there are no further changes expected by the second primary parameter. Moisture is likely to continue its progression.

In one or more exemplary embodiments, one or more criteria of a criteria set, e.g. one or more first criteria of the first criteria set and/or one or more second criteria of the second criteria set, may be based on timing information or one or more delay parameters based on the parameter data. In one or more exemplary embodiments, one or more delay parameters or time differences related to different parameter data, e.g. related to the first parameter data and the second parameter data, are determined.

In one or more exemplary embodiments, one or more first criteria of the first criteria set may be based on timing information (e.g. one or more delay parameters of the parameter data and/or one or more times where a parameter crosses a threshold).

In one or more exemplary embodiments, the timing information may comprise a time difference $D\_1\_2\_1$ between a time T1 where $P\_1\_1$ crosses a threshold, such as $TH\_1\_1$, and a time T2 where $P\_2\_1$ crosses a threshold, such as $TH\_1\_2$. Thus, delay parameter or time difference $D\_1\_2\_1$ may be given as $D\_1\_2\_1 = T2 - T1$.

In one or more exemplary embodiments, the timing information, e.g. used in the first criteria set, may comprise a time difference $D\_2\_3\_1$ between a time T2 where $P\_2\_1$ crosses a threshold, such as $TH\_1\_2$, and a time T3 where $P\_3\_1$ crosses a threshold, such as $TH\_1\_3$. Thus, delay parameter or time difference $D\_2\_3\_1$ may be given as $D\_2\_3\_1 = T3 - T2$.

In one or more exemplary embodiments, one or more criteria sets, such as the third criteria set and/or the second criteria set, may comprise any of:

$D\_1\_2\_1 > Z$ $D\_2\_3\_1 > Z$ wherein Z is a time difference constant characterizing the progression of moisture (e.g. 3 h, e.g. 2). Different time difference constants may be employed in different criteria sets/for different time delays.

In one or more exemplary embodiments, one or more criteria sets, such as the second criteria set and/or the third criteria set may comprise any of:

$D\_1\_2\_1 > Z$ wherein Z is a time difference constant characterizing the progression of moisture (e.g. 3 h, e.g. 2).

The second primary parameter may be indicative of the resistance between the second electrode pair (second electrode and second electrode part of the ground electrode) of the base plate. The second parameter data may comprise a second secondary parameter, and/or a second tertiary parameter, which may be derived from the second primary parameter. A second secondary parameter may be indicative of a voltage between the second electrode pair (second electrode and second electrode part of the ground electrode) of the base plate.

The third primary parameter may be indicative of resistance between the third electrode pair (third electrode and third electrode part of the ground electrode) of the base plate. The third parameter data may comprise a third secondary parameter, and/or a third tertiary parameter, which may be derived from the third primary parameter. A third secondary parameter may be indicative of a voltage between the second electrode pair (second electrode and second electrode part of the ground electrode) of the base plate.

In one or more exemplary monitor devices, to determine an operating state of the base plate is based on a second criteria set based on the second parameter data and/or the third parameter data, wherein the operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary monitor devices, to determine an operating state of the base plate is based on a second threshold set comprising one or a plurality of second threshold values. The second threshold set may comprise one or a plurality of threshold values, e.g. to be applied in the second criteria set. The second threshold set may comprise a second primary threshold value. The second threshold set may comprise a second secondary threshold value. The second threshold set may comprise a second tertiary threshold value.

The second criteria set may be given by or at least may comprise:

(P_1_1<TH_2_1),
(P_2_1<TH_2_2), and
(P_3_1>TH_2_3)

wherein P_1_1 is a first primary parameter based on the first parameter data and indicative of the resistance between the first electrode pair, TH_2_1 is a second primary threshold value, P_2_1 is a second primary parameter based on the second parameter data and indicative of the resistance between the second electrode pair, TH_2_2 is a second secondary threshold value, P_3_1 is a third primary parameter based on the third parameter data and indicative of the resistance between the third electrode pair, TH_2_3 is a second tertiary threshold value, and wherein the second operating state is indicative of medium degree of radial erosion on the base plate. The second threshold values (TH_2_1, TH_2_2 and TH_2_3) may be the same or different, e.g. depending on the electrode configuration of the base plate. The second primary criterion (P_1_1<TH_2_1) and/or the second tertiary criterion (P_3_1>TH_2_3) may be omitted in the second criteria set.

The second operating state indicative of medium degree of radial erosion on the base plate may be indicative of a radial progression of moisture to the first electrode pair and the second electrode pair (and not the third electrode pair). The second operating state indicative of medium degree of radial erosion on the base plate may be indicative of a radial progression of moisture to the first electrode pair and to the second electrode pair.

In one or more exemplary embodiments, when the first parameter data, the second parameter data and the third parameter data are each respectively indicative of resistance between the first electrode pair, the second electrode pair and the third electrode pair respectively, the second threshold values (TH_2_1, TH_2_2 and TH_2_3) may correspond to second resistance threshold values. In one or more exemplary embodiments, the second primary threshold value TH_2_1 may correspond to an upper resistance threshold value. An upper resistance threshold value may be set to a value which is less than 30 Mega-Ohms, such as 25 Mega-Ohms, such as 20.5 Mega Mega-Ohms, such as 20.4 Mega-Ohms. In one or more exemplary embodiments, the second secondary threshold value TH_2_2 may correspond to the upper resistance threshold. In one or more exemplary embodiments, the second tertiary threshold value TH_2_3 may correspond to the upper resistance threshold value. In one or more exemplary embodiments, the second primary threshold value TH_2_1 may correspond to a medium resistance threshold value. A medium resistance threshold value may be set to a value less than 10 Mega-Ohms, such as 5 Mega-Ohms, such as 3 Mega-Ohms, such as 2 Mega-Ohms, such as 1 Mega-Ohms.

In one or more exemplary embodiments, when the first parameter data, the second parameter data and the third parameter data are each respectively indicative of voltage between the first electrode pair, the second electrode pair and the third electrode pair respectively, the second threshold values (TH_2_1, TH_2_2 and TH_2_3) may correspond to second voltage threshold values. In one or more exemplary embodiments, the second primary threshold value TH_2_1 may correspond to an upper voltage threshold value. An upper voltage threshold value may be set to a value less than 5 Volts, such as 3 Volts, such as 2.86 Volts. In one or more exemplary embodiments, the second secondary threshold value TH_2_2 may correspond to the upper voltage threshold value. In one or more exemplary embodiments, the second tertiary threshold value TH_2_3 may correspond to the upper voltage threshold value. In one or more exemplary embodiments, the second primary threshold value TH_2_1 may correspond to a medium voltage threshold value. A medium resistance threshold value may be set to a value less than 10 Mega-Ohms, such as 5 Mega-Ohms, such as 3 Mega-Ohms, such as 2 Mega-Ohms, such as 1 Mega-Ohms.

In one or more exemplary embodiments, the second criteria set may comprise any of:

D_1_2_1>Z wherein Z is a time difference constant characterizing the progression of moisture (e.g. 3 h, e.g. 2 h).

In one or more exemplary monitor devices, to determine an operating state of the base plate is based on a default criteria set based on the first parameter data, wherein the operating state is determined to be the default operating state if the default criteria set is satisfied, and in accordance with a determination that the operating state is the default operating state, transmit a default monitor signal comprising monitor data indicative of the default operating state of the ostomy appliance.

The default criteria set may be given by or at least may comprise:

(P_1_1>TH_D_1),
(P_2_1>TH_D_2), and
(P_3_1>TH_D_3)

wherein P_1_1 is a first primary parameter based on the first parameter data and indicative of the resistance between the first electrode pair, TH_D_1 is a default primary threshold value, P_2_1 is a second primary parameter based on the second parameter data and indicative of the resistance between the second electrode pair, TH_D_2 is a default secondary threshold value, P_3_1 is a third primary parameter based on the third parameter data and indicative of the resistance between the third electrode pair, TH_D_3 is a default tertiary threshold value, and wherein the default operating state is indicative of very low or no degree of radial erosion on the base plate. The default threshold values (TH_D_1, TH_D_2 and TH_D_3) may be the same or different, e.g. depending on the electrode configuration of the base plate. In one or more exemplary embodiments, when the first parameter data, the second parameter data and the third parameter data are each respectively indicative of resistance between the first electrode pair, the second electrode pair and the third electrode pair respectively, the default threshold values (TH_D_1, TH_D_2 and TH_D_3) may correspond to default resistance threshold values. In one or more exemplary embodiments, the second primary threshold value TH_D_1 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. In one or more exemplary embodiments, the default secondary threshold value TH_D_2 may correspond to the upper resistance threshold. In one or more exemplary embodiments, the default tertiary threshold value TH_D_3 may correspond to the upper resistance threshold value.

In one or more exemplary embodiments, when the first parameter data, the second parameter data and the third parameter data are each respectively indicative of voltage between the first electrode pair, the second electrode pair and the third electrode pair respectively, the default threshold values (TH_D_1, TH_D_2 and TH_D_3) may correspond to default voltage threshold values. In one or more exemplary embodiments, the default primary threshold value TH_D_1 may correspond to an upper voltage threshold value. An upper voltage threshold value may be set to a value less than 5 Volts, such as 3 Volts, such as 2.86 Volts. In one or more exemplary embodiments, the default secondary threshold value TH_D_2 may correspond to the upper voltage threshold value. In one or more exemplary embodiments, the default tertiary threshold value TH_D_3 may correspond to the upper voltage threshold value.

In one or more exemplary monitor devices, to determine an operating state of the base plate is based on a third criteria set based on the third parameter data, wherein the operating state is determined to be the third operating state if the third criteria set is satisfied, and in accordance with a determination that the operating state is the third operating state, transmit a third monitor signal comprising monitor data indicative of the third operating state of the ostomy appliance.

In one or more exemplary monitor devices, the third operating state of the base plate corresponds to a situation wherein the first adhesive layer of the base plate has experienced a third degree of radial erosion, e.g. the first adhesive layer is eroded to the third radial distance of the third electrode pair.

The third criteria set may be given by or at least may comprise:
(P_1_1<TH_3_1),
(P_2_1<TH_3_2), and
(P_3_1<TH_3_3)
wherein P_1_1 is a first primary parameter based on the first parameter data and indicative of the resistance between the first electrode pair, TH_3_1 is a third primary threshold value, P_2_1 is a second primary parameter based on the second parameter data and indicative of the resistance between the second electrode pair, TH_3_2 is a third secondary threshold value, P_3_1 is a third primary parameter based on the third parameter data and indicative of the resistance between the third electrode pair, TH_3_3 is a third tertiary threshold value, and wherein the third operating state is indicative of high degree of radial erosion on the base plate. The third threshold values (TH_3_1, TH_3_2 and TH_3_3) may be the same or different, e.g. depending on the electrode configuration of the base plate. The third primary criterion (P_1_1<TH_3_1) and/or the third secondary criterion (P_2_1<TH_3_2) may be omitted in the third criteria set. The third operating state indicative of high degree of radial erosion on the base plate may be indicative of high likelihood of leakage, e.g. on the proximal side of the base plate, e.g. within a time period e.g. within the next 20 minutes. The third operating state may indicate a radial progression of moisture to the first electrode pair, the second electrode pair, and the third electrode pair.

In one or more exemplary embodiments, when the first parameter data, the second parameter data and the third parameter data are each respectively indicative of resistance between the first electrode pair, the second electrode pair and the third electrode pair respectively, the third threshold values (TH_3_1, TH_3_2 and TH_3_3) may correspond to third resistance threshold values. In one or more exemplary embodiments, the third primary threshold value TH_3_1 may correspond to an upper resistance threshold value. In one or more exemplary embodiments, the third secondary threshold value TH_3_2 may correspond to an upper resistance threshold value. In one or more exemplary embodiments, the third tertiary threshold value TH_3_3 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms.

In one or more exemplary embodiments, the third primary threshold value TH_3_1 may correspond to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. In one or more exemplary embodiments, the third secondary threshold value TH_3_2 may correspond to a medium resistance threshold. A medium resistance threshold value may be set to a value less than 10 Mega-Ohms, such as 5 Mega-Ohms, such as 3 Mega-Ohms, such as 2 Mega-Ohms, such as 1 Mega-Ohms. In one or more exemplary embodiments, the third tertiary threshold value TH_3_3 may correspond to the upper resistance threshold. An upper resistance threshold value may be set to a value which is less than 30 Mega-Ohms, such as 25 Mega-Ohms, such as 20.5 Mega Mega-Ohms, such as 20.4 Mega-Ohms.

In one or more exemplary embodiments, when the first parameter data, the second parameter data and the third parameter data are each respectively indicative of voltage between the first electrode pair, the second electrode pair and the third electrode pair respectively, the third threshold values (TH_3_1, TH_3_2 and TH_3_3) may correspond to third voltage threshold values. In one or more exemplary embodiments, the third primary threshold value TH_3_1 may correspond to an upper voltage threshold value. In one or more exemplary embodiments, the third secondary threshold value TH_3_2 may correspond to an upper voltage threshold value. In one or more exemplary embodiments, the second tertiary threshold value TH_2_3 may correspond to the upper voltage threshold value.

In one or more exemplary embodiments, the third primary threshold value TH_3_1 may correspond to a lower voltage threshold value. In one or more exemplary embodiments, a lower voltage threshold value may be set to a value which is less than 1 Volt, such as 0.5 Volt, such as 0.25 Volts, such as 0.22 Volts. In one or more exemplary embodiments, the third secondary threshold value TH_3_2 may correspond to a medium voltage threshold value. A medium voltage threshold value may be set to a value less than 2 Volts, such as 1.5 Volts. In one or more exemplary embodiments, the second tertiary threshold value TH_2_3 may correspond to the upper voltage threshold value.

In one or more exemplary embodiments, the third criteria set may comprise any of:
D_1_2_1<Z
D_2_3_1<Z
Wherein Z is a time difference constant characterizing the progression of moisture (e.g. 3h, e.g. 2 h), a time difference D_1_2_1 between a time T1 where P_1_1 crosses TH_1_1 and a time T2 where P_2_1 crosses TH_1_2, and a time difference D_2_3_1 between a time T2 where P_2_1 crosses TH_1_2 and a time T3 where P_3_1 crosses TH_1_3. In one or more exemplary monitor devices, the ostomy data comprises fourth ostomy data from a fourth electrode pair of the base plate. To apply a processing scheme may comprise to obtain fourth parameter data based on the fourth ostomy data, and determine an operating state of the base plate of the ostomy appliance based on the fourth parameter data. The monitor device may be configured to, in accordance with a determination that the operating state is a fourth operating state, transmit a fourth monitor signal comprising monitor data indicative of the fourth operating state of the ostomy appliance.

In one or more exemplary monitor devices, the fourth operating state of the base plate corresponds to a situation, wherein the fourth electrode pair detects fluid, such as output, between the proximal surface of first adhesive layer and the skin of the user at a fourth radial distance, and thus there is a high risk of leakage from the ostomy appliance in the fourth operating state.

The fourth criteria set may be given by or at least may comprise:

($P\_4\_1 < TH\_4\_4$)

wherein $P\_4\_1$ is a fourth primary parameter based on the fourth parameter data and indicative of the resistance between the fourth electrode pair and $TH\_4\_4$ is a fourth quaternary threshold value, and wherein the fourth operating state is indicative of high risk of leakage from the ostomy appliance.

In one or more exemplary embodiments, the fourth quaternary threshold value $TH\_4\_4$ may correspond to an upper resistance threshold value.

In one or more exemplary monitor devices, a fifth operating state of the base plate corresponds to a situation, wherein the fourth electrode pair detects fluid, such as sweat, between the proximal surface of first adhesive layer and the skin of the user at a fourth radial distance, and thus there is a no leakage from the ostomy appliance in the fifth operating state.

The fifth operating state may be determined in accordance with a determination that one or more fifth criterion of a fifth criteria set are satisfied by fourth parameter data.

The fifth criteria set may be given by or at least may comprise:

($P\_4\_1 < TH\_5\_1$)
($P\_4\_2 < TH\_5\_2$)
($P\_4\_3 < TH\_5\_3$)
($\nabla P\_4\_1 < V$)
($\nabla P\_4\_2 < V$) and
($\nabla P\_4 P\_3 < V$)

Wherein $P\_4\_1$ is a fourth primary parameter based on the fourth parameter data and indicative of the resistance between the fourth electrode pair, $P\_4\_2$ is a fourth secondary parameter based on the fourth parameter data and indicative of the resistance between the fourth electrode and the fifth electrode, $P\_4\_3$ is a fourth tertiary parameter based on the fourth parameter data and indicative of the resistance between the fifth electrode pair and $TH\_5\_1$ is a fifth primary threshold value, $TH\_5\_2$ is a fifth secondary threshold value $TH\_5\_3$ is a fifth tertiary threshold value and $\nabla P\_4\_1$ is gradient of $P\_4\_1$, $\nabla P\_4\_2$ is gradient of $P\_4\_2$, $\nabla P\_4\_3$ is gradient of $P\_4\_3$, and V is a gradient limit (e.g. 80%). In one or more exemplary embodiments, the fifth primary threshold value $TH\_5\_1$ may correspond to an upper resistance threshold value. In one or more exemplary embodiments, $TH\_5\_2$ may correspond to an upper resistance threshold value. n one or more exemplary embodiments, $TH\_5\_3$ may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. The fifth operating state may refer to presence of sweat detected by the fourth parameter data indicating moisture detected omnidirectionally from the stomal opening and uniformally.

In one or more exemplary monitor devices, a sixth operating state of the base plate corresponds to a situation, wherein the fourth electrode pair detects fluid, such as output, between the proximal surface of first adhesive layer and the skin of the user at a fourth radial distance, and thus there is a sudden leakage from the ostomy appliance in the sixth operating state.

The sixth operating state may be determined in accordance with a determination that one or more sixth criterion of a sixth criteria set are satisfied by the fourth parameter data.

The sixth criteria set may comprise a sixth primary criterion, wherein the sixth primary criterion may comprise:

($P\_4\_1 < TH\_6\_1$) and
($\nabla P\_4\_1 > V$)

The sixth criteria set may comprise a sixth secondary criterion, wherein the sixth secondary criterion may comprise:

($P\_4\_2 < TH\_6\_2$) and
($\nabla P\_4\_2 > V$)

The sixth criteria set may comprise a sixth tertiary criterion, wherein the sixth tertiary criterion may comprise:

($P\_4\_3 < TH\_6\_3$) and
($\nabla P\_4\_3 > V$)

$P\_4\_1$ is a fourth primary parameter based on the fourth parameter data and indicative of the resistance between the fourth electrode pair, $P\_4\_2$ is a fourth secondary parameter indicative of the resistance between the fourth electrode and the fifth electrode, $P\_4\_3$ is a fourth tertiary parameter indicative of the resistance between the fifth electrode pair (fifth electrode and ground electrode) and $TH\_6\_1$ is a sixth primary threshold value, $TH\_6\_2$ is a sixth secondary threshold value $TH\_6\_3$ is a sixth tertiary threshold value, and $\nabla P\_4\_1$ is gradient of $P\_4\_1$, $\nabla P\_4\_2$ is gradient of $P\_4\_2$, $\nabla P\_4\_3$ is gradient of $P\_4\_3$, and V is a gradient limit (e.g. 80%). In one or more exemplary embodiments, the sixth primary threshold value $TH\_6\_1$ may correspond to an upper resistance threshold value. In one or more exemplary embodiments, $TH\_6\_2$ may correspond to an upper resistance threshold value. In one or more exemplary embodiments, $TH\_6\_3$ may correspond to an upper resistance threshold value. An upper resistance threshold value may be set to a value which is less than 30 Mega-Ohms, such as 25 Mega-Ohms, such as 20.5 Mega Mega-Ohms, such as 20.4 Mega-Ohms. The sixth operating state may refer to presence of output detected by the fourth parameter data indicating a sudden leak, e.g. a developing leak. In one or more exemplary embodiments, when the time T is below X minutes from the placement of the base plate, where X is between 5 to 60 minutes, and when any of $P\_1\_1$, $P\_2\_1$, $P\_3\_1$ in average over T are below a default threshold value corresponding to an upper resistance threshold value, this indicates that any of the first electrode pair, the second electrode pair, and the third electrode pair is cut (e.g. cut by the user when preparing the base plate for placement around the stoma). In one or more exemplary embodiments, when the time T is below X minutes from the placement of the base plate, where X is between 5 to 60 minutes, and when any of $P\_4\_1$, $P\_4\_2$, $P\_4\_3$ in average over T are below a default threshold value corresponding to an upper resistance threshold value, this indicates an instant leakage, e.g. presence of output on the proximal side.

In one or more exemplary embodiments, any of the first criteria set, the second criteria set, the third criteria set, the fourth criteria set, the default criteria set, the fifth criteria set, the sixth criteria set may be used to define one or more further criteria sets, and thereby to determine one or more operating states.

In one or more exemplary embodiments, different criteria sets may be used to determine the same operating state.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and//or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device may comprise a sensor unit with one or more sensor. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively.

In one or more exemplary ostomy systems, the monitor device forms an integrated part of the ostomy appliance, e.g. the monitor device may form an integrated part of a base plate of the ostomy appliance.

The ostomy system may comprise a docking station forming an accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

The present disclosure includes accessory devices, tools and methods for placing an ostomy appliance on a user. A method for operating an accessory device is disclosed to guide the placement of an ostomy appliance on a user having a stoma. The method may be for guiding or assisting placement of an ostomy appliance on a user having a stoma. The method is performed by an accessory device. The accessory device may include a camera, image processor, a memory and a display device. The method includes capturing an image or a sequence of images of the user applying the ostomy appliance to the user's body, processing the captured image or sequence of images, including: identifying a location of the stoma in one or more of the captured image or sequence of images, identifying a location of the ostomy appliance in one or more of the captured image or sequence of images, and generating location indicia representative of the location of the ostomy appliance with respect to the stoma in one or more of the captured image or sequence of images. Identifying a location of the stoma and/or identifying a location of the ostomy appliance may be performed using machine learning. The location indicia can include a stoma location representation and an appliance location representation. The stoma location representation may represent a desired location of the ostomy appliance, and the appliance location representation may represent a current location of the ostomy appliance. The method further includes providing a visual display including the location indicia associated with one or more of the captured image or sequence of images.

Generating the location indicia may include generating a stoma location representation, and generating an appliance location representation. Providing the visual display can include providing a visual display including the stoma location representation and the appliance location representation. The stoma location representation can be an actual location of an actual stoma when it is visible in the captured image or sequence of the images. When the actual stoma is hidden or obstructed by the ostomy appliance (e.g. an ostomy bag), the stoma location representation can be a calculated location of a virtual stoma. Generating and displaying the stoma location representation can include generating and displaying a graphical simulation of the stoma. The graphical simulation of the stoma may be a simulated virtual display object (e.g., a user interface object) representative of the stoma. The simulated virtual display object can be displayed on the visual display of the display device. Generating and displaying the appliance location representation can include generating and displaying a graphical simulation of the ostomy appliance. Generating and displaying the appliance location representation can include generating and displaying an image of at least a portion of the actual ostomy appliance from one or more of the captured image or sequence of images.

Generating the location indicia can include generating a quality indicator representative of the position of the ostomy appliance with respect to a desired position with respect to the stoma. Providing a visual display can include providing a visual display of the quality indicator (e.g., displaying a user interface comprising a user interface object representative of the quality indicator).

A user interface refers herein to a graphical representation comprising a collection of user interface objects. A user interface comprises one or more user interface objects. A user interface may be referred to as a user interface screen.

A user interface object refers herein to a graphical representation of an object that is displayed on the display of the accessory device. The user interface object may be user-interactive, or selectable by a user input. For example, an image (e.g., icon), a button, and text (e.g., hyperlink) each optionally constitute a user interface object. The user interface object may form part of a widget. A widget may be seen as a mini-application that may be used by the user, and created by the user. A user interface object may comprise a prompt, application launch icon, and/or an action menu. An input, such as first input and/or second input, may comprise a touch (e.g. a tap, a force touch, a long press), a and/or movement of contact (e.g. a swipe gesture, e.g. for toggling). The movement on contact may be detected by a touch sensitive surface, e.g. on a display of an accessory device. Thus, the display may be a touch sensitive display. An input, such as first input and/or second input, may comprise a lift off. An input, such as first input and/or second input, may comprise a touch and a movement followed by a lift off.

The display of the accessory device may be configured to detect touch (e.g. the display is a touch-sensitive display), the input comprises a contact on the touch sensitive display. A touch-sensitive display provides an input interface and an output interface between the accessory device and a user. A processor of the accessory device may be configured to receive and/or send electrical signals from/to touch-sensitive display. A touch-sensitive display is configured to display visual output to the user. The visual output optionally includes graphics, text, icons, video, and any combination thereof (collectively termed "graphics"). For example, some or all of the visual output may be seen as corresponding to user-interface objects.

The processor of the accessory device may be configured to display, on the display, one or more user interfaces, such as user interface screens, including a first user interface and/or a second user interface. A user interface may comprise one or more, such as a plurality of user interface objects. For example, the first user interface may comprise a first primary user interface object and/or a first secondary user interface object. A second user interface may comprise a second primary user interface object and/or a second secondary user interface object. A user interface object, such as the first primary user interface object and/or the second primary user interface object, may represent an operating state of the base plate.

Generating the location indicia can include generating a direction indicator representative of a direction the ostomy appliance should be moved to locate the ostomy appliance at a desired position with respect to the stoma. Alternatively or in addition, generating the location indicia can include generating a direction indicator representative of a direction condition/criterion to be fulfilled wherein the direction condition is fulfilled when the ostomy appliance is placed at a desired position with respect to the stoma. Providing the visual display can include providing a visual display of the direction indicator. Alternatively or in addition, providing the visual display can include providing a visual display of the direction indicator representative of a direction condition/criterion to be fulfilled wherein the direction condition is fulfilled when the ostomy appliance is placed at a desired position with respect to the stoma.

Providing a visual display can include providing (e.g. providing visual display of) target indicia representative of a desired position of the ostomy appliance on the user. The method may further include receiving calibration data representative of the location of the stoma on the user's body with respect to a reference indicator on the user's body that is visible in one or more of the captured image or sequence of images. The reference indicator can include a feature of the user's body at a location spaced apart from the stoma, such as a birthmark, mole, blemish, nevus, or any other remarkable symbol disposed on the user's body. The reference indicator may be drawn by the user on the user's body using a writing instrument. Any other suitable marks on the user's body recognizable by the camera are contemplated. Processing the captured image or sequence of images may further include identifying the reference indicator on the user's body. Identifying the location of the stoma can include identifying the location of the stoma as a function of the identified reference indicator on the user's body and the calibration data.

Identifying the location of the ostomy appliance can include identifying a reference indicator on the ostomy appliance. The method can include guiding the placement of an ostomy appliance including a base plate and bag attached to the base plate (e.g., one-part appliance), wherein the base plate is not visible in the captured image or sequence of captured images. Guiding the placement of the ostomy appliance may comprise displaying a virtual stoma on the visual display of the display device in lieu of an actual stoma. The methods disclosed herein may further include methods for guiding the placement of a base plate of a multi-piece ostomy appliance including a bag attachable to the base plate (e.g., two-part appliance, where the bag is attached to the base plate after the base plate is placed on the user's body). Capturing the image or sequence of images, processing the captured image or sequence of images and providing the visual display can be performed by an accessory device including a camera, image processor and display device.

An accessory device configured to provide a fitting process of the ostomy appliance (e.g. to assist or guide a placement of the ostomy appliance on the stoma of the user) is disclosed. The accessory device includes a camera, image processor, display and stored instructions for performing any of the steps of the methods disclosed herein. The accessory device can include a processor, a memory, a camera, an input device, and at least one display device. The memory, camera, input device and display device are operatively and communicably coupled to the processor for transmitting and receiving data. A bus can be used to mutually communicate between various components associated with the accessory device, such as the processor, the memory, the camera, and the input device. The camera captures one or more images and generates image data for subsequent rendering and processing.

Included in the processor is an appliance guidance unit configured to process the image data. The appliance guidance unit identifies a location of the stoma in one or more of the captured image or sequence of images, and also identifies a location of the ostomy appliance in one or more of the captured image or sequence of images. The appliance guidance unit generates location indicia representative of the location of the ostomy appliance with respect to the stoma in one or more of the captured image or sequence of images. The display device provides a visual display including the location indicia associated with one or more of the captured image or sequence of images.

The appliance guidance unit may generate the location indicia that include a stoma location representation and an appliance location representation. The appliance guidance unit can control the visual display to include the stoma location representation and the appliance location representation. The appliance guidance unit can generate and control the visual display to display a graphical simulation of the stoma. Also, the appliance guidance unit can generate and control the visual display (e.g. via the display device) to display a graphical simulation of the ostomy appliance. The appliance guidance unit can generate and control the visual display (e.g. via the display device) to display an image of at least a portion of the actual ostomy appliance from one or more of the captured image or sequence of images.

The appliance guidance unit can generate a quality indicator representative of the position of the ostomy appliance with respect to a desired position with respect to the stoma. The appliance guidance unit can provide instructions to the visual display (e.g. via the display device) for displaying the quality indicator.

The appliance guidance unit can generate a direction indicator representative of a direction the ostomy appliance should be moved to locate the ostomy appliance at a desired position with respect to the stoma. The appliance guidance unit can provide instructions to the visual display (e.g. via the display device) for displaying the direction indicator. The appliance guidance unit can provide target indicia representative of a desired position of the ostomy appliance on the user.

Further included in the accessory device is optionally an appliance calibration unit configured to calculate a location of the stoma based on distance scale information. The appliance guidance unit can receive calibration data representative of the location of the user's stoma from the appliance calibration unit with respect to a reference indicator on the user's body that is visible in one or more of the captured image or sequence of images. The appliance calibration unit can identify the reference indicator on the user's body and also can identify the location of the stoma as a function of the identified reference indicator on the user's body and the calibration data. The appliance calibration unit can identify a reference indicator on the ostomy appliance.

The appliance guidance unit can guide the placement of an ostomy appliance including a base plate and bag attached to the base plate (e.g., one-part appliance). The appliance guidance unit can also guide the placement of a base plate of a multi-piece ostomy appliance including a bag attachable to the base plate (e.g., two-part appliance, where the bag is attached to the base plate after the base plate is placed on the user's body).

One or more computer-readable media have computer-executable instructions embodied thereon. The computer-executable instructions are configured to cause at least one processor, upon being executed by the at least one processor, to perform any of the methods related to the tools and methods for placing an ostomy appliance on a user described above.

FIG. 1 illustrates an exemplary ostomy system. The ostomy system 1 comprises an ostomy appliance 2 including a base plate 4 and an ostomy pouch (not shown). Further, the ostomy system 1 comprises a monitor device 6 and an accessory device 8 (mobile telephone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data to determine monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate 4 has a stomal opening 18 with a stoma center point 19. The size and/or shape of the stomal opening 18 is typically adjusted by the user or nurse before application of the ostomy appliance to accommodate the user's stoma.

Figure 2:
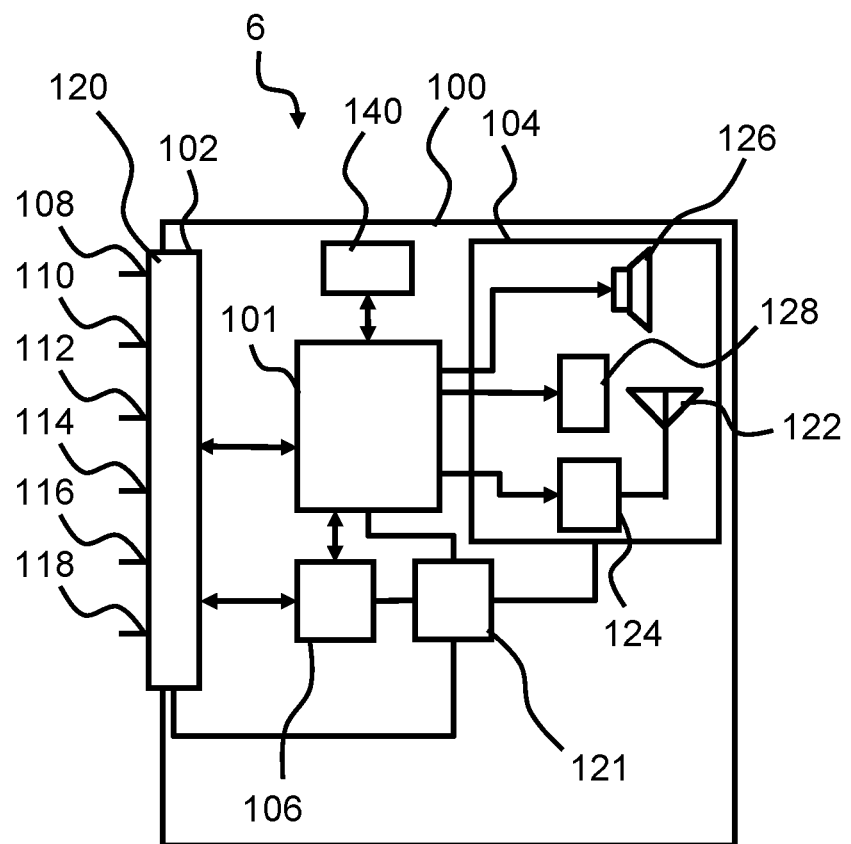
FIG. 2 illustrates an exemplary monitor device of the ostomy system.

The ostomy system 1 optionally comprises a docking station 20 forming an accessory device of the ostomy system 1. The docking station comprises 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes, FIG. 2 is a schematic block diagram of an exemplary monitor device. The monitor device 6 comprises a monitor device housing 100, a processor 101 and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 optionally comprises a sensor unit 140 connected to the processor 101. The sensor unit 140 comprises a temperature sensor for feeding temperature data to the processor and/or a G-sensor or accelerometer for feeding acceleration data to the processor 101.

The processor 101 is configured to apply a processing scheme, and the first interface 102 is configured for collecting ostomy data from the base plate coupled to the first interface, the ostomy data comprising first ostomy data from a first electrode pair of the base plate, second ostomy data from a second electrode pair of the base plate, and third ostomy data from a third electrode pair of the base plate. The ostomy data may be stored in the memory 106 and/or processed in the processor 101 in order to obtain parameter data. The parameter data may be stored in the memory 106. The processor 101 is configured to apply a processing scheme, wherein to apply a processing scheme comprises obtain first parameter data based on the first ostomy data; obtain second parameter data based on the second ostomy data; obtain third parameter data based on the third ostomy data. In other words, the processor 101 is configured to obtain first, second and third parameter data based on respective first, second and third ostomy data. To apply a processing scheme comprises to determine an operating state of the base plate of the ostomy appliance based on one or more, e.g. all, of the first parameter data, the second parameter data and the third parameter data, wherein the operating state is indicative of a degree of radial erosion of the base plate and/or acute leakage risk for the ostomy appliance. The monitor device 6 is configured to, in accordance with a determination that the operating state is a first operating state, transmit a first monitor signal comprising monitor data indicative of the first operating state of the base plate via the second interface; and in accordance with a determination that the operating state is a second operating state, transmit a second monitor signal comprising monitor data indicative of the second operating state of the base plate via the second interface.

The monitor device 100 is configured to obtain ostomy data from the base plate coupled to the first interface 102. The ostomy data may be stored in the memory 106 and/or processed in the processor 101 in order to obtain parameter data based on the ostomy data.

Figure 3:
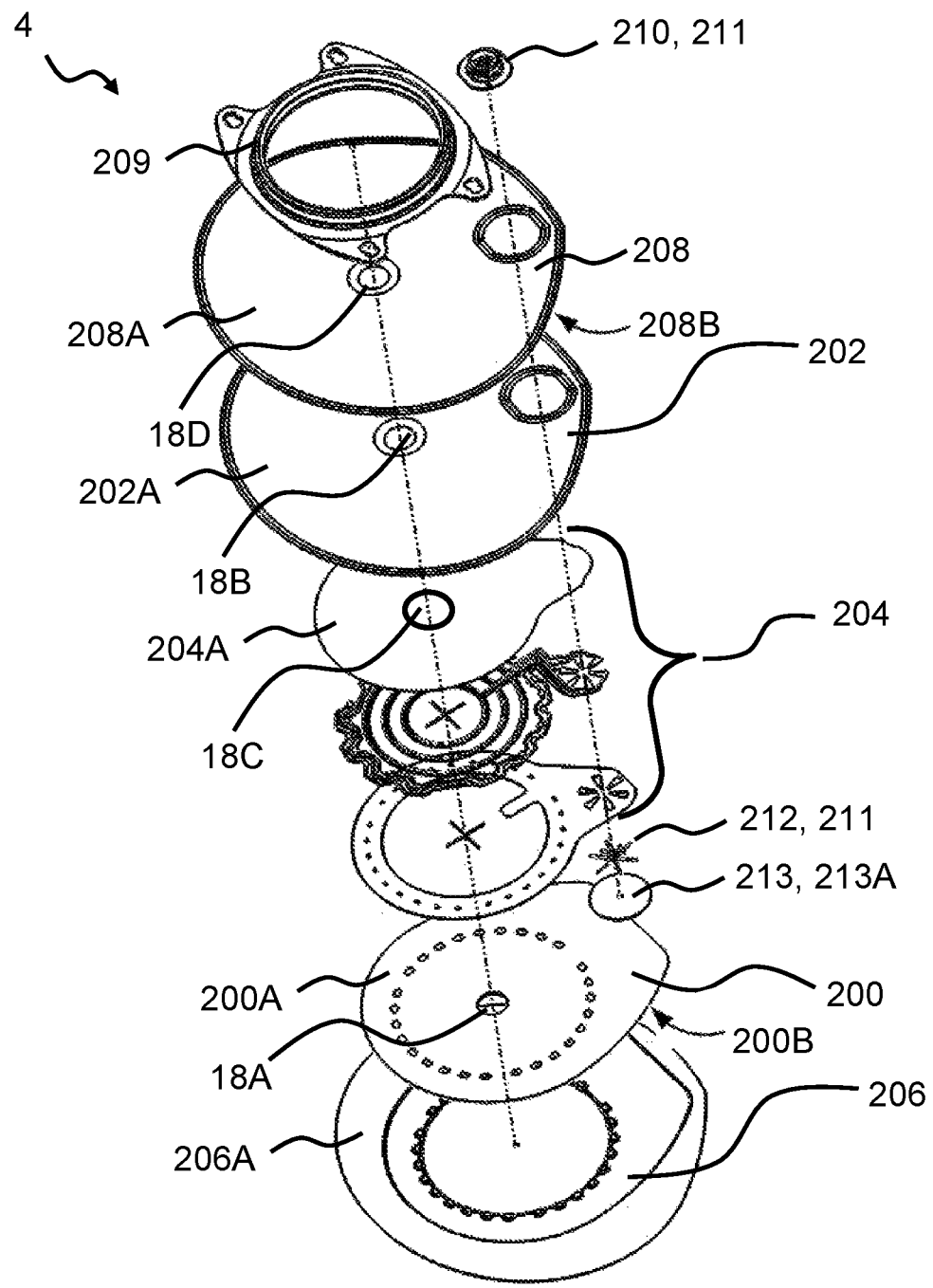
FIG. 3 is an exploded view of a base plate of an ostomy appliance.

FIG. 3 illustrates an exploded view of an exemplary base plate of an ostomy appliance. The base plate 4 comprises a first adhesive layer 200 with a stomal opening 18A. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer. The base plate 4 comprises a plurality of electrodes arranged in an electrode assembly 204. The electrode assembly 204 is arranged between the first adhesive layer 200 and the second adhesive layer 202 with a stomal opening 18B. The electrode assembly 204 comprises a support layer with stomal opening 18C and electrodes formed on a proximal surface of the support layer. The base plate 4 comprises a release liner 206 that is peeled off by the user prior to applying the base plate 4 on the skin. The base plate 4 comprises a top layer 208 with a stomal opening 18D and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the distal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

Figure 4:
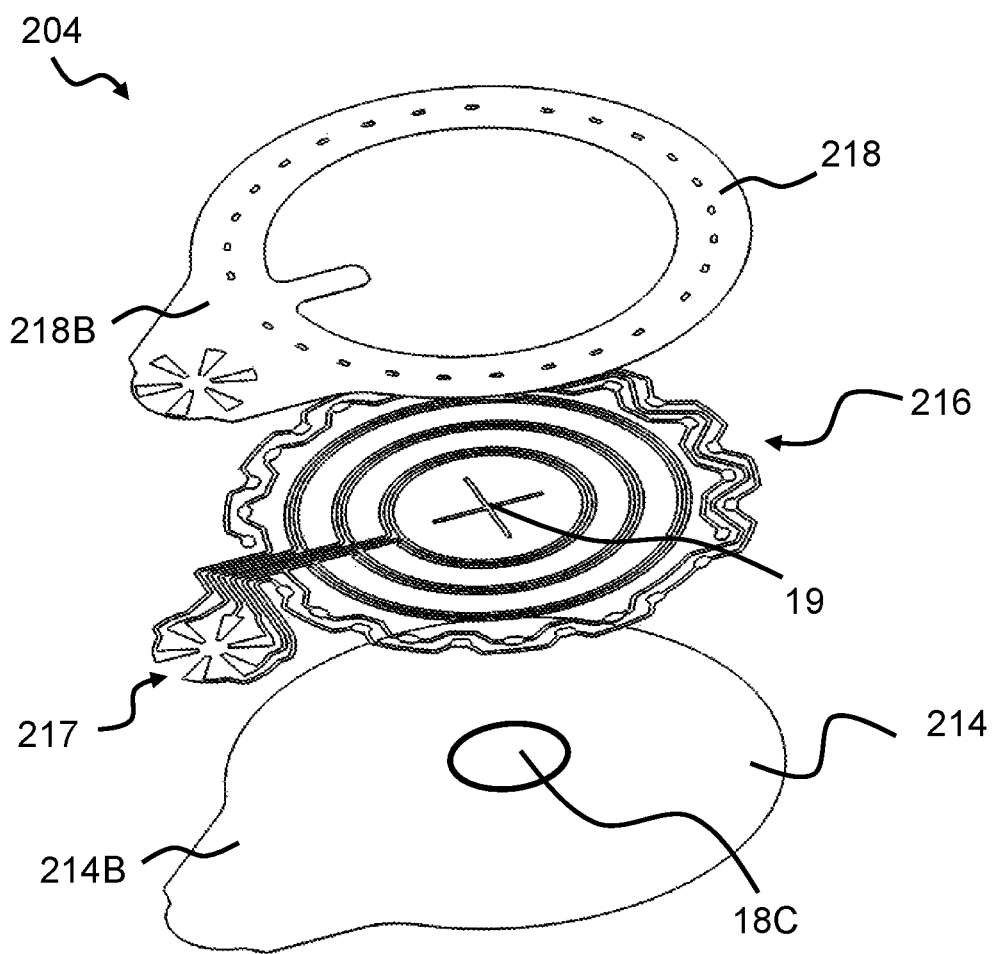
FIG. 4 is an exploded view of an exemplary electrode assembly.

FIG. 4 illustrates an exploded view of an exemplary electrode assembly 204 of a base plate. The electrode assembly 204 has a distal side 204A and a proximal side 204B. The electrode assembly 204 comprises a support layer 214 with proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part 217 for connecting the electrodes 216 to respective terminal elements of the monitor interface. The electrodes 216 are positioned and/or formed on a proximal side 214B of the support layer 214. Further, electrode assembly 204 comprises a masking element 218 with proximal surface 218B and configured to insulate electrode parts of electrodes 216 from the first adhesive layer of the base plate. The masking element 218 covers or overlap with parts of the electrodes 216 when seen in the axial direction.

Figure 5:
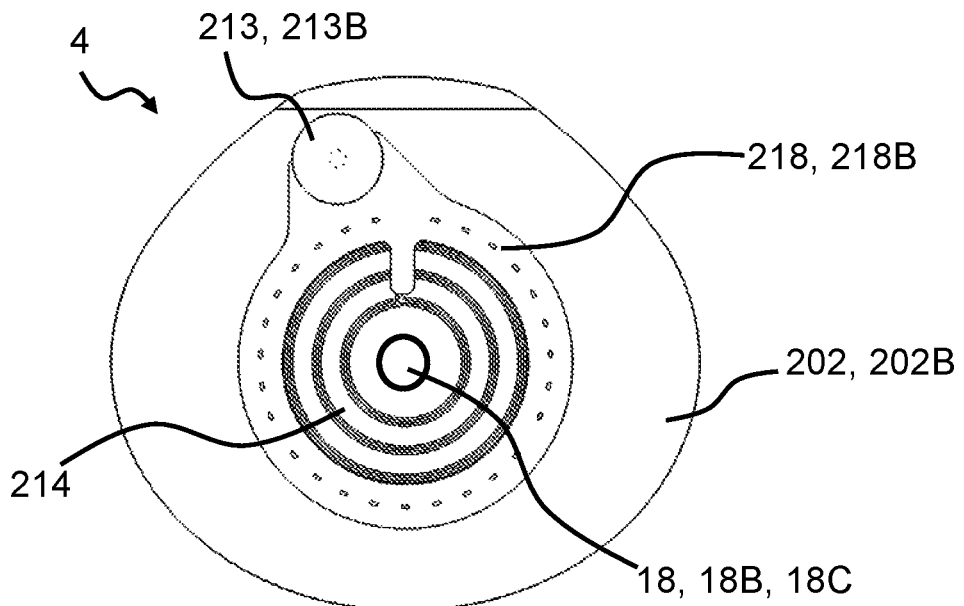
FIG. 5 is a proximal view of parts of a base plate.

FIG. 5 is a proximal view of proximal surfaces of base plate parts of the base plate without the first adhesive layer and the release liner. The base plate 4 comprises a first intermediate element 213 on the distal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate.

Figure 6:
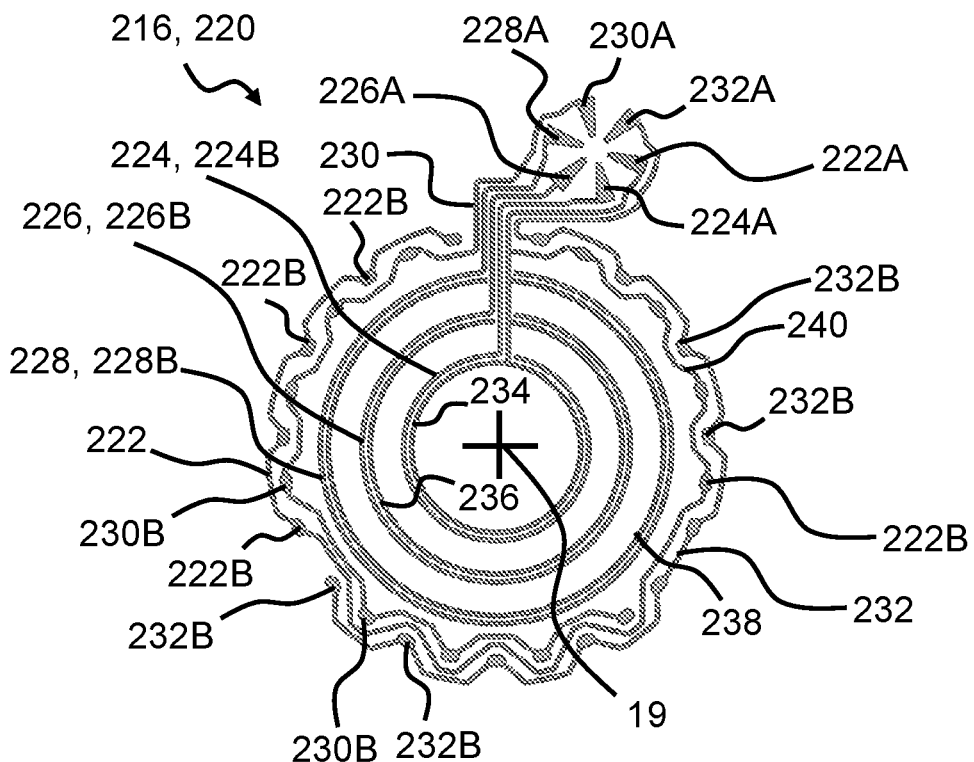
FIG. 6 is a distal view of an exemplary electrode configuration.

FIG. 6 is a distal view of an exemplary electrode configuration 220 of electrodes 216 of the electrode assembly 204. The electrode configuration 220/electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode 230 comprises fourth sensing parts 230B. The fifth electrode 232 comprises fifth sensing parts 232B.

The ground electrode 222 comprises a first electrode part 234 for forming a ground or reference for the first electrode 224. The ground electrode 222 comprises a second electrode part 236 for forming a ground or reference for the second electrode 226. The ground electrode 222 comprises a third electrode part 238 for forming a ground or reference for the third electrode 228. The masking element 218 is arranged proximal to the electrodes 222, 224, 226, 228 covering and insulating parts of the electrodes from the first adhesive and forming respective conductor parts of the electrodes 222, 224, 226, 228. The parts of the electrodes 222, 224, 226, 228 not covered by the masking element 219 contacts the first adhesive layer and form sensing parts 224B, 226B, 228B of electrodes 224, 226, 228, respectively. Further, the electrode parts 234, 236, 238 form sensing parts of the ground electrode 222.

The first sensing part 224B extends circularly at least 330 degrees around the stomal opening at a first radial distance R1 from the center point 19. The first radial distance R1 is 14 mm. The first electrode part 234 is arranged on the inside of the first sensing part (i.e. closer to the center point) and extends circularly at least 330 degrees around the stomal opening at a first ground distance RG1 from the first sensing part (radially from the center point). The first ground distance RG1 between sensing part of first electrode and first electrode part is about 1 mm.

The second sensing part 226B extends circularly at least 330 degrees around the stomal opening at a second radial distance R2 from the center point 19. The second radial distance R2 is 18 mm. The second electrode part 236 is arranged on the inside of the second sensing part 226B (i.e. closer to the center point) and extends circularly at least 330 degrees around the stomal opening at a second ground distance RG2 from the second sensing part 226B (radially from the center point). The second ground distance RG2 between sensing part of second electrode and second electrode part is about 1 mm.

The third sensing part 228B extends circularly at least 330 degrees around the stomal opening at a third radial distance R3 from the center point 19. The third radial distance R3 is about 26 mm. The third electrode part 238 is arranged on the inside of the third sensing part 228B (i.e. closer to the center point) and extends circularly at least 330 degrees around the stomal opening at a third ground distance RG3 from the third sensing part 228B (radially from the center point). The third ground distance RG3 between sensing part of third electrode and third electrode part is about 1 mm.

The ground electrode 222 comprises a fourth electrode part 240 for forming a ground or reference for the fourth electrode 230 and the fifth electrode 232. The fourth electrode part 240 of the ground electrode 222 extends at least 300 degrees around the stomal opening and comprises ground sensing parts 222B. The fourth sensing parts 230B, fifth sensing parts 232B, and ground sensing parts of the fourth electrode part 240 are circularly distributed around the center point 19 at a leakage radius from the center point. The fourth sensing parts 230B, fifth sensing parts 232B, and ground sensing parts of the fourth electrode part may have a radial extension larger than 1.0 mm, such as in the range from 1.5 mm to 3.0 mm, e.g. about 2.0 mm. The fourth sensing parts 230B, fifth sensing parts 232B, and ground sensing parts of the fourth electrode part 240 may have a circumferential extension (perpendicular to the radial extension) larger than 1.0 mm, such as in the range from 2.5 mm to 5.0 mm, e.g. about 3.5 mm.

The ground electrode 222 comprises a first electrode part 234 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B.

Figure 7:
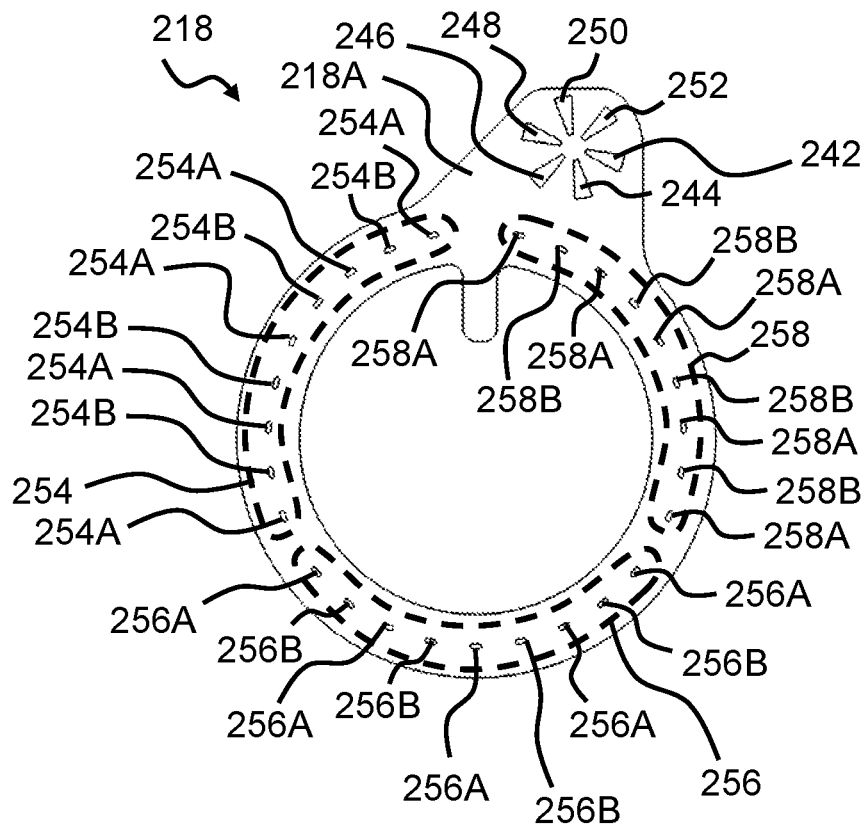
FIG. 7 is a distal view of an exemplary masking element.

FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary masking element, four tertiary second sensor point openings 258B each configured to overlap a part of the ground electrode 222.

Figure 8:
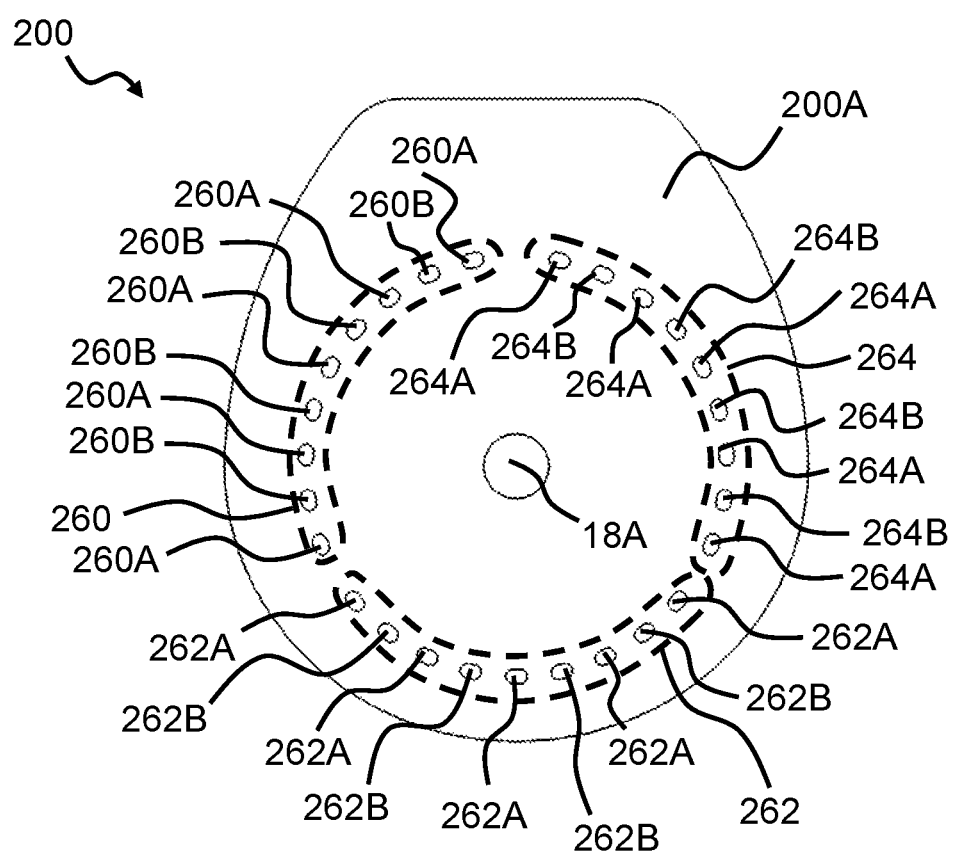
FIG. 8 is a distal view of an exemplary first adhesive layer.
Figure 9:
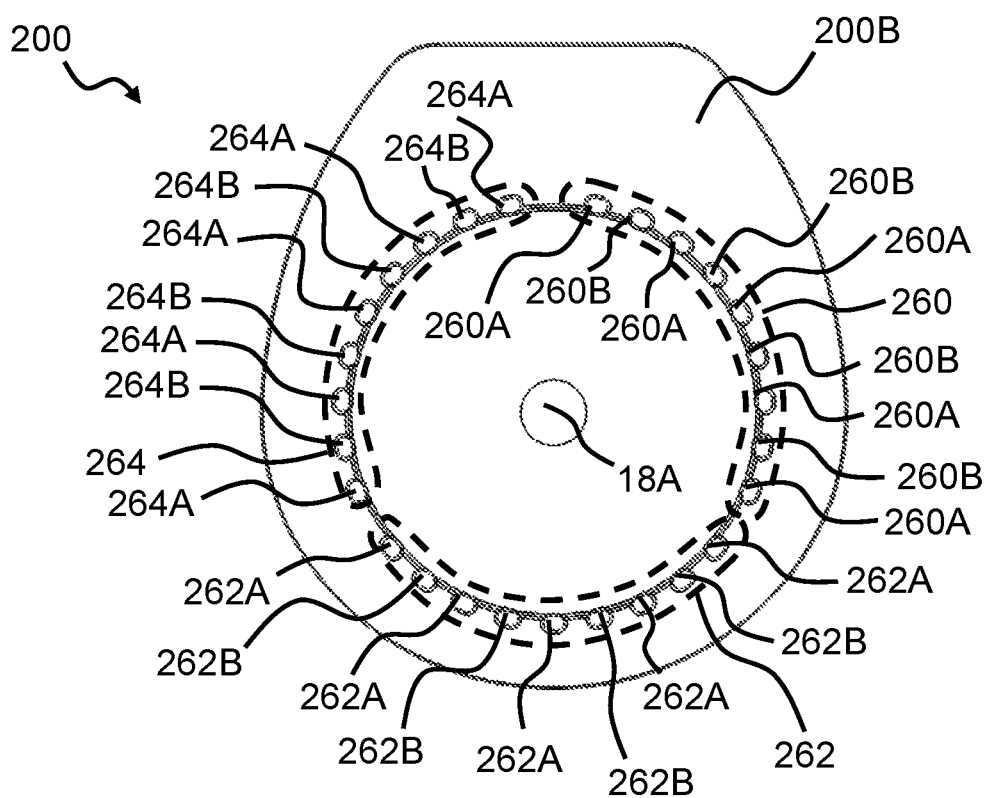
FIG. 9 is a proximal view of the first adhesive layer of FIG. 8.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings 260 comprise, in the illustrated exemplary first adhesive layer, five primary first sensor point openings 260A each configured to overlap a part of the ground electrode 222. The primary sensor point openings 260 comprise, in the illustrated exemplary first adhesive layer, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings 262 comprise, in the illustrated exemplary first adhesive layer, five secondary first sensor point openings 262A each configured to overlap a part of the fifth electrode 232. The secondary sensor point openings 262 comprise, in the illustrated exemplary first adhesive layer, four secondary second sensor point openings 262B each configured to overlap a part of the fourth electrode 230. The sensor point openings of the first adhesive layer comprise tertiary sensor point openings shown within dotted line 264, each tertiary sensor point opening configured to overlap a part of the fifth electrode 232 and/or a part of the ground electrode 222 of the electrode assembly. The tertiary sensor point openings 264 comprise, in the illustrated exemplary first adhesive layer, five tertiary first sensor point openings 264A each configured to overlap a part of the fifth electrode 232. The tertiary sensor point openings 264 comprise, in the illustrated exemplary first adhesive layer, four tertiary second sensor point openings 264B each configured to overlap a part of the ground electrode 222. FIG. 9 is a proximal view of the first adhesive layer of FIG. 8.

Figure 10:
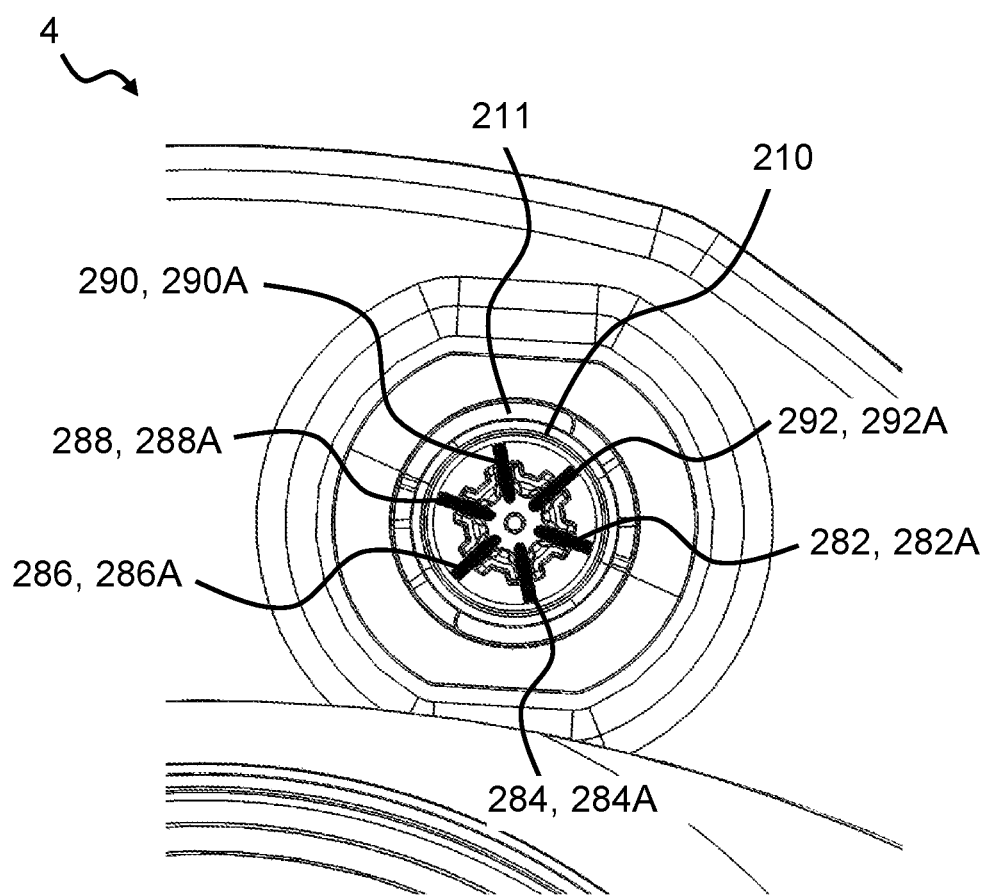
FIG. 10 is a distal view of a part of the base plate including monitor interface.

FIG. 10 is a more detailed distal view of a part of the base plate 4. Monitor interface of the base plate comprises the first connector 211. The first connector 211 comprises coupling part 210 configured to releasably couple the monitor device to the base plate and thus forming a releasable coupling. The first connector 211/monitor interface comprises a plurality of terminals formed by respective terminal elements for forming respective electrical connections with respective terminals of the monitor device.

The plurality of terminals of the first connector 211/monitor interface comprises a ground terminal element 282 forming a ground terminal 282A, a first terminal element 284 forming a first terminal 284, a second terminal element 286 forming a second terminal 286A, and optionally a third terminal element 288 forming a third terminal 288A. The monitor interface optionally comprises a fourth terminal element 290 forming a fourth terminal 290A and/or a fifth terminal element 292 forming a fifth terminal 290. The terminal elements 282, 284, 286, 288, 290, 292 contact respective connection parts 222A, 224A, 226A, 228A, 230a, 232A of electrodes 222, 224, 226, 228, 230, 232.

The position of the first connector on the base plate, the number of terminals and the position of the terminals in the coupling part may be adapted to the electrode configuration used in the electrode assembly of the base plate.

Figure 11:
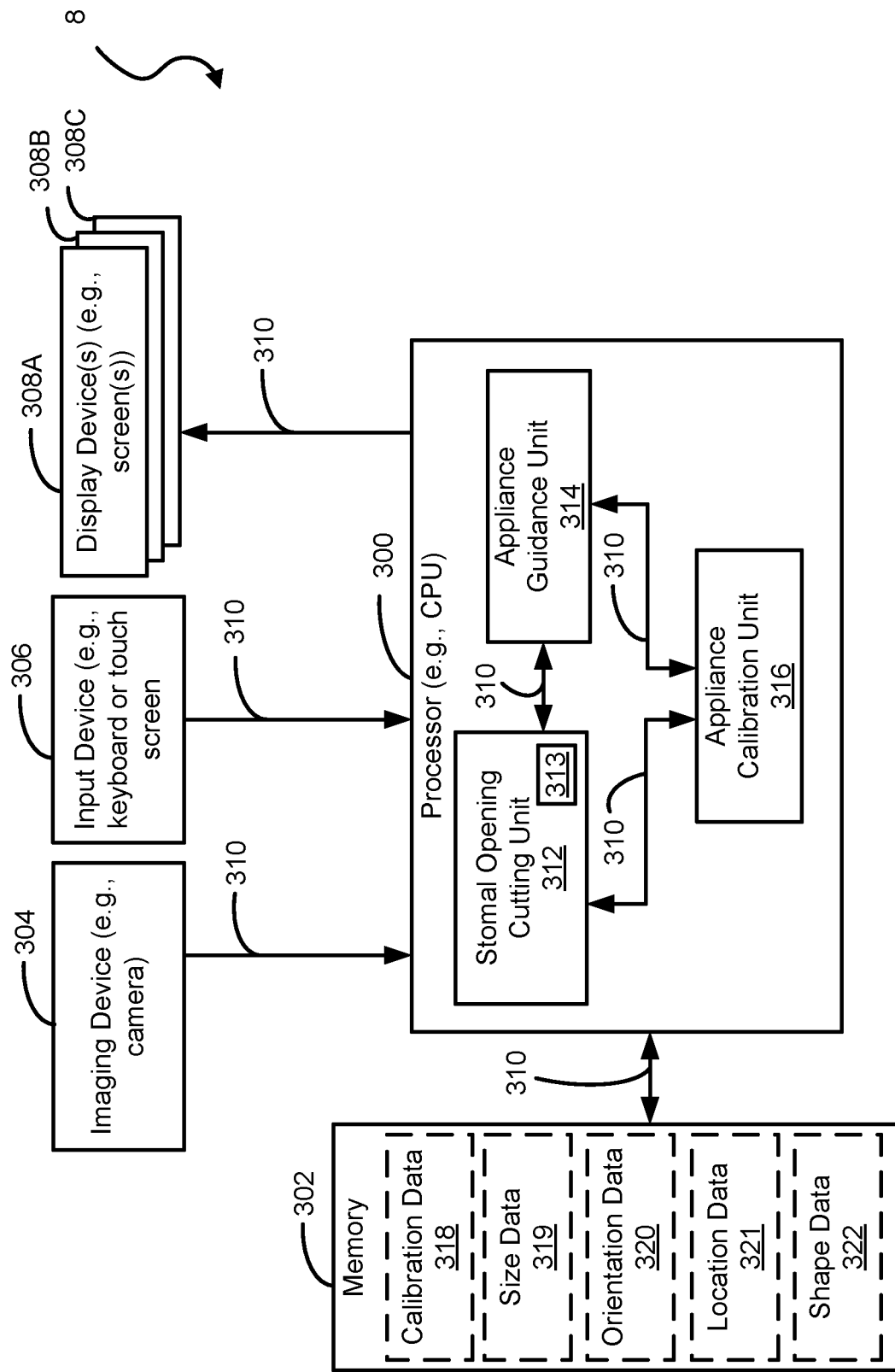
FIG. 11 illustrates an exemplary accessory device in connection with the ostomy appliance for performing various functions.

FIG. 11 is an illustrative block diagram representing the accessory device 8 configured to provide a hole cutting process of the ostomy appliance 2 for a user (e.g. to provide a hole cutting assistance or guidance, e.g. to provide a stoma opening cutting assistance or guidance). It may be seen that the accessory device 8 is configured to provide assistance in preparing an ostomy appliance for use. It is advantageous that this hole cutting process or preparation of the ostomy appliance 2 aids the user to prepare the ostomy appliance 2, such as to properly cut a hole in the ostomy appliance 2 with less difficulty or discomfort and greater accuracy for improved operation of the ostomy appliance 2. The accessory device 8 has peripheral devices, such as a processor 300, a memory 302, an imaging device, such as a camera, 304, an input device 306, and at least one display device 308A, 308B, 308C (collectively 308). Peripheral devices 302, 304, 306, 308 can be operatively and communicably coupled to the processor 300 via a bus 310 for transmitting and receiving data. The processor 300 can be a central processing unit (CPU), but other suitable microprocessors are also contemplated.

The camera 304 captures one or more images and generates image data for subsequent rendering and processing. At least a portion of the image data is displayed on one or more display devices 308 for viewing. The display device 308 can be a touch screen or a monitor, or the like. The input device 306 can be a keyboard or an interactive screen for inputting data, such as alphabetical and/or numerical characters. Input data can be temporarily or permanently stored in the memory 302 or any other suitable database. Other data processed by one or more of the units 312, 314, 316 can also be stored in the memory 302. Calibration data 318, size data 319, orientation data 320, location data 321, and shape data 322 are stored in the memory 302 for subsequent processing.

Further included in the processor 300 are a stomal opening cutting unit 312, an appliance guidance unit 314, and an appliance calibration unit 316. Units 312, 314, 316 can be mutually communicable via the bus 310 for processing relevant data. Detailed descriptions of the units 312, 314, 316 and data 318-322 are provided below in paragraphs related to FIGS. 12-24.

Figure 12:
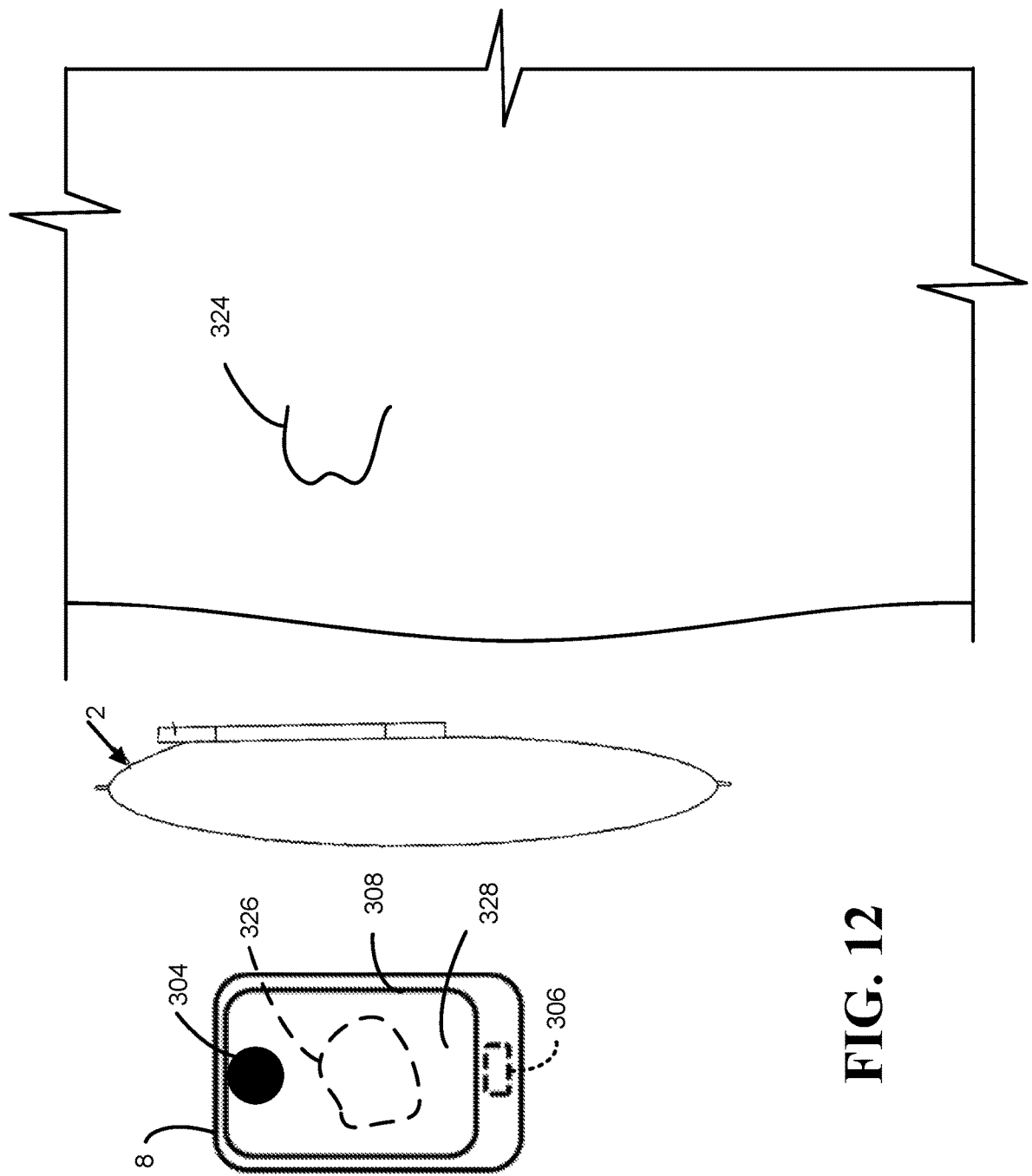
FIG. 12 illustrates the accessory device of FIG. 11 used in connection with the ostomy appliance.

FIGS. 12-16 illustrate processing steps performed by the stomal opening cutting unit 312. FIG. 12 shows that the accessory device 8 is used in connection with the ostomy appliance 2 configured to be placed on a user having a stoma 324. The accessory device 8 includes a display device 308. Before applying the ostomy appliance 2 to the stoma 324, the camera 304 captures one or more images of the user's stoma 324, and the processor 300 processes the images using the stomal opening cutting unit 312. The stomal opening cutting unit 312 receives the images from the camera 304 and identifies the stoma 324.

The stoma 324 on the images can be identified based on an object recognition algorithm that is tolerant of variation in appearance, object scale, rotation and pose. Accurate detection of the stoma 324 may be achieved by the stomal opening cutting unit 312 using object recognition algorithms using the appearance-based and/or feature-based method. Other suitable object recognition methods are contemplated to suit the application. Visual cognition algorithms for recognizing the size and shape of the stoma 324 can be employed using computer vision techniques, such as Speeded-Up Robust Features (SURF) and Scale-Invariant Feature Transform (SIFT). Other suitable techniques are also contemplated to suit different applications in the stomal opening cutting unit 312.

In at least some embodiments, the stoma 324 (and/or the two reference locations 354, 356 discussed below) included an image can be identified using machine learning. For example, the stomal opening cutting unit 313 can include a convolution neural network module 313 to identify the reference locations 354, 356, the stoma 324, the ostomy appliance 2, and/or the like (e.g., skin redness). The reference locations 354, 356, the stoma 324, the ostomy appliance 2, and/or other objects included in an image may be referred to herein as features of an image.

Initially, the convolution neural network module 313 may be configured with weights of the filters used in the convolution neural network module 313 from a pretrained high performing network. In at least some embodiments, each weight value for a filter can correspond to a pixel value (e.g., RGB value, HEX code, etc.) of the filter. However, this is only an example and not meant to be limiting. Additionally or alternatively, the convolution neural network module 313 can be trained, as explained below, on a dataset of images that are of the same ostomist or different ostomists. The images may be captured from the same angle or different angles, in the same lighting or different lighting, and using different cameras 304. Preferably, the images used to train the neural network module 313 are captured from different angles in different lighting using different cameras.

After inputting images into the initial convolution neural network module 313, the convolution neural network module 313 will output identified features based on the initial weights. In at least some embodiments, the convolution neural network module 313 will output a respective mask for each identified feature (e.g., the reference locations 354, 356, the stoma 324, the ostomy appliance 2). The outputted identified features can then be compared against known, verified, and/or confirmed features in the images. Similarly, the known, verified, and/or confirmed features may be represented by masks. In at least some embodiments, the known, verified, and/or confirmed features be manually identified by e.g., one or more humans labeling each of the features in the images.

After the initial convolution neural network module 313 outputs identified features, the initial weights of the convolution neural network module 313 may be adjusted so the features identified by the convolution neural network module 313 closely align with the known, verified, and/or confirmed features. For example, backpropagation can be performed on the convolution neural network module 313 to adjust the weights of the filters to minimize the differences between the features identified by the convolution neural network module 313 and the known, verified, and/or confirmed features. Over several training iterations, optimal or otherwise suitable weights can be learned for the filters of the convolution neural network module 313 and, therefore, the convolution neural network module 313 can be sufficiently trained to identify the reference locations 354, 356, the stoma 324, the ostomy appliance 2, and/or other objects included in an image. For example, a sufficiently trained convolution neural network module 313 has obtained an overall accuracy exceeding 95% when identifying reference locations 354, 356, the stoma 324, the ostomy appliance 2.

The stomal opening cutting unit 312 generates indicia 326 representative of a cutting line for the ostomy appliance 2 as a function of the identified stoma 324 and provides the indicia 326 to the display device 308 for display. The cutting line defines a hole to be formed on the ostomy appliance 2 (e.g., base plate 4) for receiving the stoma 324. The indicia 326 may be a continuous indicium (e.g., a solid line) or discontinuous indicia (e.g., a broken line). The indicia 326 can be displayed by the display device 308 using any type of visual signs or indications, such as a dotted line, a circle, a special character, and the like.

The display device 308 can provide a visual display depicting an appliance representation 328 (either an actual image or a virtual graphical image) and the indicia 326 on the appliance representation. In one case, the appliance representation 328 can be an actual image of the ostomy appliance 2, and the indicia 326 are displayed on top of the actual image of the ostomy appliance 2 for reference. The user can mark one or more marks on the base plate 4 of the ostomy appliance 2 using the indicia 326 on the actual image. The user can readily cut the hole in the base plate 4 of the ostomy appliance 2 with a scissor following the marked line prepared based on the indicia 326 as a guide. Also, the user can cut the hole in the base plate 4 without marking the base plate based on the indicia 326 shown on the actual image as the guide. Using augmented reality (AR) techniques, the indicia 326 can be displayed on a portion of a captured image of the ostomy appliance. Similarly, using virtual reality (VR) techniques, the indicia 326 can be displayed on a portion of a graphical (e.g., virtual) representation of the ostomy appliance. Any combinations of suitable AR and/or VR techniques are also contemplated to suit the application.

During the hole cutting process, the camera 304 may continuously capture a sequence of images of the ostomy appliance 2 including the cut hole so that the sequence of images are captured while the cut is being made by the user. Then, the stomal opening cutting unit 312 can identify the cut and provide the user via the display device 308 with the cut guide indicia 326 such that the cut guide indicia 326 can be used as the guide for the user cutting the hole.

As such, the display device 308 displays the user cut guide indicia 326 on a visual representation of the sequence of images of the ostomy appliance 2 including the cut. The cut guide indicia 326 may be superimposed on the appliance representation (e.g., base plate 4 or bag 332) to guide the user. Any of the marks and/or signs shown on the visual display of the display device 308 can be presented as if they are translucent to show underlying objects or surfaces beyond obstructing objects or materials.

While watching the indicia 326 shown on the actual image of the ostomy appliance 2 on the visual display of the display device 308, the user can revise the marks on the base plate 4 of the ostomy appliance 2 based on the indicia 326 on the visual display of the display device 308. The user can continue to cut the hole in the base plate 4 of the ostomy appliance 2 with the scissor following the revised line prepared based on the indicia 326 as the guide. Also, the user can adjust the hole in the base plate 4 without marking the base plate while watching the indicia 326 shown on the actual image as the guide.

Further, the stomal opening cutting unit 312 can generate a graphical representation of the ostomy appliance 2 (e.g., of an ostomy bag 332) and store it in the memory 302. In this case, the graphical representation can be a virtual or simulated image of the ostomy appliance 2, and the indicia 326 can be displayed on top of the virtual image of the ostomy appliance 2 for reference. The user can be guided by the accessory device 8 to mark one or more marks on the base plate 4 of the ostomy appliance 2 using the indicia 326 displayed on the virtual image by the display device 308. The user can readily cut the hole in the base plate 4 of the ostomy appliance 2 with the scissor following the marked line prepared based on the indicia 326 as the guide. Also, the user can cut the hole in the base plate 4 without marking the base plate based on the indicia 326 shown on the virtual image as the guide.

The camera 304 may continuously capture a sequence of images of the ostomy appliance 2 including the cut hole so that the sequence of images is captured while the cut is being made by the user. The visual display of the display device 308 can display the user cut guide indicia 326 on the virtual image. While watching the indicia 326 shown on the virtual image of the ostomy appliance 2, the user can revise the marks on the base plate 4 of the ostomy appliance 2 based on the indicia 326 on the virtual image. The user can continue to cut the hole in the base plate 4 of the ostomy appliance 2 with the scissor following the revised line prepared based on the indicia 326 displayed by the display device 308 as the guide. Also, the user can adjust the hole in the base plate 4 without marking the base plate while watching the indicia 326 shown on the virtual image displayed by the display device 308 as the guide. Thus, it is advantageous that the cutting line defined by the indicia 326 provides a customized cut around the stoma 324 for improved comfort and enhanced fitting of the ostomy appliance 2. The present disclosure advantageously provides augmented-reality based assistance to the user for performing the technical task of preparing the ostomy appliance 2 for placement on the stoma 324 of the user. Alternatively, the indicia 326 may be stored in the memory 302 or any other database accessible to the accessory device 8, and may be subsequently transmitted to an external entity (e.g., a server device 10 of FIG. 1 via network 12) for providing a customized cut in the ostomy appliance 2. The external entity can be the server device 10 that may be operated and/or controlled by the ostomy appliance manufacturer, such that the ostomy appliance manufacturer can cut the hole in the base plate 4 of the ostomy appliance 2 for the user based on the methods disclosed herein. In this way, the base plate 4 can be precut and customized for future use of the ostomy appliance 2 specifically manufactured for the user. The base plate 4 can be uniformly precut using a stamp tool (e.g., a customized hole puncher) based on the transmitted indicia 326.

Instead of performing the customized cut, the user can use predefined hole indicia 330 shown on the appliance representation of the ostomy appliance 2 presented on the visual display by the display device 308. The predefined hole indicia 330 can be in the form of one or more concentric circles (FIG. 15) presented on the visual display by the display device 308. The predefined hole indicia 330 may be a default cutting line for the ostomy appliance 2 for the user. The concentric circles 330 can be displayed on the actual image of the ostomy appliance 2 or the virtual image of the ostomy appliance 2 presented on the visual display by the display device 308. In either case, the user can choose one of the concentric circles 330 displayed on top of the actual or virtual image of the ostomy appliance 2 that best matches the user's stoma 324 based on the indicia 326 and cut the chosen circle with the scissor. The images of the ostomy appliance 2 including the predefined hole indicia 330 can be stored in the memory 302 or any other database accessible to the accessory device 8.

Figure 13:
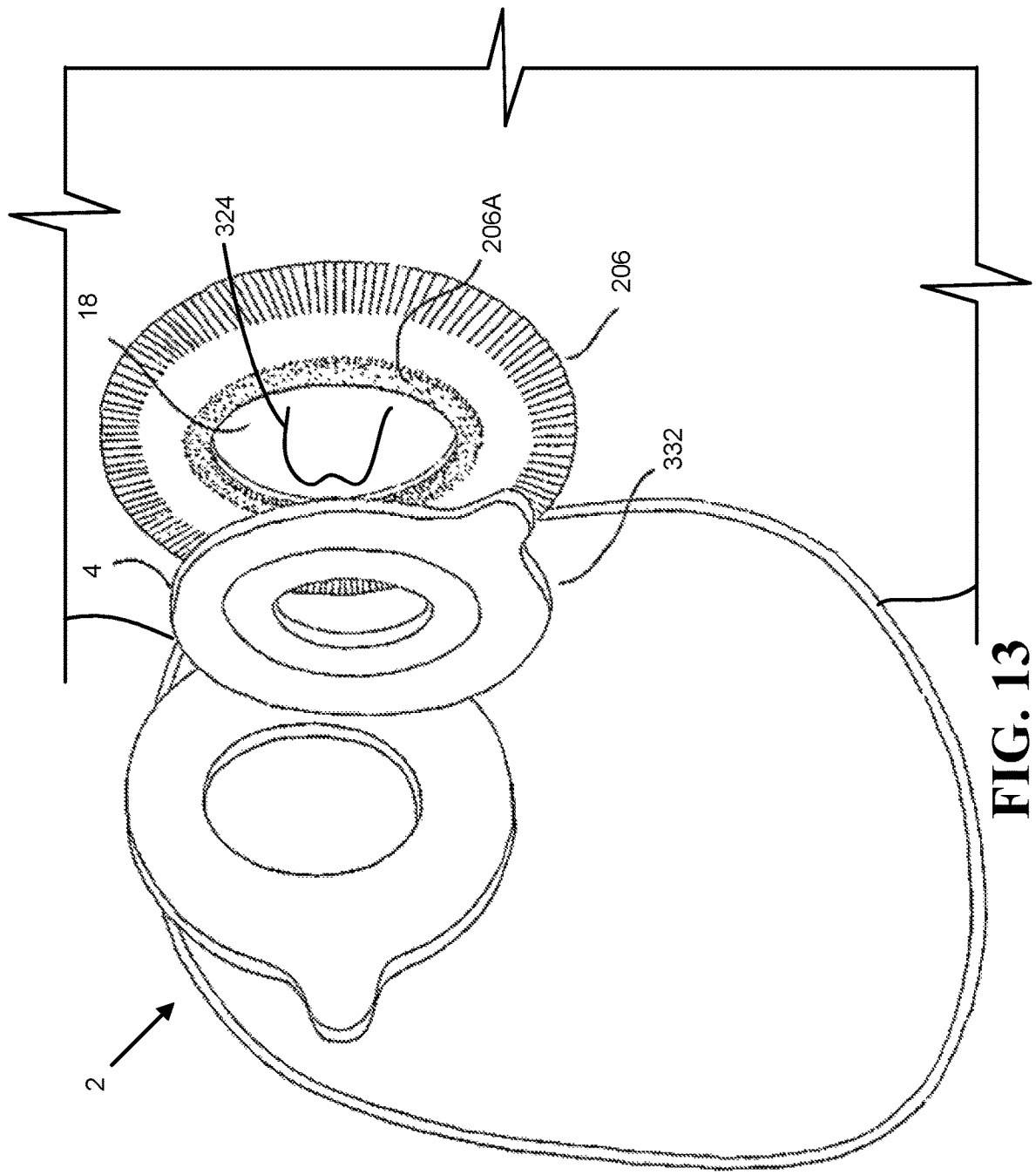
FIG. 13 illustrates the ostomy appliance being applied to a stoma of a user.

FIG. 13 shows the two-part ostomy appliance 2 having an ostomy bag 332 that is being applied to the stoma 324 of the user. In FIG. 13, the base plate 4 includes a release liner 206 that can be peeled off by the user prior to applying the base plate 4 on the skin. A distal surface 206A of the release liner 206 can be attached to the user. Although the two-part ostomy appliance 2 is shown, other suitable types of appliances, such as one-part ostomy appliances, are also contemplated. The camera 304 captures one or more images of the ostomy appliance 2 so that the visual display of the display device 308 can display at least portions of the captured image of the ostomy appliance 2, and the indicia 326 on the at least portions of the captured image of the ostomy appliance. When a two-part ostomy appliance is used, the base plate 4 can be shown as the captured image of the ostomy appliance 2. When a one-part ostomy appliance is used, the ostomy bag 332 can be shown as the captured image of the ostomy appliance 2. The captured image of the ostomy appliance 2 can also include the predefined hole indicia 330 of FIG. 15.

Figure 14:
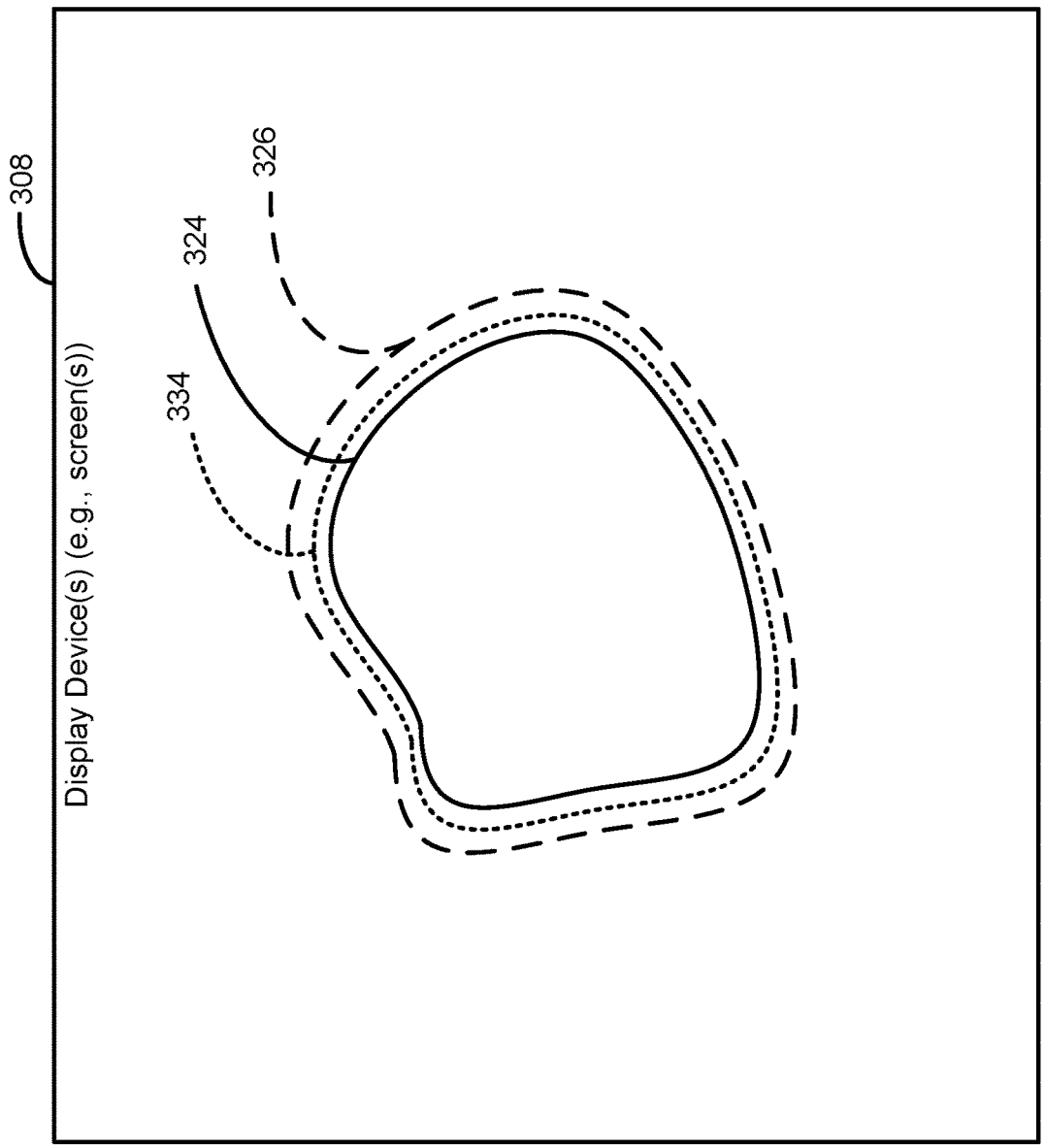
FIG. 14 is an exemplary screen of the accessory device of FIG. 11 depicting a perimeter of the stoma.

FIG. 14 shows an illustrative screen of the visual display of the display device 308 displaying the stoma 324 taken by the user using the camera 304. The stoma 324 on the user's body can be displayed on the screen for image processing. All object recognition and image processing algorithms described above including the appearance-based and/or feature-based method can be generally applied to all relevant steps discussed throughout the present disclosure.

The stomal opening cutting unit 312 can identify parameters representative of a perimeter 334 of the stoma 324. The parameters can be determined based on at least one of: shape, location, size, and orientation information of the stoma 324. The parameters can be determined based on the calibration data 318. The parameters representing an outline of the stoma 324 may be calculated using information related to circumferential edges around the stoma 324. The stomal opening cutting unit 312 can generate the indicia 326 representative of the cutting line as a function of the identified parameters. The stomal opening cutting unit 312 can process the images of the stoma 324 to identify parameters including one or more of size and shape of the stoma 324 for facilitating proper cutting of the hole in the base plate 4.

Figure 15:
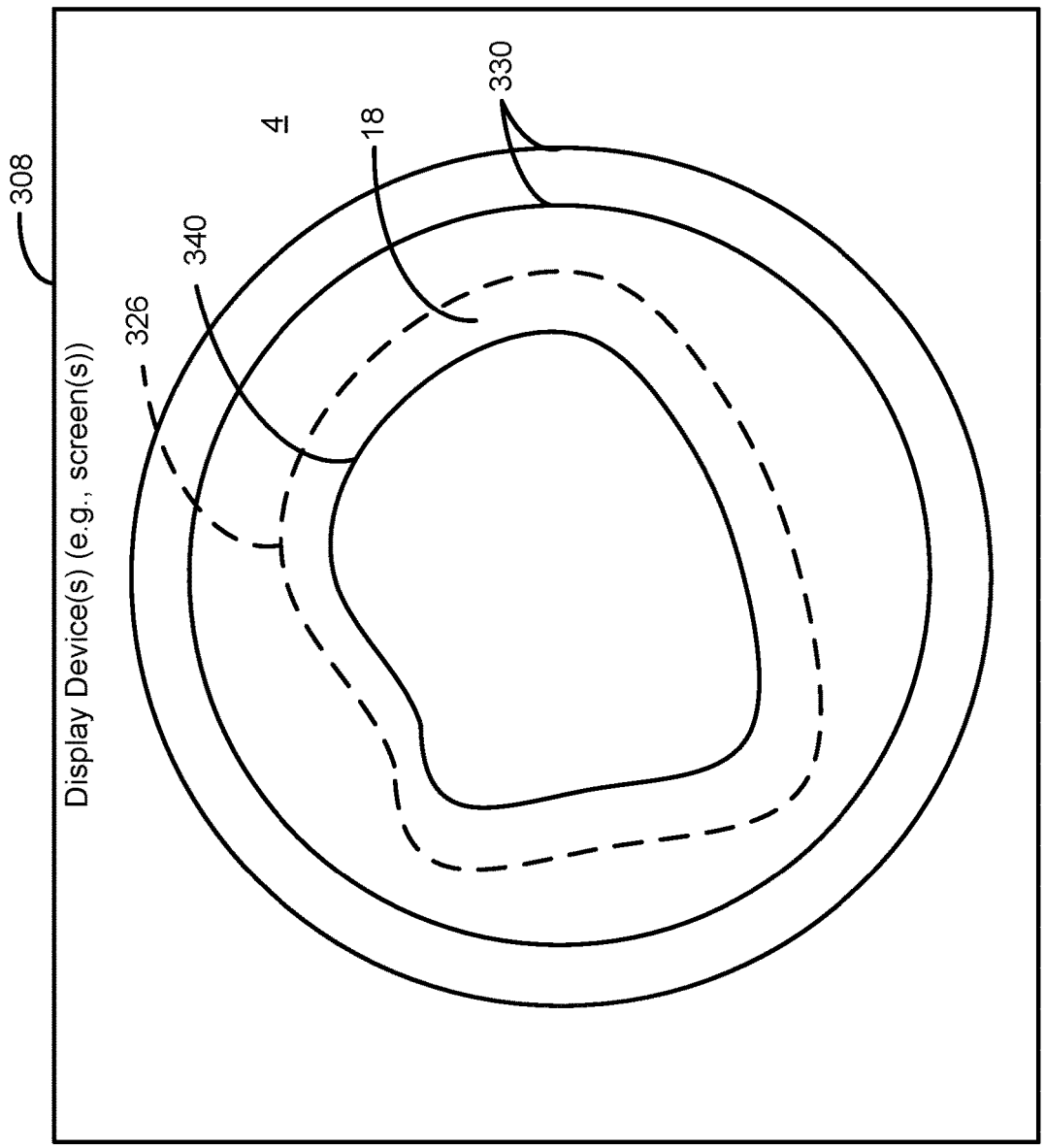
FIG. 15 is an exemplary screen of the accessory device of FIG. 11 depicting a virtual stoma with indicia.

FIG. 15 shows an illustrative screen of the visual display on the display device 308 depicting the indicia 326 and a virtual stoma 340 (e.g., a user interface object representative of the actual stoma 324) representing the perimeter 334 (presented in FIG. 14) of the user's stoma 324 in a relative scale for display purposes. When the actual stoma 324 is hidden or obstructed by the bag 332, the virtual stoma 340 can be displayed by the display device 308 in lieu of the actual stoma 324. The visual display of the display device 308 can also show a portion of the base plate 4 having the stoma-receiving opening 18 defined by the indicia 326 for the virtual stoma 340.

Figure 16:
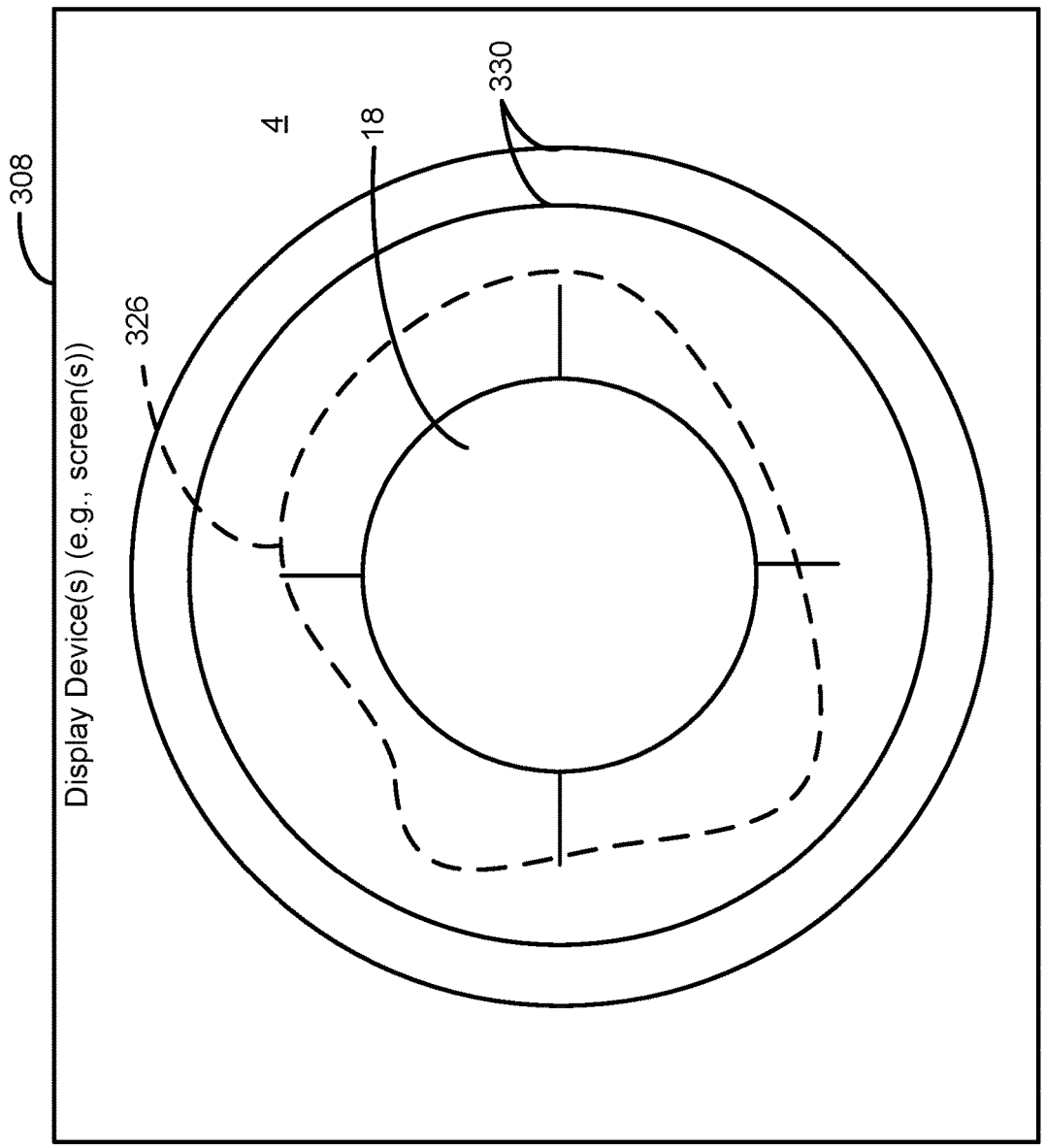
FIG. 16 is an exemplary screen of the accessory device of FIG. 11 depicting a stoma-receiving opening of the base plate.

FIG. 16 shows an illustrative screen of the visual display of the display device 308 depicting the stoma-receiving opening 18 of the base plate 4. The camera 304 captures an image of the ostomy appliance 2 and a cut hole, such as the stoma-receiving opening 18, in the base plate 4 of the ostomy appliance 2. The stomal opening cutting unit 312 identifies the cut hole 18 based on the image and compares the cut hole 18 to the cutting line represented by the indicia 326, which can be shown in real-time on the visual display of the display device 308 for the user.

The comparison of the cut hole 18 and the cutting line represented by the indicia 326 may be performed using a least-squares method to find the best fit for the user's stoma 324. To show the comparison, the visual display of the display device 308 may continuously provide the indicia 326 indicating one or more of accuracy of the cut, progress of the cut, and completion of the cut while the cutting is performed by the user. The comparison can also be shown after the cutting has been completed by the user.

The stomal opening cutting unit 312 can provide instructions to the display device 308 to display an indicator representative of an accuracy of the cut hole 18 with respect to the cutting line represented by the indicia 326. The accuracy of the cut indicates a degree of closeness to the cut guide indicia 326 relative to the actual hole cut by the user. As shown in FIG. 18, the accuracy of the cut can be shown on the visual display of the display device 308 with a traffic light having red 344, yellow 346, and green 348 lights, where the red may indicate an improper cut, the yellow may indicate an acceptable but undesirable cut, and the green may indicate a proper cut. Also, at least a portion of the cut guide indicia 326 can be highlighted in red, yellow, and green to indicate the degree of closeness to the cut guide indicia 326 in comparison with the actual hole cut by the user. A numerical indication between 0 and 10 showing the degree of closeness is also contemplated to suit different applications. The number 0 may indicate the worst cut and the number 10 may indicate the best cut.

When an unacceptable accuracy of the cut is indicated by the red light 344, the user can correct the cutting line using the indicia 326 on the visual display of the display device 308 as the guide. Since each light (red, yellow, or green) indicates how far the mark is off from the cutting line is off the indicia 326, the user can easily recognize deviation from the indicia 326 and properly fix the cutting line.

The stomal opening cutting unit 312 can also be configured to indicate to the display device 308 to display a progress and completion of cutting the hole 18 with respect to the cutting line represented by the indicia 326. The progress of the cut indicates a degree of advancement of a cutting process performed by the user. A progress bar for visualizing the progression of the cutting process can be displayed on the visual display of the display device 308. Other suitable progress element, such as a percentage of the cutting process completed, can also be shown. The completion of the cut indicates a conclusion of the cutting process. The display device 308 may be configured to display a textual or graphical sign to notify the user of the conclusion of the cutting process. Other suitable signs, such as audible warnings for the completion of the cut, are also contemplated.

The stomal opening cutting unit 312 can receive the calibration data 318. The calibration data 318 can be representative of the size of the user's stoma 324. The calibration data 318 can be provided by the appliance calibration unit 316. The stomal opening cutting unit 312 can generate the indicia 326 as a function of the calibration data 318. The cut guide indicia 326 may be generated based on the calibration data 318 associated with the stoma 324. The stomal opening cutting unit 312 can receive the calibration data 318 through a graphical user interface, e.g., by instructing the display device 308 to receive the calibration data 318 from the user using the visual display of the display device 308. Similarly, the stomal opening cutting unit 312 can also receive the calibration data 318 through the input device 306, such as a keyboard. The appliance calibration unit 316 may capture an image of a scale 358 (FIG. 20) having predetermined dimension indicia with the captured one or more images of the user's stoma 324, and process the image of the scale 358 to generate the calibration data 318. Detailed descriptions of the appliance calibration unit 316 are provided below in paragraphs related to FIGS. 19-21.

Figure 17:
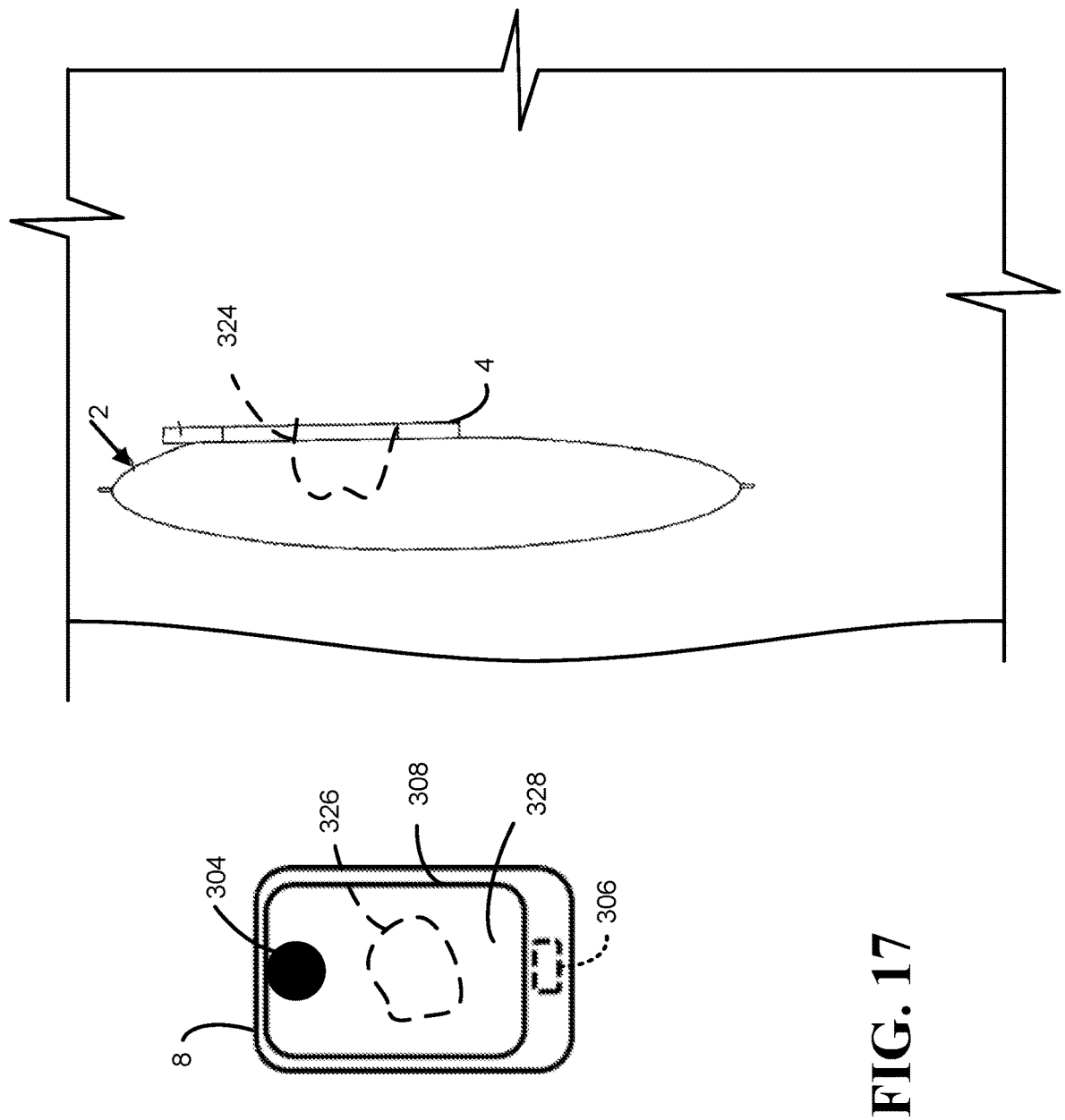
FIG. 17 illustrates the ostomy appliance applied to the user's stoma.

FIGS. 17-18 illustrate processing steps performed by the appliance guidance unit 314 during a fitting process of the ostomy appliance 2, e.g., after the hole has been made by the user and the user is provided assistance to place the ostomy appliance 2. FIG. 17 shows the ostomy appliance 2 being applied to the stoma 324 and the accessory device 8 having a visual display of the display device 308 depicting the ostomy appliance 2 during the fitting process. In FIG. 18, the visual display of the display device 308 can display the fitting process performed by the appliance guidance unit 314 while the ostomy appliance 2 is being applied to the stoma 324. The appliance guidance unit 316 is configured to guide the placement of the ostomy appliance 2 on the user having the stoma 324 by providing instructions to the display device 308. The camera 304 captures an image or a sequence of images of the user applying the ostomy appliance 2 to the user's body. The display device 308 is configured to provide a visual display that can display an image of at least a portion of the actual ostomy appliance 2 from one or more of the captured image or sequence of images during the fitting process of the ostomy appliance 2 to the user's stoma 324.

Figure 18A:
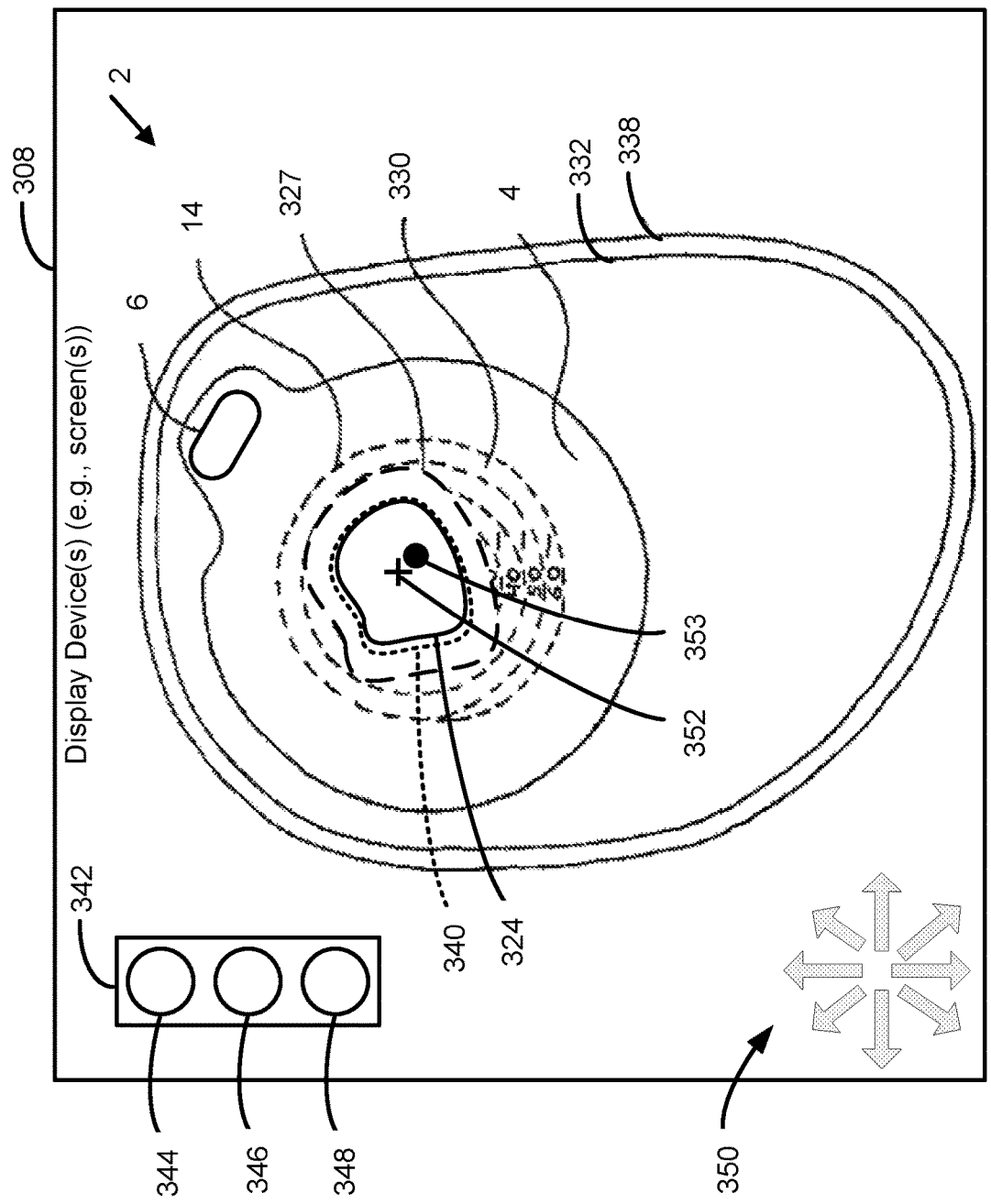
FIG. 18A is an exemplary screen of the accessory device of FIG. 11 depicting a stoma location representation relative to a location of an ostomy bag.
Figure 18B:
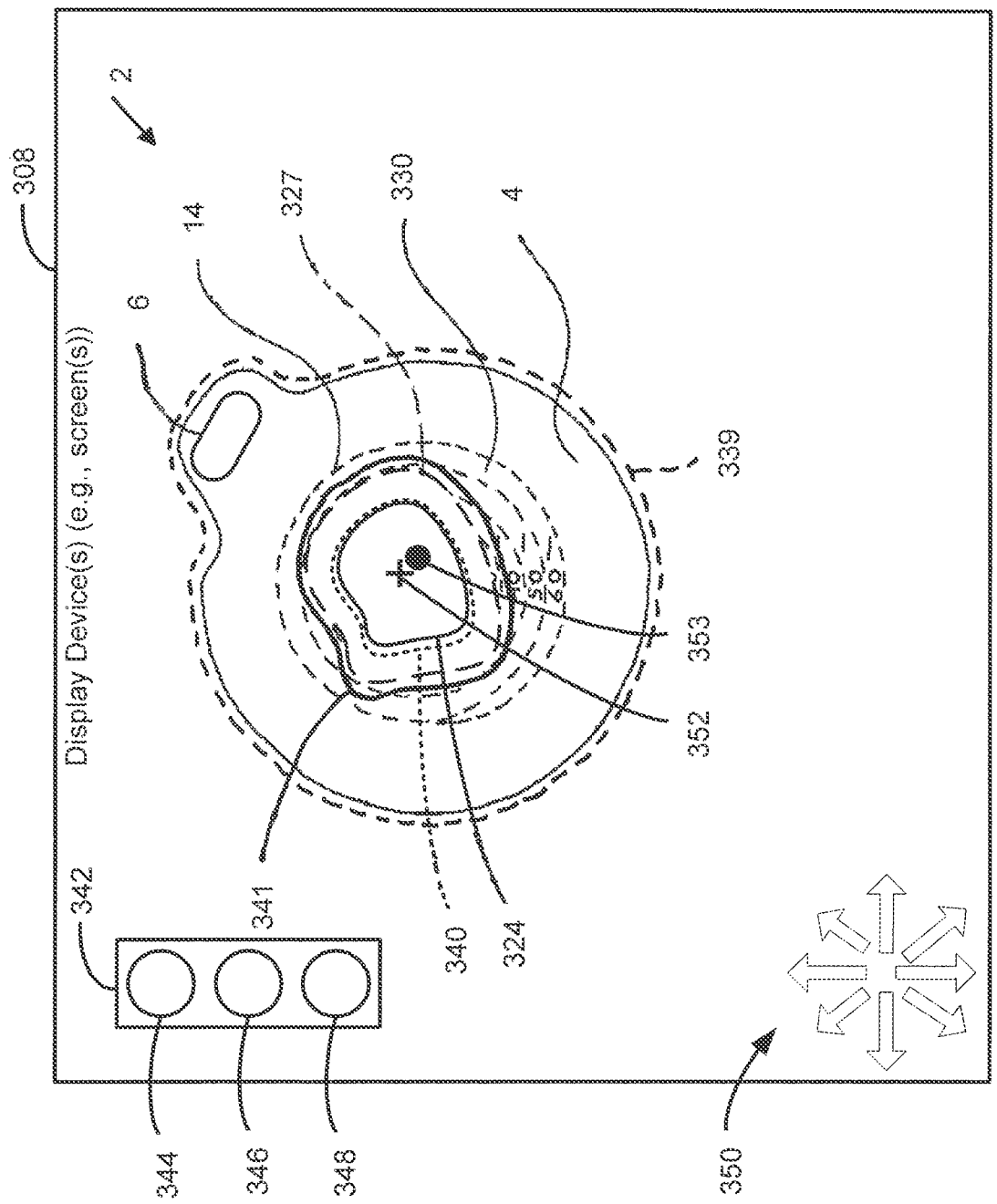
FIG. 18B is an exemplary screen of the accessory device of FIG. 11 depicting a stoma location representation relative to a location of the base plate.

As shown in FIGS. 18 and 18A, the ostomy appliance 2 can include the base plate 4 and the bag 332. The base plate 4 and the bag 332 can be integrally formed as a single unit or can be separate units detachable by the user as needed. The appliance guidance unit 316 can generate location indicia representative of the location of the ostomy appliance 2 with respect to the stoma 324 in one or more of the captured image or sequence of the images, and provide the location indicia in one or more of the captured image or sequence of the images in the visual display of the display device 308. The location indicia can include a stoma location representation and an appliance location representation. The stoma location representation may represent a desired location of the ostomy appliance 2, and the appliance location representation may represent a current location of the ostomy appliance 2.

The stoma location representation can be an actual location of the actual stoma 324 when it is visible in the captured image or sequence of the images. The actual location of the stoma 324 can be identified based on the object recognition algorithm using a two dimensional plane having X-axis and Y-axis in the Cartesian coordinate system relative to the user's body. Other spatial recognition algorithms using a three dimensional space are also contemplated. The appliance guidance unit 316 identifies a location of the ostomy appliance 2 in one or more of the captured image or sequence of images using similar techniques. The appliance guidance unit 316 provides the location of the ostomy appliance 2 in one or more of the captured image or sequence of images to the display device 308, which in turn displays the stoma location representation.

When the actual stoma 324 is hidden or obstructed by the bag 332, the stoma location representation can be a calculated location of the virtual stoma 340. The calculated location of the virtual stoma 340 can be determined based on at least one mark on the user's body and the calibration data 318 having the location data 321.

The appliance location representation can be a current location of a cut line 327. The cut line 327 may represent the hole cut by the user with respect to the stoma 324. To perform the alignment, the cut line 327 can be moved close to the actual stoma 324 or the virtual stoma 340. During the alignment, the comparison of the actual stoma 324 (or the virtual stoma 340) to the cut line 327 may be performed using the least-squares method to find the best location for the ostomy appliance 2. The comparison may be provided to the display device 308 for display.

Also, the stoma location representation can be a desired location 341 of the cut line 327. The desired location 341 of the cut line may represent a target location of the ostomy appliance 2 with respect to the actual stoma 324 or the virtual stoma 340. The appliance location representation can be the current location of the cut line 327. To perform the alignment, the cut line 327 can be moved close to the desired location 341 of the cut line. During the alignment, the comparison of the desired location 341 of the cut line to the current location of the cut line 327 may be performed using the least-squares method to find the best location for the ostomy appliance 2.

Further, the stoma location representation can be a desired location 338 of the bag 332 (FIG. 18). The desired location 338 of the bag 332 represents a target location of the ostomy appliance 2 with respect to the actual stoma 324 or the virtual stoma 340. The appliance location representation can be a current location of the bag 332. To perform the alignment, the current location of the bag 332 can be moved close to the desired location 338 of the bag.

Similarly, the stoma location representation can be a desired location 339 of the base plate 4 (FIG. 18A). The desired location 339 of the base plate may represent a target location of the ostomy appliance 2 with respect to the actual stoma 324 or the virtual stoma 340. The appliance location representation can be a current location of the base plate 4. To perform the alignment, the current location of the base plate 4 can be moved close to the desired location 339 of the base plate.

At least a portion of an outer periphery of the bag 332 or base plate 4 can be highlighted in red, yellow, and green to indicate the degree of closeness to the desired location 338 of the bag or the desired location 339 of the base plate. The red may indicate an improper alignment, the yellow may indicate an acceptable but undesirable alignment, and the green may indicate a proper alignment. A numerical indication between 0 and 10 showing the degree of closeness to the location indicia 338 is also contemplated to suit different applications. The number 0 may indicate the worst alignment and the number 10 may indicate the best alignment. Other displayed objects can also similarly employ the coloring or numerical indication techniques.

As another alternative or additional way of alignment, the stoma location representation can be a target location indicia 352 representative of a desired location of the ostomy appliance 2. The appliance location representation can be a current location indicia 353 representative of a current position of the ostomy appliance 2. To perform the alignment, the current location indicia 353 can be moved close to the target location indicia 352.

More specifically, the appliance guidance unit 316 may provide the target location indicia 352 representative of a desired position of the ostomy appliance 2 on the user, and the current location indicia 353 representative of a current position of the ostomy appliance 2 on the user. The target and current location indicia 352, 353 can include any visible object, such as a character, a geometrical shape, a line segment, or the like. The visible object can be a circle, a special character, or a perimeter.

The target location indicia 352 may represent a center of the stoma location representation, such as the actual stoma 324 or the virtual stoma 340, and the current location indicia 353 may represent a center of the appliance location representation. The current location indicia 353 can be associated with the bag 332 or the base plate 4 of the ostomy appliance 2. As the ostomy appliance 2 is oriented for alignment, the current location indicia 353 can move closer to the target location indicia 352 for proper alignment of the cut line 327 on the user's stoma 324. The target and current location indicia 352, 353 can be superimposed when they are in close proximity or at the same position. Additional orientation displacements, such as rotations, may be required to properly align the cut line 327 with the stoma 324.

During the alignment, the comparison of the target location indicia 352 and the current location indicia 353 may be performed using the least-squares method to find the best location for the ostomy appliance 2. To show the comparison, the visual display of the display device 308 may continuously provide the target and current location indicia 352, 353 indicating one or more of accuracy of the alignment, progress of the alignment, and completion of the alignment while the alignment is performed by the user. The comparison can also be shown after the alignment has been completed by the user.

At least a portion of the target location indicia 352 can be highlighted in red, yellow, and green to indicate the degree of closeness to the target location indicia 352 in comparison with the current location indicia 353. The red may indicate an improper alignment, the yellow may indicate an acceptable but undesirable alignment, and the green may indicate a proper alignment. Also, the numerical indication between 0 and 10 showing the degree of closeness to the target location indicia 352 is also contemplated to suit different applications. The number 0 may indicate the worst alignment and the number 10 may indicate the best alignment. The visual display of the display device 308 can also show other graphics to show the accuracy, progress, or completion of the alignment with respect to the current location indicia 353.

Any of the methods discussed above can be performed with actual and/or graphical representations displayed on the visual display of the display device 308 depending on the application. By way of example, the virtual stoma 340 can be used in lieu of the actual stoma 324, or the graphical representation of the bag 332 or the base plate 4 can be used in lieu of the actual image of the bag or the base plate.

To further guide the user for a proper alignment of the ostomy appliance 2 in real-time, the appliance guidance unit 316 may generate a quality indicator 342 representative of a current position of the ostomy appliance 2 with respect to a desired position related to the stoma 324. The quality indicator 342 can be associated with the bag 332 and/or the base plate 4 of the ostomy appliance 2. The quality indicator 342 may be indicative of a degree of deviation of the ostomy appliance 2 from the stoma 324 (or the virtual stoma 340).

The visual display of the display device 308 can display a visual display of the quality indicator 342 resembling a traffic light having red 344, yellow 346, and green 348 lights, each of which is selectively highlighted based on a quality of fitting. During alignment, each light may indicate a degree of deviation from the stoma 324 (or the virtual stoma 340). The red may indicate an improper alignment, the yellow may indicate an acceptable but undesirable alignment, and the green may indicate a proper alignment. The degree of deviation can be determined using variance algorithms used in computational statistics for indicating a difference between a current position and a desired position, such as the first and current location indicia 352, 353.

Other suitable indicators, such as numeric values between 0 and 10, are also contemplated to suit different applications. The number 0 may indicate the worst fit and the number 10 may indicate the best fit. The location indicia 338 itself may be lighted in different colors to indicate the quality of fitting. Alternatively, the graphical representations representing the current or desired position, such as the target or current location indicia 352, 353, may be highlighted separately or simultaneously in different colors to indicate the quality of fitting. Other suitable combinations of the indicators are also contemplated.

The appliance guidance unit 316 can generate the location indicia in the form of a direction indicator 350 representative of an orientation and position direction with respect to the ostomy appliance 2 that should be moved to locate the ostomy appliance 2 at a desired position with respect to the stoma 324. The direction indicator 350 can be associated with the orientation and position direction of the bag 332 and/or the base plate 4. Guided by the direction indicator 350, the user can simply move the bag 332 and/or the base plate 4 toward the stoma 324. In lieu of the stoma 324, the virtual stoma 340 can be used when the stoma 324 is covered by the bag 332.

The visual display of the display device 308 can display the direction indicator 350 in different or highlighted colors to guide the user for proper alignment of the ostomy appliance 2. The direction indicator 350 can include multiple directions, e.g., up, down, right, left, and the like. When the up direction indicator is lighted, the user can upwardly move the ostomy appliance 2 toward the target location indicia 352. When the down direction indicator is lighted, the user can downwardly move the ostomy appliance 2 toward the target location indicia 352.

As similarly discussed above, at least a portion of the direction indicator 350 can be highlighted in red, yellow, and green to indicate the degree of closeness to the desired location of the ostomy appliance 2. The red may indicate an improper position, the yellow may indicate an acceptable but undesirable position, and the green may indicate a proper position. Also, the numerical indication between 0 and 10 showing the degree of closeness to the desired location is also contemplated to suit different applications. The number 0 may indicate the worst position and the number 10 may indicate the best position.

Also, rotation indicators can be used in combination with the direction indicator 350. Other suitable animated indicators are also contemplated to suit different applications. Advantageously, the appliance guidance unit 316 can generate and instruct the display device of the display device 308 to display a graphical simulation of the stoma 324 and the ostomy appliance 2 for aiding the user to properly apply the ostomy appliance 2 to the user's body with less difficulty or discomfort.

The appliance guidance unit 314 can receive the calibration data 318 representative of the location of the stoma 324 on the user's body with respect to a reference indicator (e.g., reference locations 354, 356 in FIG. 19) on the user's body that is visible in one or more of the captured image or sequence of images. The appliance calibration unit 316 can identify the reference indicator on the user's body, and also identify the location of the stoma 324 as a function of the identified reference indicator on the user's body and the calibration data 318. The appliance calibration unit 316 can identify the reference indicator on the ostomy appliance 2. Detailed descriptions of the calibration data 318 and the appliance calibration unit 316 are provided below in paragraphs related to FIGS. 19-21.

Figure 20:
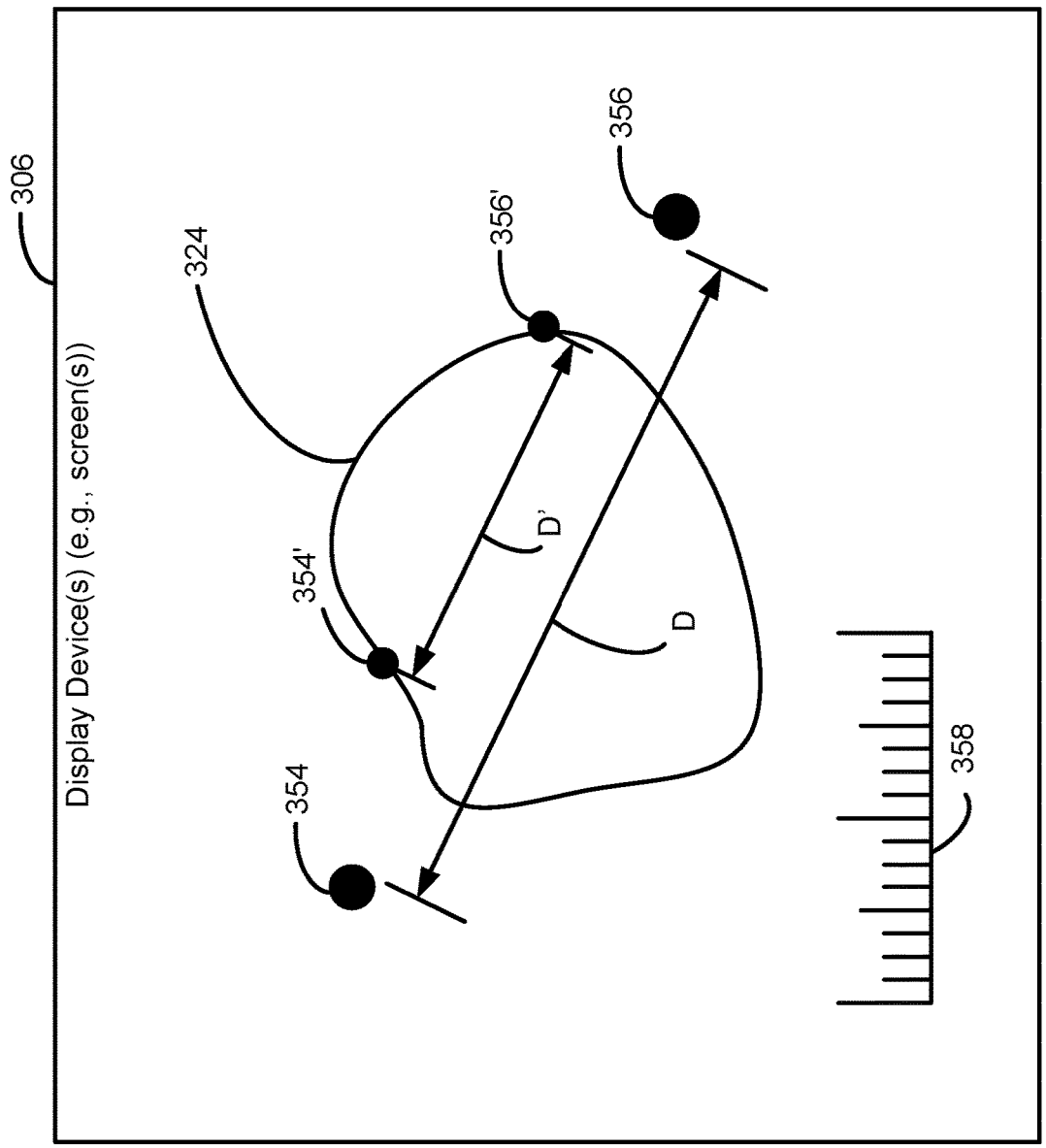
FIG. 20 is an exemplary screen of the accessory device of FIG. 11 depicting the stoma with reference locations on the user's body.
Figure 21:
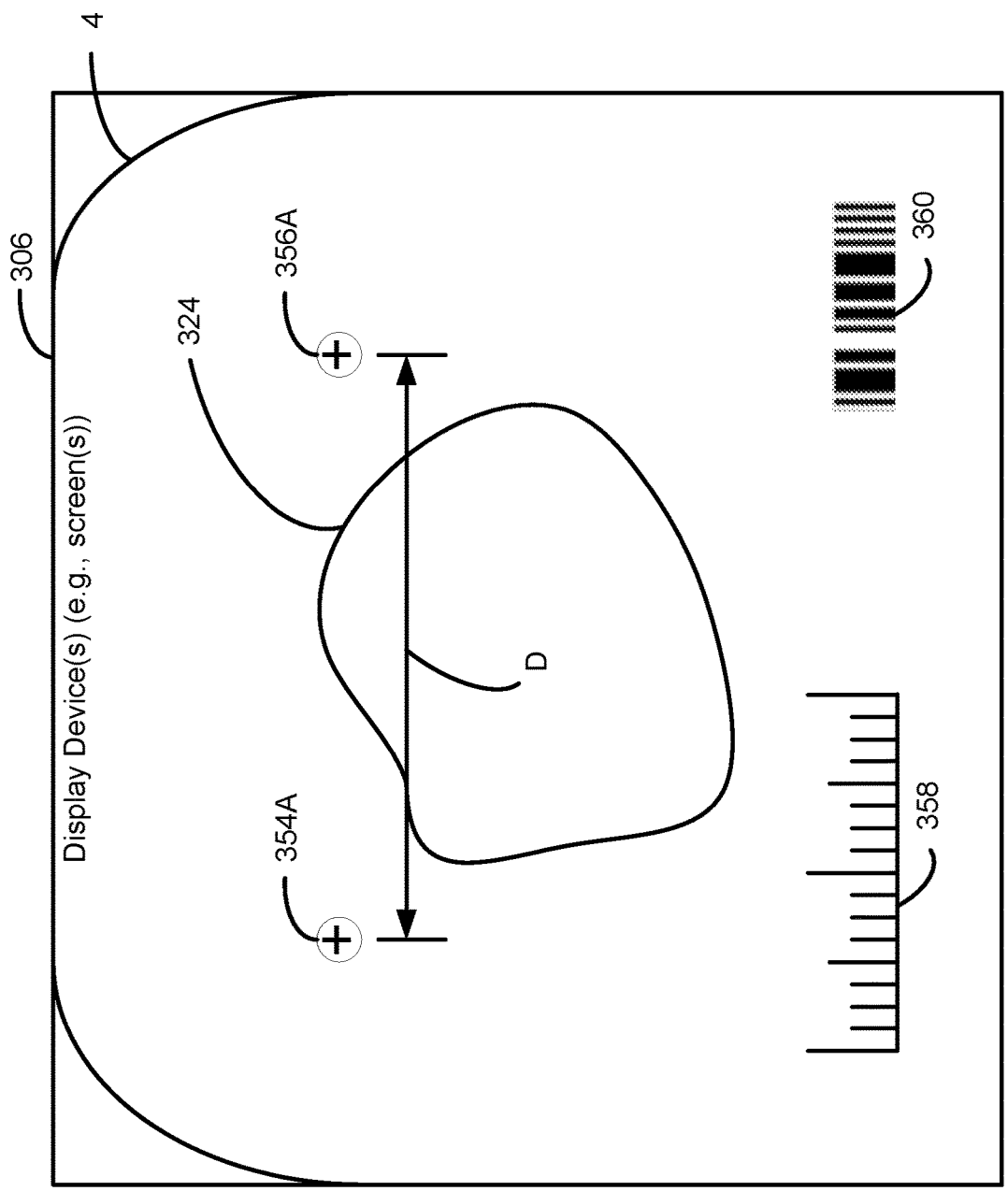
FIG. 21 is an exemplary screen of the accessory device of FIG. 11 depicting the stoma with reference locations on the ostomy appliance.

FIGS. 19-21 illustrate processing steps performed by the appliance calibration unit 316 configured to calculate an actual size of the stoma 324 based on distance scale information 358. In FIG. 19, at least two reference locations associated with the stoma 324, namely a first reference location 354 and a second reference location 356, are used to determine the distance scale information 358. The distance scale information 358 representative of a distance D between the two reference locations 354, 356 is used to calculate the actual size of the stoma 324. More specifically, the appliance calibration unit 316, using the camera 304, captures an image of the stoma 324 with the first reference location 354 and the second reference location 356 to determine the distance D between the first and second reference locations 354, 356.

FIG. 20 shows an illustrative screen of the visual display of the display device 308 depicting the stoma 324 with at least two reference locations 354, 356. The at least two reference locations 354, 356 are spaced-apart marks located on the user's body and/or on the ostomy appliance 2. The appliance calibration unit 316 is configured to capture, using the camera 304, an image of a portion of a user's body that includes the user's stoma 324 and the at least two reference locations 354, 356. At least one of the reference locations 354, 356 may include a feature of the user's body at a location spaced apart from the stoma 324 to determine the stoma location data 321 with respect to the feature of the user's body. When only one feature is available on the user's body, the location of the stoma 324 can be determined based on the stoma location data 321 and the one feature on the user's body. In this case, from the feature identified on the user's body, the appliance guidance unit 316 can determine an exact location of the stoma 324 using the stoma location data 321 and/or the stoma orientation data 320.

The at least two reference locations 354, 356 may include at least two spaced-apart features of the user's body. The first reference location 354 may be a birthmark, mole, blemish, nevus, or any other remarkable symbol disposed on the user's body. The second reference location 356 may be a navel or belly button. When such marks are not present on the user's body, the user can also draw two distinct marks as the two reference locations on the user's body using a writing instrument. Any other suitable marks on the user's body recognizable by the camera 304 are contemplated.

Any portions of the user's stoma 324 can also be the two reference locations. The at least two reference locations 354, 356 may include at least two spaced-apart features of the user's stoma 324. Any portion of the stoma 324 can be the reference location. A distance D' defined by any two points 354', 356' disposed on an outermost peripheral edge of the stoma 324 may be the two reference locations.

Further, the two reference locations may be any portions on the ostomy appliance 2. Any portions of the ostomy appliance 2 may be the two reference locations. For the base plate 4, any portions of outermost peripheries of the base plate 4 can be the reference locations. Also, any predetermined marks printed on the base plate 4 can also be the reference locations. Similarly, any portions of outermost peripheries of the bag 332 can be the reference locations. Also, any predetermined marks printed on the bag 332 can also be the reference locations. In the absence of the predetermined marks, the user can draw two distinct marks on the base plate 4 or the bag 332 using the writing instrument.

As shown in FIG. 21, the two reference locations can be two marks 354A, 356A on the user's body. The two marks 354A, 356A can be on the release liner 206 removable from the ostomy appliance 2. The two marks 354A, 356A can be predetermined marks printed on the release liner 206 (FIG. 13) or drawn by the user. The release liner 206 can be peeled off by the user from the ostomy appliance 2 and adhesively attached to the user's body.

The at least two reference locations may include at least one feature of the user's body (e.g., the birthmark, mole, blemish, nevus, or the like) and at least one mark applied to the user's body (e.g., drawn by the user using the pen). The at least one mark can include at least one mark on the substrate 206 positioned on the user's body that was removed from the ostomy appliance 2 and adhesively attached to the user's body. As such, any combinations of marks on the user's body and/or the ostomy appliance 2 including the bag 332 and the base plate 4 can be used as two reference locations to suit different applications.

When the two reference locations 354, 356 are identified, the appliance calibration unit 316 can receive the distance scale information 358 representative of the distance D either on the imaged ostomy appliance 2 or on the user's body through a user interface, such as the input device 306. The user may enter an actual size of the distance D in a numerical value (e.g., 3 inches) using a keyboard. To determine the actual size, the application calibration unit 316 may count a number of pixels disposed between the two reference locations 354, 356. The application calibration unit 316 can proportionally extrapolate a pixel ratio relative to the entered size to calculate the distance of any two reference locations of the stoma 324. Using this extrapolation technique, the application calibration unit 316 can generate the calibration data 318. In at least some embodiments, the images may be scaled to an image size having the same number of pixels, e.g., 256×256. Then, using the distance scale information 358, each pixel may correspond to a physical distance (e.g., ×square centimeters, etc.) Additionally or alternatively, each pixel may be assigned an x, y coordinate to facilitate describing the locations of different features in images (e.g., the reference locations 354, 356, the stoma 324, the ostomy appliance 2, and/or the like) and their relative positions to one another.

However, the distance scale information 358 can also be automatically retrieved from an external database or storage. As shown in FIG. 21, the camera 304 can capture an image of the ostomy appliance 2 that includes at least two reference locations 354A, 356A and determine the distance D between the at least two reference locations 354A, 356A on the image of the ostomy appliance 2 by accessing the stored distance scale information 358 in the memory 302 or any other storages.

The application calibration unit 316 can identify a machine-readable code 360 recognized by the camera 304, and automatically retrieve the distance scale information 358 based on the code 360 from the external database or storage, such as the memory 302. A manufacturer of the ostomy appliance 2 may insert the distance scale information in the memory 302. The machine-readable code 360 may be a barcode or any optical code representing a product identification of the ostomy appliance 2. As known in the art, the barcode can be disposed on any part of the ostomy appliance 2, such as the base plate 4 or bag 332. The barcode can represent a model number of the ostomy appliance 2 having information associated with a reference dimension of the ostomy appliance 2 including the distance D. As discussed above, the application calibration unit 316 can proportionally extrapolate the distance scale information 358 to generate the calibration data 318.

The appliance calibration unit 316 can store distance scale information 358 representative of the distance D between the two reference locations 354, 354', 354A (collectively 354) and 356, 356', 356A (collectively 356) in the memory 302. Based on the distance scale information 358, the appliance calibration unit 316 can generate the calibration data 318 representative of one or more stoma parameters as a function of the identified reference locations 354, 356, identified stoma 324 and the distance scale information 358. The stoma parameters may include information related to one or more of size, orientation, location, and shape data associated with the stoma 324. The application calibration unit 316 is configured to generate the calibration data 318 representative of a location of the stoma 324 with respect to the feature of the user's body as a function of the identified reference locations 354, 356, identified stoma 324 and the distance scale information 358.

The calibration data 318 can include one or more of stoma size data 319, stoma orientation data 320, stoma location data 321, and stoma shape data 322. The stoma size data 319 may refer to information associated with an actual or absolute size of the stoma 324. By way of example, an actual size of the stoma 324 may be 2 inches (or 5.08 centimeters). The stoma orientation data 320 may refer to information associated with a relative physical position or direction of the stoma 324 in relation to the user's body. The orientation data 320 can be used to rotationally position the ostomy appliance 2 at a certain degree as desired.

The stoma location data 321 may refer to information associated with an actual or absolute location of the stoma 324 in relation to the user's body. The stoma location data 321 can be used to properly position the ostomy appliance 2 on the stoma 324. The stoma shape data 322 may refer to information associated with external appearance characteristics of the stoma 324. The stoma shape data 322 can be used to determine a geometric shape of the stoma 324, such a round shape.

The application calibration unit 316 can determine and generate the size data 319 representative of a size of the stoma 324 as a function of the identified reference locations 354, 356, identified stoma 324 and the distance scale information 358. Using the extrapolation technique discussed above, the application calibration unit 316 can calculate the size of the stoma 324. The application calibration unit 316 may use extrapolation algorithms to accelerate the calculation of the stoma size using any two reference locations on the perimeter 334 of the stoma 324. A recursive algorithm for implementing the calculation of the stoma size may be employed to go beyond the original calculation range.

The application calibration unit 316 can also determine the orientation data 320 representative of an orientation of the stoma 324 with respect to at least one of the reference locations 354, 356, and generate the orientation data 320 representative of an orientation of the stoma 324 as a function of the identified reference locations 354, 356, identified stoma 324 and the distance scale information 358.

The application calibration unit 316 can also determine and generate the location data 321 representative of a location of the stoma 324 with respect to at least one of the reference locations 354, 356. The application calibration unit 316 can determine and generate the shape data 322 representative of a shape of the stoma 324 as a function of the identified reference locations 354, 356, identified stoma 324 and the distance scale information 358. The appliance calibration unit 316 can store the calibration data 318, the size data 319, the orientation data 320, the location data 321, and the shape data 322 in the memory 302 or any other suitable storage to suit the application.

Figure 22:
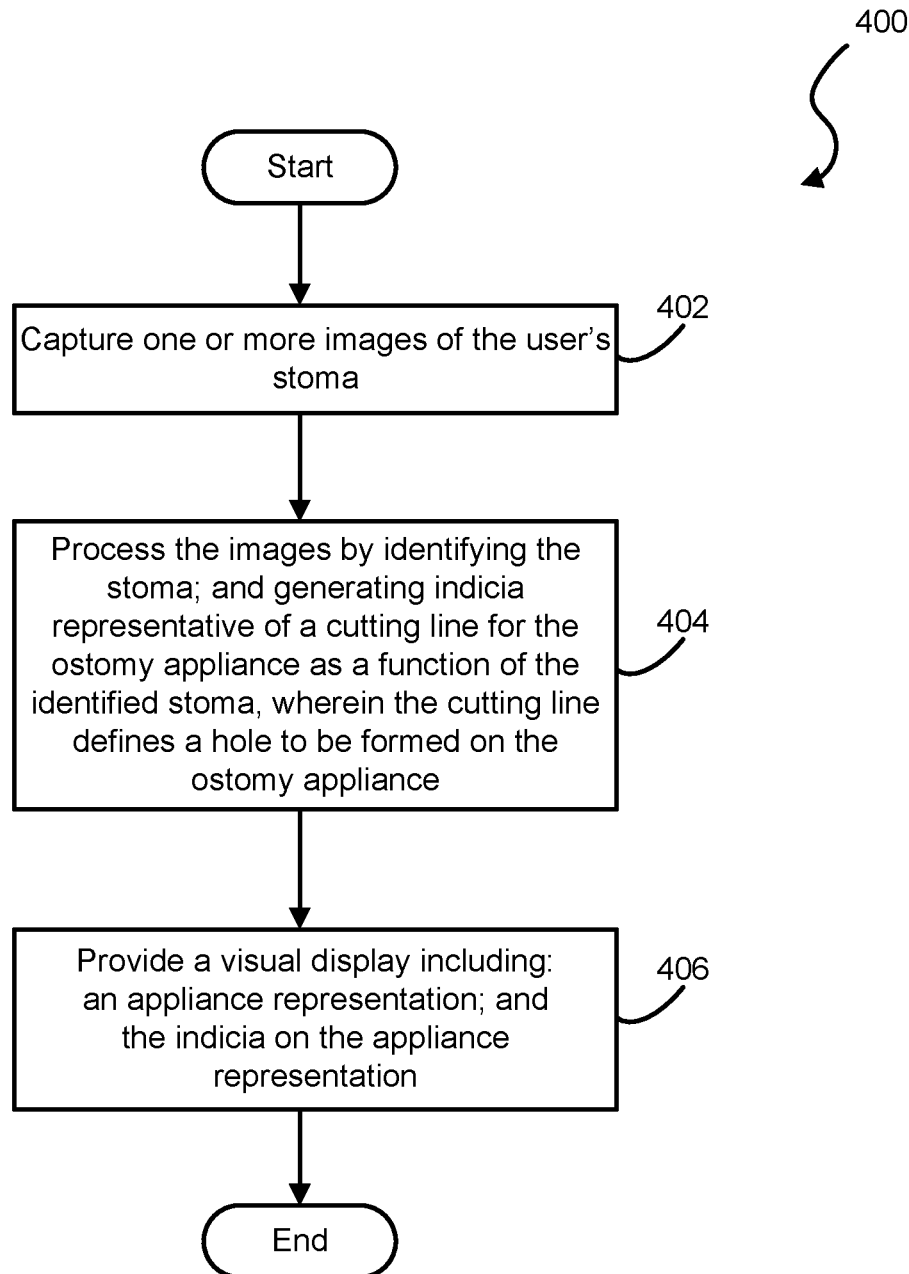
FIG. 22 is a flowchart illustrating an exemplary method of a cutting hole in the ostomy appliance.

FIG. 22 illustrates one example of a hole cutting method 400 for cutting a hole in the ostomy appliance 2 (e.g., a method for preparing an ostomy appliance for application). It will be described with reference to FIGS. 1-21. However, any suitable structure can be employed. Although three sub-blocks 402-406 are illustrated, other suitable sub-blocks can be employed to suit different applications.

In operation, at block 402, the camera 304 can capture one or more images of the user's stoma 324. At block 404, the stomal opening cutting unit 312 can process the images by identifying the stoma 324. The stomal opening cutting unit 312 can receive the images from the camera 304, and perform an object recognition algorithm to accurately identify the stoma 324. An appearance-based and/or feature-based method can be used to identify the stoma 324 in the images.

The stomal opening cutting unit 312 can generate the indicia 326 representative of a cutting line for the ostomy appliance 2 as a function of the identified stoma 324. The cutting line may define a hole (e.g., a stoma opening) to be formed on the ostomy appliance 2 (e.g., base plate 4) for receiving the stoma 324. The cutting line can be determined based on the calibration data 318 having the size data 319 and the shape data 322 associated with the stoma 324. The calibration data 318 can be determined based on the distance scale information 358 using two reference locations 354, 356. At block 406, the display device 308 can provide a visual display of the appliance representation 328 and the indicia 326 on the appliance representation. The appliance representation 328 may be the actual image of the ostomy appliance 2, and the indicia 326 may be displayed on top of the actual image of the ostomy appliance 2 for reference during the cutting process. Advantageously, the indicia 326 can be provided (e.g., displayed) for the user while a hole is being cut on the ostomy appliance 2. Other suitable combinations of method steps described above are contemplated.

Figure 23:
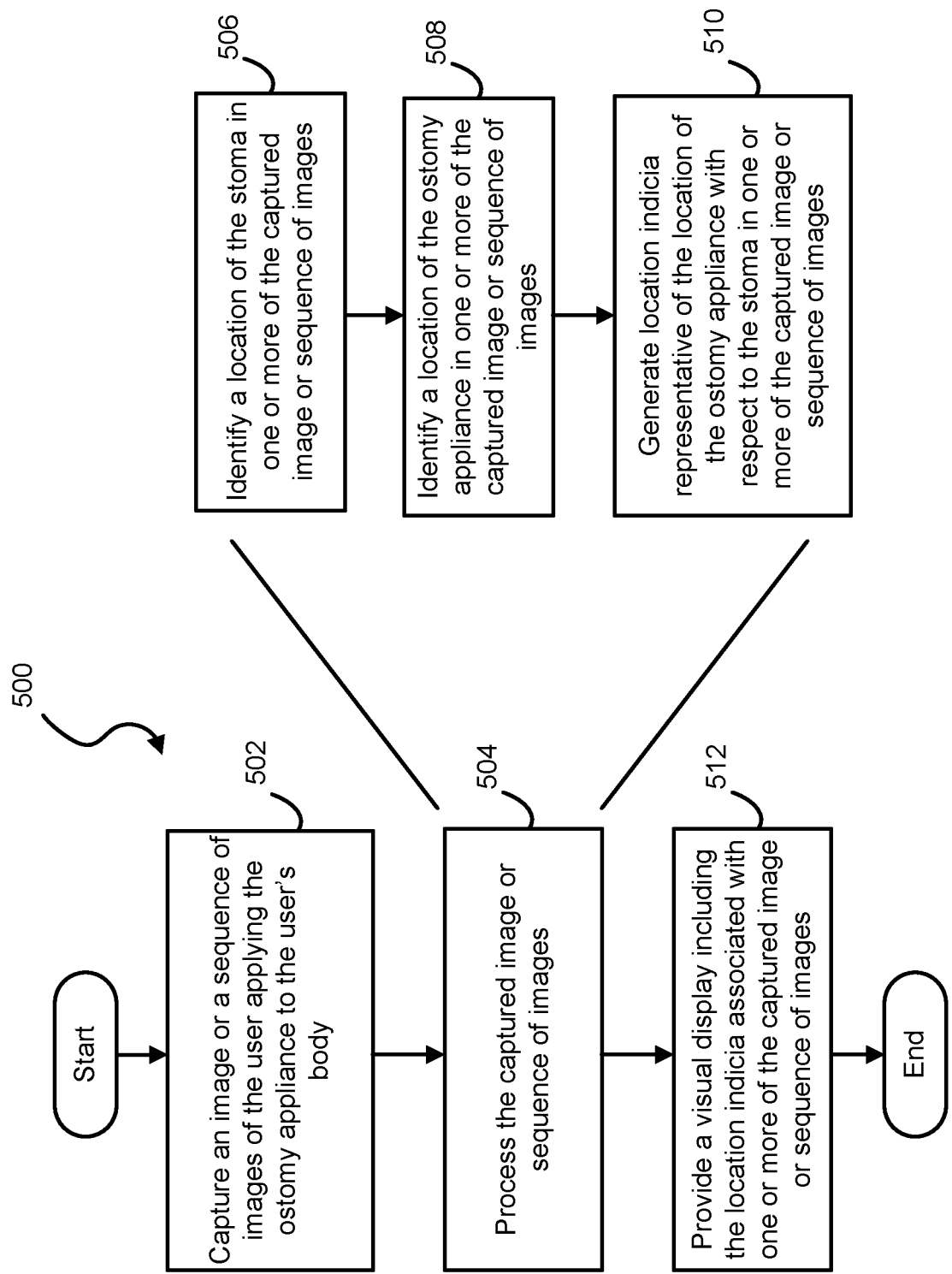
FIG. 23 is a flowchart illustrating an exemplary method of placing the ostomy appliance on the user.

FIG. 23 illustrates one example of an appliance placement method 500 for placing the ostomy appliance 2 on the user, e.g. for assisting the user in placing the ostomy appliance 2. It will be described with reference to FIGS. 1-21. However, any suitable structure can be employed. Although three sub-blocks 502-512 are illustrated, other suitable sub-blocks can be employed to suit different applications.

In operation, at block 502, the camera 304 can capture an image or a sequence of images of the user applying the ostomy appliance 2 to the user's body. At block 504, the appliance guidance unit 314 can process the captured image or sequence of images. The appliance guidance unit 314 can receive the captured image or sequence of images, and perform the fitting process using the calibration data 318 representative of a location of the stoma 324.

Specifically, at block 506, the appliance guidance unit 316 can identify the location of the stoma 324 in one or more of the captured image or sequence of images using at least two reference locations. The two reference locations on the user's body or the ostomy appliance 2 can be used to calculate the location of the stoma 324. Alternatively or additionally, the location of the stoma 324 can be determined based on the stoma location data 321 and at least one feature on the user's body. In this case, from the feature identified on the user's body, the appliance guidance unit 316 can determine an exact location of the stoma 324 using the stoma location data 321.

At block 508, the appliance guidance unit 316 can identify a location of the ostomy appliance 2 in one or more of the captured image or sequence of images. The location of the ostomy appliance 2 can be identified based on the object recognition algorithm. At block 510, the appliance guidance unit 316 can generate appliance location indicia 338 representative of the location of the ostomy appliance 2 with respect to the stoma 324 in one or more of the captured image or sequence of images. The appliance location indicia 338 and stoma location indicia 340 can be used by the display device 308, for displaying the appliance location indicia 338 and stoma location indicia 340 so as to properly align the cut line 327 on the stoma 324 or the graphical representation of the stoma 324.

At block 512, the display device 308 can provide a visual display of the location indicia 338 associated with one or more of the captured image or sequence of images. The appliance guidance unit 316 can generate and instruct the display device 308 to display a graphical simulation of the stoma 324 and the ostomy appliance 2 for aiding the user to properly apply the ostomy appliance 2 to the user's body using the appliance location indicia 338 and stoma location indicia 340.

Figure 24:
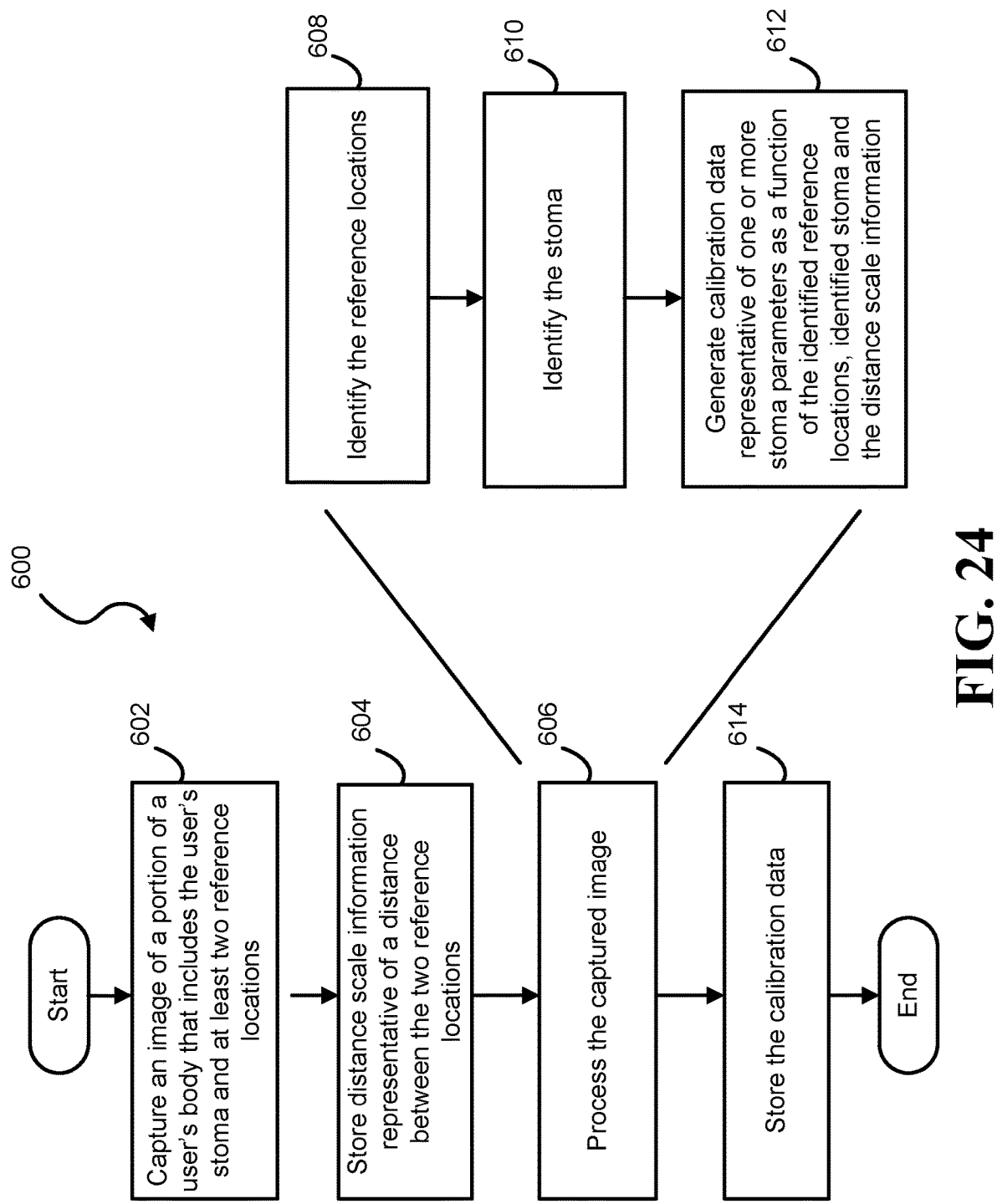
FIG. 24 is a flowchart illustrating an exemplary calibration method for the ostomy appliance.

FIG. 24 illustrates one example of a calibration method 600 for performing calibration steps for the ostomy appliance 2. It will be described with reference to FIGS. 1-21. However, any suitable structure can be employed. Although three sub-blocks 602-614 are illustrated, other suitable sub-blocks can be employed to suit different applications.

In operation, at block 602, the camera 304 can capture an image of a portion of a user's body that includes the user's stoma 324 and at least two reference locations 354, 356. At block 604, the appliance calibration unit 316 can receive the captured image of the user's body, and calculate the calibration data 318 based on the distance scale information 358 representative of the distance D between the two reference locations 354 and 356, e.g., using the extrapolation technique. The calibration data 318 can be determined based on the distance D. The distance D may be either manually received by the user or automatically retrieved by the appliance calibration unit 316 from the storage. The appliance calibration unit 316 can store the distance scale information 358 in the storage.

At block 606, the appliance calibration unit 316 can process the captured image. Specifically, at block 608, the appliance calibration unit 316 can identify the reference locations 354, 356 on the user's body using the object recognition algorithm. At block 610, the appliance calibration unit 316 can identify the stoma 324, e.g., using the object recognition algorithm. At block 612, the appliance calibration unit 316 can generate the calibration data 318 representative of one or more stoma parameters as a function of the identified reference locations 354, 356, identified stoma 324 and the distance scale information 358. The stoma parameters can include information related to at least one of: size, orientation, location, and shape data associated with the stoma 324. At block 614, the appliance calibration unit 316 can store the calibration data 318 in the memory 302. The stored calibration data 318 may be used to perform an accurate alignment of the cut line 327 to provide information for the fitting process performed by the accessory device 8.

Figure 25:
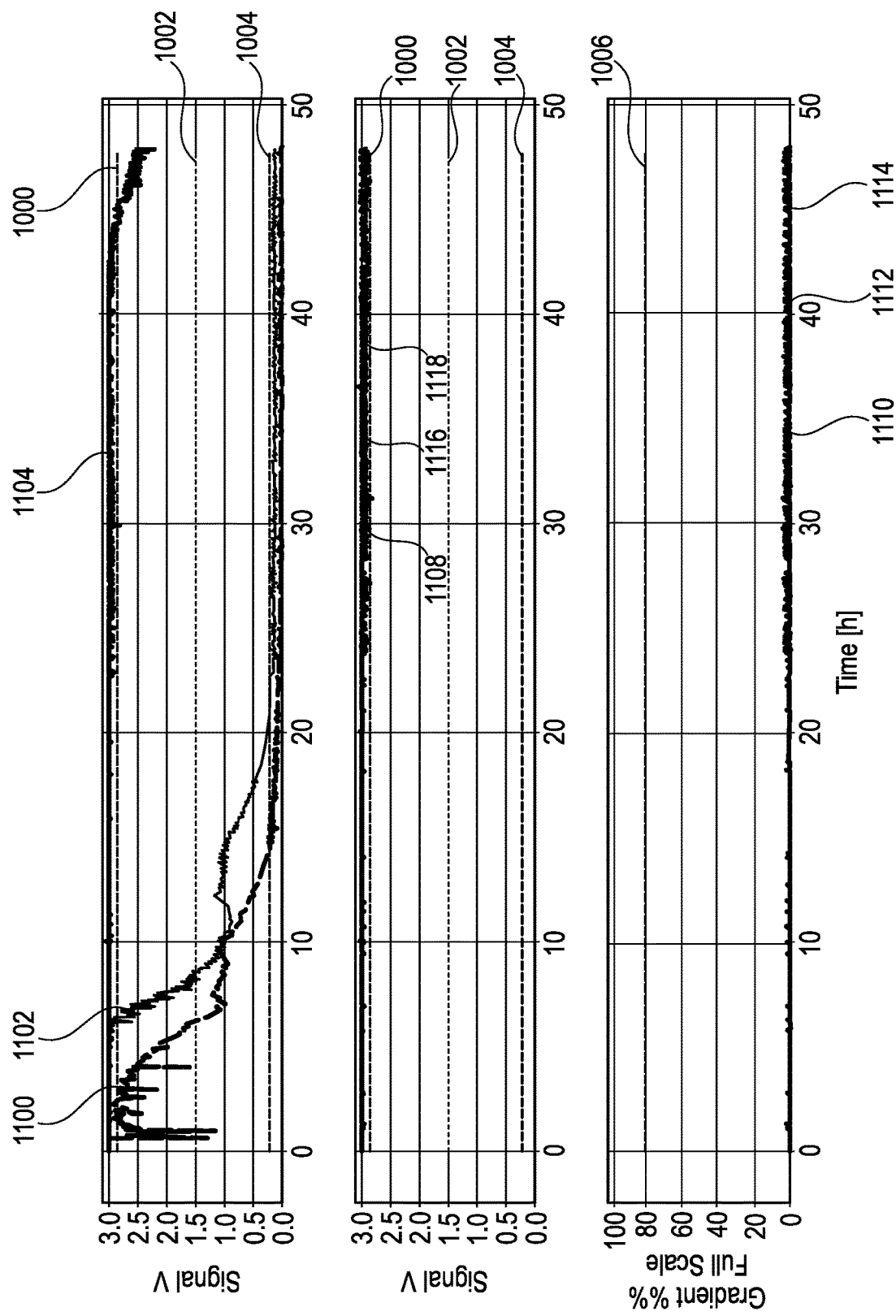
FIG. 25 is an exemplary graphical representation of parameter data as a function of time.

FIG. 25 shows an exemplary graphical representation of parameter data as a function of time. In this example, the parameter data in the y-axis is in Volts and time is in the x-axis. Curve 1100 shows, as a function of time, a first parameter data indicative of voltage measured by the first electrode pair of the base plate. Curve 1102 shows, as a function of time, a second parameter data indicative of voltage measured by the second electrode pair of the base plate. Curve 1104 shows, as a function of time, a third parameter data indicative of voltage measured by the third electrode pair of the base plate.-Curves 1108, 1116, 1118 show, as a function of time, fourth primary parameter indicative of voltage measured by the fourth electrode pair of the base plate, fourth secondary parameter indicative of voltage measured by the fourth electrode and the fifth electrode of the base plate, and fourth tertiary parameter indicative of voltage measured by the fifth electrode pair of the base plate respectively. Curves 1110, 1112, 1114 show, as a function of time, a gradient of fourth primary parameter indicative of voltage gradient measured by the fourth electrode pair of the base plate, a gradient of fourth secondary parameter indicative of voltage gradient measured by the fourth electrode and the fifth electrode of the base plate, and a gradient of fourth tertiary parameter indicative of voltage gradient measured by the fifth electrode pair of the base plate respectively. FIG. 25 shows the upper voltage threshold value represented as curve 1000, the medium voltage threshold value represented as curve 1002, the lower voltage threshold value represented as curve 1004, and curve 1006 is a gradient limit.

Curves 1108, 1116, 1118 as well as curves 1110, 1112, 1114 show that no moisture is detected at the proximal side of the first adhesive layer by the fourth electrode pair.

At a time less than 5 h, curve 1100 shows that moisture is detected by the first electrode pair as the first parameter data crosses the upper voltage threshold value while curve 1102 shows that moisture is not detected by the second electrode pair as the second parameter data has not crossed the upper voltage threshold value. At this stage, it is determined that the ostomy appliance is in a first operating state.

At time between 5 h and 10 h, curve 1102 shows that moisture is detected by the second electrode pair as the second parameter data crosses the upper voltage threshold value. At this stage, it is determined that the ostomy appliance is in a second operating state.

At time around 45, curve 1104 shows that moisture is detected by the third electrode pair as the third parameter data crosses the upper voltage threshold value. At this stage, it is determined that the ostomy appliance is in a third operating state.

Figure 26:
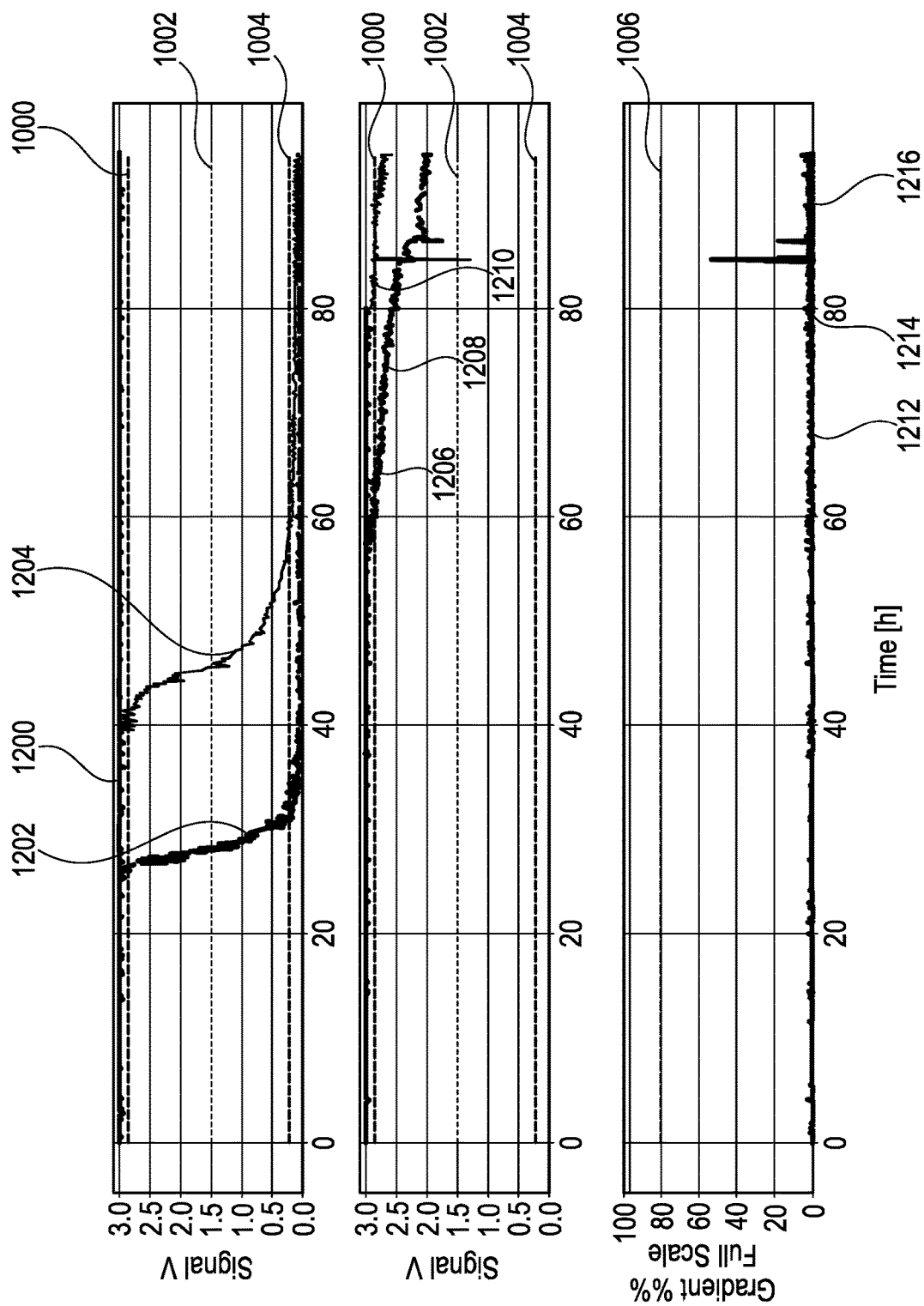
FIG. 26 is an exemplary graphical representation of parameter data as a function of time.

FIG. 26 shows an exemplary graphical representation of parameter data as a function of time. In this example, the parameter data in the y-axis is in Volts and time is in the x-axis. Curve 1202 shows, as a function of time, a first parameter data indicative of voltage measured by the first electrode pair of the base plate. Curve 1204 shows, as a function of time, a second parameter data indicative of voltage measured by the second electrode pair of the base plate. Curve 1200 shows, as a function of time, a third parameter data indicative of voltage measured by the third electrode pair of the base plate. Curves 1206, 1208, 1210 show, as a function of time, fourth primary parameter indicative of voltage measured by the fourth electrode pair of the base plate, fourth secondary parameter indicative of voltage measured by the fourth electrode and the fifth electrode of the base plate, and fourth tertiary parameter indicative of voltage measured by the fifth electrode pair of the base plate respectively. Curves 1212, 1214, 1216 show, as a function of time, a gradient of fourth primary parameter indicative of voltage gradient measured by the fourth electrode pair of the base plate, a gradient of fourth secondary parameter indicative of voltage gradient measured by the fourth electrode and the fifth electrode of the base plate, and a gradient of fourth tertiary parameter indicative of voltage gradient measured by the fifth electrode pair of the base plate respectively. FIG. 26 shows the upper voltage threshold value represented as curve 1000, the medium voltage threshold value represented as curve 1002, the lower voltage threshold value represented as curve 1004, and curve 1006 represents a gradient limit.

Curves 1206, 1208, 1210 as well as curves 1212, 1214, 1216 show that moisture is detected at the proximal side of the first adhesive layer by the fourth electrode pair, the fourth and fifth electrode, and the fifth electrode pair at a time starting at 60 h until 90 h. As the three electrode pairs are triggered as shown by the decreases shown by 1206, 1208, 1210 and as the curves 1212, 1214, 1216 show a gradient below 80%, this is indicative of the presence of sweat at the proximal side of the first adhesive layer.

At a time of 30 min, curve 1202 shows that moisture is detected by the first electrode pair as the first parameter data crosses the upper voltage threshold value while curve 1204 shows that moisture is not detected by the second electrode pair as the second parameter data has not crossed the upper voltage threshold value. At this stage, it is determined that the ostomy appliance is in a first operating state.

At time around 40 h, curve 1204 shows that moisture is detected by the second electrode pair as the second parameter data crosses the upper voltage threshold value. At this stage, it is determined that the ostomy appliance is in a second operating state.

Figure 27:
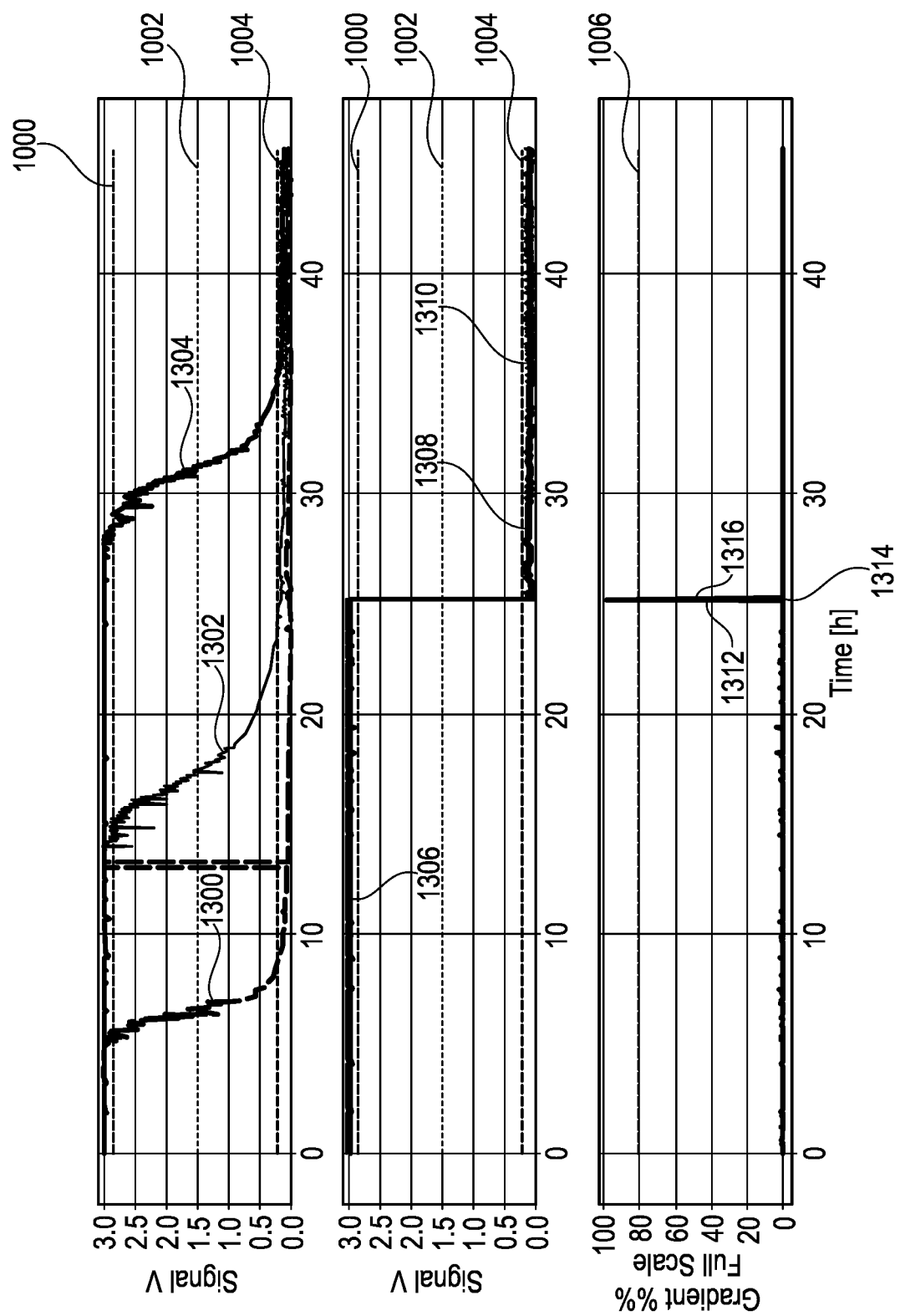
FIG. 27 is an exemplary graphical representation of parameter data as a function of time.

FIG. 27 shows an exemplary graphical representation of parameter data as a function of time. In this example, the parameter data in the y-axis is in Volts and time is in the x-axis. Curve 1300 shows, as a function of time, a first parameter data indicative of voltage measured by the first electrode pair of the base plate. Curve 1302 shows, as a function of time, a second parameter data indicative of voltage measured by the second electrode pair of the base plate. Curve 1304 shows, as a function of time, a third parameter data indicative of voltage measured by the third electrode pair of the base plate. Curves 1306, 1308, 1310 show, as a function of time, fourth primary parameter indicative of voltage measured by the fourth electrode pair of the base plate, fourth secondary parameter indicative of voltage measured by the fourth electrode and the fifth electrode of the base plate, and fourth tertiary parameter indicative of voltage measured by the fifth electrode pair of the base plate respectively. Curves 1312, 1314, 1316 show, as a function of time, a gradient of fourth primary parameter indicative of voltage gradient measured by the fourth electrode pair of the base plate, a gradient of fourth secondary parameter indicative of voltage gradient measured by the fourth electrode and the fifth electrode of the base plate, and a gradient of fourth tertiary parameter indicative of voltage gradient measured by the fifth electrode pair of the base plate respectively. FIG. 27 shows the upper voltage threshold value represented as curve 1000, the medium voltage threshold value represented as curve 1002, the lower voltage threshold value represented as curve 1004, and curve 1006 is a gradient limit.

Curves 1306, 1308, 1310 as well as curves 1312, 1314, 1316 show that moisture is detected at the proximal side of the first adhesive layer by the fourth electrode pair at a time starting at around 25 h. As leakage electrodes (i.e. the fourth electrode pair, the fourth and fifth electrode, and the fifth electrode pair) are trigger as shown by the decreases shown by 1306, 1308, 1310 and as curve 1312, 1314, 1316 show a gradient above 80%, this is indicative of the presence of output at the proximal side of the first adhesive layer. This indicate severe leakage. It may be determined that the ostomy appliance is in a sixth operating state.

At a time of 5 h, curve 1300 shows that moisture is detected by the first electrode pair as the first parameter data crosses the upper voltage threshold value while curve 1302 shows that moisture is not detected by the second electrode pair as the second parameter data has not crossed the upper voltage threshold value. At this stage, it is determined that the ostomy appliance is in a first operating state.

At time around 15 h, curve 1302 shows that moisture is detected by the second electrode pair as the second parameter data crosses the upper voltage threshold value. At this stage, it is determined that the ostomy appliance is in a second operating state.

At time around 30 h, curve 1304 shows that moisture is detected by the third electrode pair as the third parameter data crosses the upper voltage threshold value. In an example where the curves 1306, 1308, 1310 had not dropped below corresponding thresholds, curve 1304 indicates that moisture has reached the third electrode pair, and the present disclosure enables determining that the ostomy appliance is in a third operating state.

Figure 28:
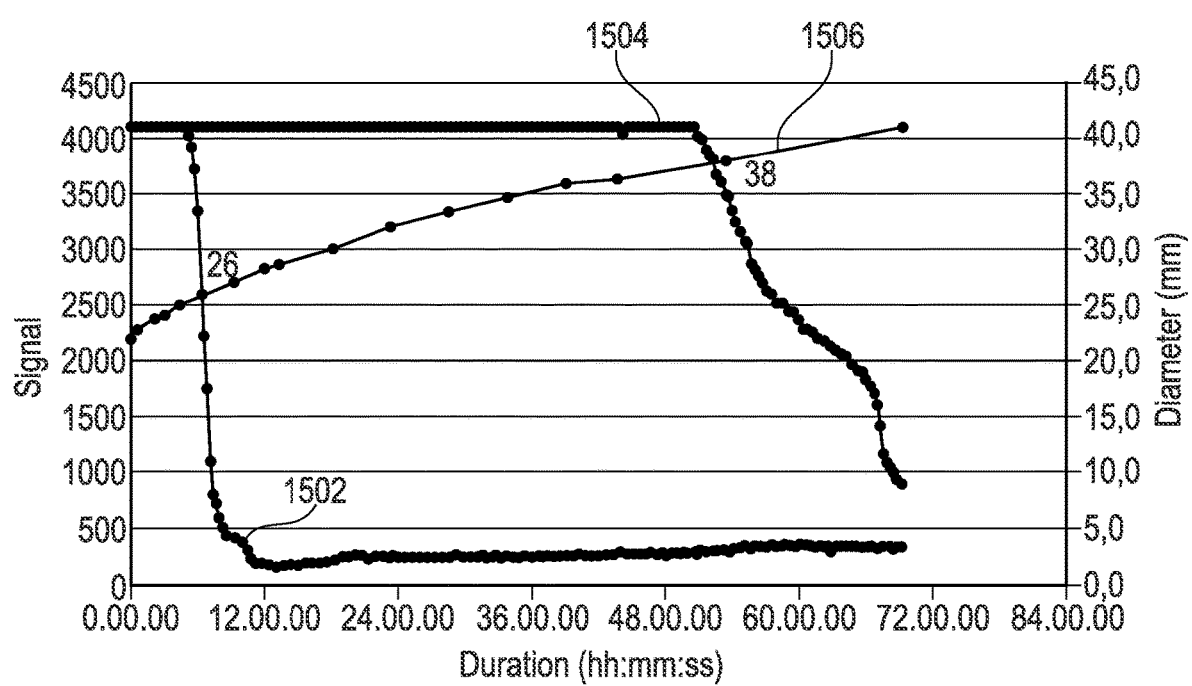
FIG. 28 is an exemplary graphical representation of parameter data as a function of time and a whitening zone diameter as a function of time.

FIG. 28 shows an exemplary graphical representation of parameter data as a function of time and a whitening zone diameter (e.g. related to a radial thickness of a whitening ring surrounding the stomal opening) as a function of time. FIG. 28 illustrates the moisture propagation in the first adhesive layer as a function of time, and illustrates a correlation between parameter data detected by the first electrode pair and the second electrode pair of the base plate and actual moisture on the proximal surface of the first adhesive layer of the base plate. The actual moisture propagation in the first adhesive layer may appear as a whitening zone (e.g. a white ring around the stomal opening) in the first adhesive layer. Moisture affects the first adhesive layer in that the moisture reacts with the composition of the first adhesive layer to form the white ring around the stomal opening, and thereby reduces adhesive performance of the base plate. FIG. 28 is obtained by experiments where water is applied from the stomal opening of the based plate to follow, using the electrodes of the base plate, the radial propagation of moisture leading to radial erosion of the first adhesive layer of the base plate.

Curve 1502 shows, as a function of time, a first parameter data indicative of voltage measured by the first electrode pair of the base plate. Curve 1504 shows, as a function of time, a second parameter data indicative of voltage measured by the second electrode pair of the base plate. Curve 1506 shows a diameter of the white ring as a function of time. The first parameter data shows a decrease in e.g. voltage measured by the first electrode pair over time. It is also seen that the voltage of the second electrode pair drops at a later time than when the first parameter data shows a decrease in e.g. voltage dropped. This correlates well with the diameter of the white ring which goes from around 25-26 mm when the first electrode pair is triggered (e.g. first parameter data shows a decrease) to 38 mm when the second electrode pair is triggered (second parameter data shows a decrease). This corresponds substantially to the location of the first electrode pair at twice the first radial distance R1, and of the second electrode pair at twice the second radial distance R2.

It is noted that various regions and countries have various routines and recommendations to support optimal use of an ostomy appliance. For example, in regions of Europe, it may be indicated to the user that an ostomy appliance with a base plate as disclosed herein is an optimal state (corresponding to a first operating state) when the radial thickness of the whitening ring is between 0-15 mm (for a user not in compliance with a preferred use), such as between 0-7 mm (for a user in compliance with a preferred use), such as between 0-5 mm (recommended by a nurse).

For example, in Europe, it may be indicated to the user that an ostomy appliance with a base plate as disclosed herein is in suboptimal state (corresponding to a second operating state) and thereby indicate a consideration to change the base plate when the radial thickness of the whitening ring is such as between 5-10 mm (recommended by a nurse), between 7 mm and 10 mm (for a user in compliance with a preferred use), and/or between 15 mm and 30 mm (for a user not in compliance with a preferred use).

For example, in Europe, it may be indicated to the user that an ostomy appliance with a base plate as disclosed herein is in a poor state (corresponding to a third operating state) and indicate a request to change the base plate when the radial thickness of the whitening ring is more than 10 mm (recommended by a nurse), such as more than 15 mm (for a user in compliance with a preferred use), such as more than 30 mm (for a user not in compliance with a preferred use).

For example, in other regions (e.g. America), it may be indicated to the user that an ostomy appliance with a base plate as disclosed herein is an optimal state (corresponding to a first operating state) when the radial thickness of the whitening ring is between 0-20 mm (for a user not in compliance with a preferred use), such as between 0-10 mm (for a user in compliance with a preferred use), such as between 0-10 mm (recommended by a nurse).

For example, in other regions (e.g. America), it may be indicated to the user that an ostomy appliance with a base plate as disclosed herein is in suboptimal state (corresponding to a second operating state) and thereby indicate a consideration to change the base plate when the radial thickness of the whitening ring is such as between 10 mm and 20 m (recommended by a nurse), between 10 m and 20 (for a user in compliance with a preferred use), and/or between 20 m and 40 mm (for a user not in compliance with a preferred use).

For example, in other regions (e.g. America), it may be indicated to the user that an ostomy appliance with a base plate as disclosed herein is in a poor state (corresponding to a third operating state) and indicate a request to change the base plate when the radial thickness of the whitening ring is more than 20 mm (recommended by a nurse), such as more than 20 mm (for a user in compliance with a preferred use), such as more than 40 mm (for a user not in compliance with a preferred use).

The disclosed methods, ostomy appliances, monitor devices, and accessory devices allow to accommodate the regional preferences of user in their use of the ostomy appliance so as to adjust thresholds for the operating states to the regional preference or use.

Figure 29A:
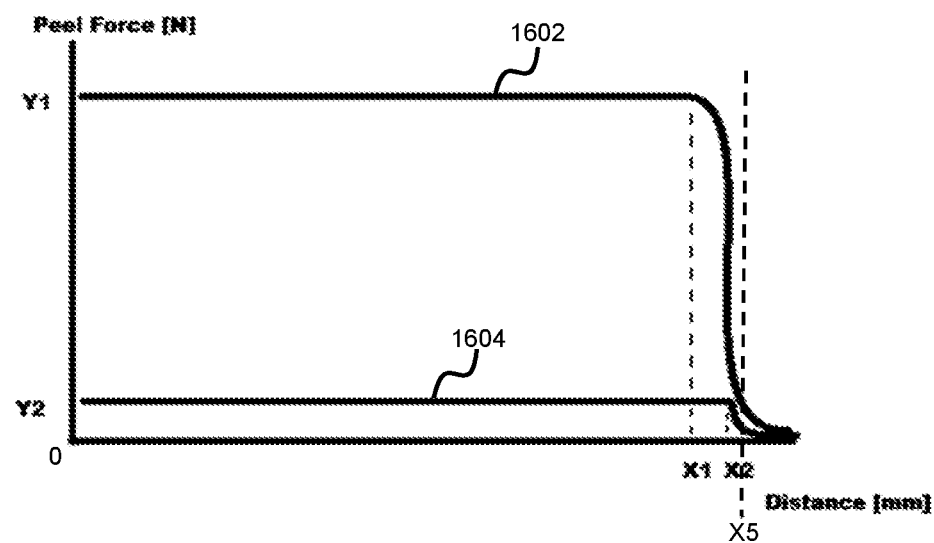
FIGS. 29A-29B are exemplary graphical representations of peel force as a function of a peeling distance travelled by a peeling action exercising the peel force on a first adhesive layer of a base plate.
Figure 29B:
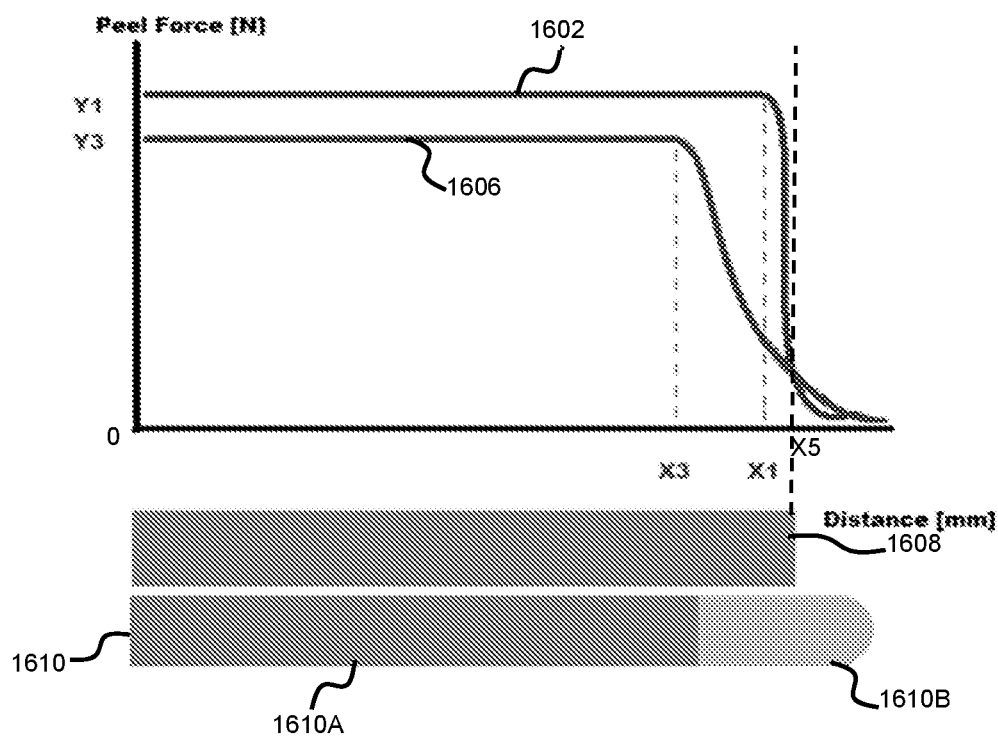

FIGS. 29A-29B shows exemplary graphical representations of peel force as a function of a peeling distance travelled by a peeling action exercising the peel force (e.g. perpendicularly to the proximal (or distal) surface of the first adhesive layer) on a first adhesive layer of a base plate disclosed herein. The peel force relates to a required force to peel the first adhesive layer off the skin surface. The peeling distance is with respect to one end of the first adhesive layer where the peel force starts to be exercised. The peeling distance relates to the size or length of the first adhesive layer and thereby may relate to a size or length of a portion the first adhesive layer affected by moisture and of a portion of the first adhesive layer not affected by moisture. The peel forces illustrated in FIGS. 29A-29B are representative of adhesive performance of the first adhesive layer of the base plate to the skin surface.

Composition of the first adhesive layer of the base plate as disclosed herein in one or more embodiments is formulated to provide adhesion of the base plate to the skin surface of the user when the base plate is worn and to maintain a dry and healthy skin surface. Avoiding maceration of skin when occluding the skin with an adhesive is done by transporting sweat away from the skin and into the first adhesive layer by means of e.g. hydrocolloid types and adhesive (e.g. hydrocolloid adhesives) forming part of an absorbing element of the first adhesive layer.

For example, when the absorbing element is in contact with moisture, (e.g. water, sweat, urine or faeces), the absorbing element absorb the moisture. This reduces the adhesion of the first adhesive layer to the skin.

For example, the first adhesive layer goes from a dry adhesive state with acceptable adhesive performance (e.g. acceptable adhesion and cohesion) in to a wet adhesive state (e.g. reduced or non adhesion and low cohesion gel).

Curve 1602 of FIGS. 29A and 29B shows a peel force applied to the first adhesive layer as a function of a peeling distance travelled by a peeling action exercising the peel force on the first adhesive layer in a dry adhesive state, (e.g. not affected by moisture). The peel force is expressed in Newtons while the peeling distance is expressed in mm. The length of the first adhesive layer in dry adhesive state is illustrated by X5, corresponding to length of the first adhesive layer 1608 in dry adhesive state.

Curve 1602 shows that the peel force applied to the first adhesive layer in a dry adhesive state is equal to Y1 when the peeling distance is less than X1. At X1, the peeling force drops as the peeling distance increases towards X5 and the end of the first adhesive layer.

Curve 1604 of FIG. 29A shows a peel force applied to the first adhesive layer as a function of a peeling distance travelled by a peeling action exercising the peel force on the first adhesive layer in a wet adhesive state, (e.g. affected by moisture to the point of reaching a completely wet adhesive state, where the first adhesive layer has become a gel).

Curve 1604 shows that when the peeling distance is less than X2, the peel force applied to the first adhesive layer in a wet adhesive state is equal to Y2 which has much lower value than Y1. This shows that the adhesive performance of the first adhesive layer is reduced when the first adhesive layer is in a wet adhesive state. At X2, the peeling force drops as the peeling distance increases until the end of the first adhesive layer. It is noted that X2 is larger than X1, because the first adhesive layer in a wet adhesive state extends in volume, and thus in length due to the gelling of the components of the first adhesive layer.

The peel experiment illustrated in FIG. 29A shows a loss of adhesive performance when the first adhesive is in a wet adhesive state.

Curve 1606 of FIG. 29B shows a peel force applied to the first adhesive layer as a function of a peeling distance travelled by a peeling action exercising the peel force on the first adhesive layer illustrated 1610 which comprises a first portion 1610A in a dry adhesive state and a second portion 1610B in a wet adhesive state, (e.g. affected by moisture to the point of reaching a completely wet adhesive state, where the first adhesive layer has become a gel).

Curve 1606 shows that when the peeling distance is less than X3, the peel force applied to the first adhesive layer in a wet adhesive state is equal to Y3 which has lower value than Y1. This shows that the adhesive performance of the first adhesive layer is reduced when the first adhesive layer comprises a portion in a wet adhesive state. At X3, the peeling force drops as the peeling distance increases until the end of the first adhesive layer. It is noted that X3 corresponds to the length of the portion 1610A in dry adhesive state.

The peel experiment illustrated in FIG. 29B shows a loss of adhesive performance when the first adhesive is partly in a wet adhesive state.

Accordingly, FIG. 29A-29B demonstrate that the operating state determined based on monitor data is indicative of adhesive performance of the base plate.

The above detailed description of the present disclosure and the examples described therein have been presented for the purposes of illustration and description only and not by limitation. It is therefore contemplated that the present disclosure covers any and all modifications, variations or equivalents that fall within the spirit and scope of the basic underlying principles disclosed above and claimed herein.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

LIST OF REFERENCES 1 ostomy system
2 ostomy appliance
4 base plate
6 monitor device
8 accessory device
10 server device
12 network
14 coupling member
16 coupling ring
18, 18A, 18B, 18C, 18D stomal opening
19 center point
20 docking station
22 first connector
24 user interface
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
121 power unit
122 antenna
124 wireless transceiver
126 loudspeaker
128 haptic feedback element
140 sensor unit
200 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
204A distal surface of electrode assembly
204B proximal surface of electrode assembly
206 release liner
206A distal surface of the release liner
206B proximal surface of the release liner
208 top layer
208A distal surface of the top layer
208B proximal surface of the top layer
209 coupling ring
210 coupling part of first connector
211 first connector
212 terminals of first connector
213 first intermediate element
213A distal surface of first intermediate element
213B proximal surface of first intermediate element
214 support layer of electrode assembly
214A distal surface of support layer
214B proximal surface of support layer
216 electrodes of electrode assembly
217 connection parts of electrodes
218, 219 masking element
218A distal surface of masking element
218B proximal surface of masking element
220, 220A, 220B electrode configuration
222 ground electrode
222A ground connection part
222B ground sensing part
224 first electrode
224A first connection part
224B first sensing part
226 second electrode
226A second connection part
226B second sensing part
228 third electrode
228A third connection part
228B third sensing part
230 fourth electrode
230A fourth connection part
230B fourth sensing part
232 fifth electrode
232A fifth connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
29A fifth terminal
300 processor
302 memory
304 camera
306 input device
308 display device/visual display
310 bus
312 stomal opening cutting unit
313 convolution neural network module 314 appliance guidance unit
316 appliance calibration unit
318 calibration data
319 size data
320 orientation data
321 location data
322 shape data
324 stoma
326 indicia
327 cut line
328 appliance representation
330 predefined hole indicia
332 ostomy bag
334 perimeter
338 desired location of bag
339 desired location of base plate
340 virtual stoma
341 desired location of cut line
342 quality indicator
344 red light
346 yellow light
348 green light
350 direction indicator
352 target location indicia
353 current location indicia
354 first reference location
356 second reference location
358 distance scale information
360 machine-readable code
400 hole cutting method
402 capture one or more images of the user's stoma
404 process the images by identifying the stoma; and generating indicia representative of a cutting line for the ostomy appliance as a function of the identified stoma, wherein the cutting line defines a hole to be formed on the ostomy appliance
406 provide a visual display including: an appliance representation; and the indicia on the appliance representation
500 appliance placement method
502 capture an image or a sequence of images of the user applying the ostomy appliance to the user's body
504 process the captured image or sequence of images
506 identify a location of the stoma in one or more of the captured image or sequence of images
508 identify a location of the ostomy appliance in one or more of the captured image or sequence of images
510 generate location indicia representative of the location of the ostomy appliance with respect to the stoma in one or more of the captured image or sequence of images
512 provide a visual display including the location indicia associated with one or more of the captured image or sequence of images
600 calibration method
602 capture an image of a portion of a user's body that includes the user's stoma and at least two reference locations
604 store distance scale information representative of a distance between the two reference locations
606 process the captured image
608 identify the reference locations
610 identify the stoma
612 generate calibration data representative of one or more stoma parameters as a function of the identified reference locations, identified stoma and the distance scale information
614 store the calibration data
1000 curve representing the upper voltage threshold value
1002 curve representing the medium voltage threshold value
1004 curve representing the lower voltage threshold value
1006 curve representing a gradient limit
1100 curve showing, as a function of time, a first parameter data indicative of voltage measured by the first electrode pair of the base plate
1102 curve showing, as a function of time, a second parameter data indicative of voltage measured by the second electrode pair of the base plate
1104 curve showing, as a function of time, a third parameter data indicative of voltage measured by the third electrode pair of the base plate
1108 curve showing, as a function of time, a fourth primary parameter indicative of voltage measured by the fourth electrode pair of the base plate
1110 curve showing, as a function of time, a gradient of fourth primary parameter indicative of voltage gradient
1112 curve showing, as a function of time, a gradient of fourth secondary parameter indicative of voltage gradient measured
1114 curve showing, as a function of time, a gradient of fourth tertiary parameter indicative of voltage gradient measured
1116 curve showing, as a function of time, a fourth secondary parameter indicative of voltage measured
1118 curve showing, as a function of time, a fourth tertiary parameter indicative of voltage measured
1200 curve showing, as a function of time, a third parameter data indicative of voltage measured by the third electrode pair of the base plate
1202 curve showing, as a function of time, a first parameter data indicative of voltage measured by the first electrode pair of the base plate
1204 curve showing, as a function of time, a second parameter data indicative of voltage measured by the second electrode pair of the base plate
1206 curve showing, as a function of time, a fourth primary parameter indicative of voltage measured by the fourth electrode pair of the base plate
1208 curve showing, as a function of time, a fourth secondary parameter indicative of voltage measured
1210 curve showing, as a function of time, a fourth tertiary parameter indicative of voltage measured
1212 curve showing, as a function of time, a gradient of fourth primary parameter indicative of voltage gradient measured by the fourth electrode pair of the base plate
1214 curve showing, as a function of time, a gradient of fourth secondary parameter data indicative of voltage gradient measured
1216 curve showing, as a function of time, a gradient of fourth tertiary parameter indicative of voltage gradient measured
1300 curve showing, as a function of time, a first parameter data indicative of voltage measured by the first electrode pair of the base plate
1302 curve showing, as a function of time, a second parameter data indicative of voltage measured by the second electrode pair of the base plate
1304 curve showing, as a function of time, a third parameter data indicative of voltage measured by the third electrode pair of the base plate
1306 curve showing, as a function of time, a fourth primary parameter indicative of voltage measured by the fourth electrode pair of the base plate
1308 curve showing, as a function of time, a fourth seondary parameter indicative of voltage measured 1310 curve showing, as a function of time, a fourth tertiary parameter indicative of voltage measured
1312 curve showing, as a function of time, a gradient of fourth primary parameter indicative of voltage gradient measured by the fourth electrode pair of the base plate
1314 curve showing, as a function of time, a gradient of fourth secondary parameter indicative of voltage gradient measured
1316 curve showing, as a function of time, a gradient of fourth tertiary parameter indicative of voltage gradient measured
1502 curve showing, as a function of time, a first parameter data indicative of voltage measured by the first electrode pair of the base plate
1504 curve showing, as a function of time, a second parameter data indicative of voltage measured by the second electrode pair of the base plate
1506 curve showing a diameter of the white ring as a function of time
1602 curve showing peel force applied to the first adhesive layer in a dry adhesive state as a function of peeling distance
1604 a peel force applied to the first adhesive layer as a function of a peeling distance travelled by a peeling action exercising the peel force on the first adhesive layer in a wet adhesive state
1606 a peel force applied to the first adhesive layer as a function of a peeling distance travelled by a peeling action exercising the peel force on the first adhesive layer partially wet
1608 length of the first adhesive layer 1608 in dry adhesive state
1610 the first adhesive layer which comprises a first portion in a dry adhesive state and a second portion in a wet adhesive state
1610A a first portion in a dry adhesive state
1610B a second portion in a wet adhesive state
R1 first radial distance
RG1 first ground distance
R2 second radial distance
RG2 second ground distance
R3 third radial distance
RG3 third ground distance The following is claimed:

1. A method for operating an accessory device to guide the placement of a medical appliance on a user having a stoma, comprising:
   capturing an image or a sequence of images of the user applying the medical appliance to the user's body;
   processing the captured image or sequence of images, including:
      identifying a location of the stoma in one or more of the captured image or sequence of images;
      identifying a location of the medical appliance in one or more of the captured image or sequence of images; and
      generating location indicia representative of the location of the medical appliance with respect to the stoma in one or more of the captured image or sequence of images; and
   providing a visual display including the location indicia associated with one or more of the captured image or sequence of images.

2. The method of claim 1, wherein:
   generating the location indicia includes:
      generating a stoma location representation; and
      generating an appliance location representation; and
   providing the visual display includes providing a visual display including the stoma location representation and the appliance location representation.

3. The method of claim 2, wherein generating and displaying the stoma location representation includes generating and displaying a graphical simulation of the stoma.

4. The method of claim 2, wherein generating and displaying the appliance location representation includes generating and displaying a graphical simulation of the medical appliance.

5. The method of claim 2, wherein generating and displaying the appliance location representation includes generating and displaying an image of at least a portion of the actual medical appliance from one or more of the captured image or sequence of images.

6. The method of claim 1, wherein:
   generating the location indicia includes generating a quality indicator representative of the position of the medical appliance with respect to a desired position with respect to the stoma; and
   providing a visual display includes providing a visual display of the quality indicator.

7. The method of claim 1, wherein:
   generating the location indicia includes generating a direction indicator representative of a direction the medical appliance should be moved to locate the medical appliance at a desired position with respect to the stoma; and
   providing the visual display includes providing a visual display of the direction indicator.

8. The method of claim 1, wherein providing a visual display includes providing visual display of target indicia representative of a desired position of the medical appliance on the user.

9. The method of claim 1, and further including receiving calibration data representative of the location of the stoma on the user's body with respect to a reference indicator on the user's body that is visible in one or more of the captured image or sequence of images.

10. The method of claim wherein:
    processing the captured image or sequence of images further includes identifying the reference indicator on the user's body; and
    identifying the location of the stoma includes identifying the location of the stoma as a function of the identified reference indicator on the user's body and the calibration data.

11. The method of claim 1, wherein identifying the location of the medical appliance includes identifying a reference indicator on the medical appliance.

12. The method of claim 1, to guide the placement of an medical appliance including a base plate and bag attached to the base plate, wherein the base plate is not visible in the captured image or sequence of captured images.

13. The method of claim 1, to guide the placement of a base plate of a multi-piece medical appliance including a bag attachable to the base plate after the base plate is placed on the user's body.

14. The method of claim 1, wherein capturing the image or sequence of images, processing the captured image or sequence of images and providing the visual display are performed by an accessory device including a camera, image processor and display device.

15. The method of claim 1, wherein identifying the location of the stoma in one or more of the captured image or sequence of images and/or identifying the location of the medical appliance in one or more of the captured image or sequence of images is performed using machine learning.

16. An accessory device including a camera, image processor, display and stored instructions for performing the method of claim 1.

17. Storage media with stored instructions for performing the method of claim 1.

* * * * *